US011420979B2

(12) United States Patent
Choe et al.

(10) Patent No.: US 11,420,979 B2
(45) Date of Patent: Aug. 23, 2022

(54) ORGANIC COMPOUND, ORGANIC LIGHT EMITTING DIODE AND ORGANIC LIGHT EMITTING DEVICE HAVING THE COMPOUND

(71) Applicants: LG Display Co., Ltd., Seoul (KR); Soulbrain Co., Ltd., Seongnam-si (KR)

(72) Inventors: Ik-Rang Choe, Paju-si (KR); Tae-Ryang Hong, Paju-si (KR); Jun-Yun Kim, Paju-si (KR); Jin Hee Kim, Paju-si (KR); Eun Chul Shin, Paju-si (KR)

(73) Assignees: LG DISPLAY CO., LTD., Seoul (KR); SOULBRAIN CO., LTD., Seongnam-si (KR)

( * ) Notice: Subject to any disclaimer, the term of this patent is extended or adjusted under 35 U.S.C. 154(b) by 413 days.

(21) Appl. No.: 16/726,536

(22) Filed: Dec. 24, 2019

(65) Prior Publication Data
US 2020/0199149 A1    Jun. 25, 2020

(30) Foreign Application Priority Data
Dec. 24, 2018  (KR) .................. 10-2018-0168347

(51) Int. Cl.
*H01L 51/00* (2006.01)
*C07D 495/10* (2006.01)
(Continued)

(52) U.S. Cl.
CPC ......... *C07D 495/10* (2013.01); *C07D 401/10* (2013.01); *C07D 405/14* (2013.01);
(Continued)

(58) Field of Classification Search
None
See application file for complete search history.

(56) References Cited

U.S. PATENT DOCUMENTS 9,944,627 B2     4/2018  Wong et al.
2015/0200372 A1*  7/2015  Park ..................... H05B 33/10
                                                    544/212
(Continued)

FOREIGN PATENT DOCUMENTS

CN         106831773 A  *  6/2017  ........... C07D 471/10

OTHER PUBLICATIONS

Woo et al. "Phenazasiline/spiroacridine donor combined with methyl-substituted linkers for efficient deep blue thermally activated delayed fluorescence Emitters." ACS applied materials & interfaces 11, No. 7 (2019): 7199-7207. (Year: 2019).*
(Continued)

*Primary Examiner* — Robert S Loewe
(74) *Attorney, Agent, or Firm* — Birch, Stewart, Kolasch & Birch, LLP

(57) ABSTRACT

Disclosed is an organic compound that includes a fused hetero aromatic moiety of a spiro structure as an electron donor and a triazine moiety as an electron acceptor that is linked to the electron donor via an arylene linker substituted with at least one electron withdrawing group, an organic light emitting diode and an organic light emitting device each of which applies the organic compound into at least one emitting unit. The organic compound enables the organic light emitting diode to increase its luminous efficiency and to improve its color purity.

40 Claims, 11 Drawing Sheets

(51) Int. Cl.
  *C07D 491/107*  (2006.01)
  *C07D 401/10*  (2006.01)
  *C07F 7/08*  (2006.01)
  *C07D 471/14*  (2006.01)
  *C07D 405/14*  (2006.01)
  *C07D 471/10*  (2006.01)
  *H01L 51/50*  (2006.01)

(52) U.S. Cl.
  CPC ......... *C07D 471/10* (2013.01); *C07D 471/14* (2013.01); *C07D 491/107* (2013.01); *C07F 7/0816* (2013.01); *H01L 51/0052* (2013.01); *H01L 51/0067* (2013.01); *H01L 51/0072* (2013.01); *H01L 51/0073* (2013.01); *H01L 51/0074* (2013.01); *H01L 51/0094* (2013.01); *H01L 51/5004* (2013.01); *H01L 51/5024* (2013.01); *H01L 2251/552* (2013.01)

(56) References Cited

U.S. PATENT DOCUMENTS

| | | | | |
|---|---|---|---|---|
| 2016/0372681 | A1* | 12/2016 | Parham | H01L 51/0071 |
| 2018/0134686 | A1* | 5/2018 | Bergmann | C07D 403/10 |
| 2019/0194171 | A1* | 6/2019 | Bergmann | H01L 51/0072 |
| 2020/0091436 | A1* | 3/2020 | Sun | C09K 11/06 |
| 2020/0119286 | A1* | 4/2020 | Liaptsis | H01L 51/5028 |

OTHER PUBLICATIONS

Lin et al., "Sky-Blue Organic Light Emitting Diode with 37% External Quantum Efficiency Using Thermally Activated Delayed Fluorescence from Spiroacridine-Triazine Hybrid"., Advanced Materials, 28, 6976-6983, (2016).

* cited by examiner

ORGANIC COMPOUND, ORGANIC LIGHT EMITTING DIODE AND ORGANIC LIGHT EMITTING DEVICE HAVING THE COMPOUND

CROSS-REFERENCE TO RELATED APPLICATIONS

This application claims the benefit under 35 U.S.C. § 119(a) of Korean Patent Application No. 10-2018-0168347, filed in the Republic of Korea on Dec. 24, 2018, which is incorporated herein by reference in its entirety.

BACKGROUND

Technical Field

The present disclosure relates to an organic compound, and more specifically, to an organic compound having enhanced luminous efficiency, an organic light emitting diode and an organic light emitting device including the organic compound.

Description of the Related Art

As display devices have become larger, there exists a need for flat display devices that occupy less space. Among the flat display devices, a display device using an organic light emitting diode (OLED) has come into the spotlight.

In the OLED, when electrical charges are injected into an emission layer between an electron injection electrode (i.e., cathode) and a hole injection electrode (i.e., anode), electrical charges are combined to be paired, and then emit light as the combined electrical charges are disappeared.

The OLED can be formed even on a flexible transparent substrate such as a plastic substrate. In addition, the OLED can be driven at a lower voltage of 10 V or less. Besides, the OLED has relatively low power consumption for driving compared to plasma display panels and inorganic electroluminescent devices, and a color purity thereof is very high. Further, since the OLED can display various colors such as green, blue, red and the like, the OLED display device has attracted a lot of attention as a next-generation display device that can replace a liquid crystal display device (LCD).

BRIEF SUMMARY

Accordingly, the present disclosure is directed to an organic compound, an organic light emitting diode and an organic light emitting device including the organic compound that can reduce one or more of the problems due to the limitations and disadvantages of the related art.

An object of the present disclosure is to provide an organic compound that has enhanced luminous efficiency, and an organic light emitting diode and an organic light emitting device each of which includes the organic compound in an emitting unit.

Another object of the present disclosure is to provide an organic compound with improved color purity, and an organic light emitting diode and an organic light emitting device each of which includes the organic compound in an emitting unit.

Additional features and advantages of the disclosure will be set forth in the description which follows, and in part will be apparent from the description, or may be learned by practice of the disclosure. The objectives and other advantages of the disclosure will be realized and attained by the structure particularly pointed out in the written description and claims hereof as well as the appended drawings.

According to an aspect, the present disclosure provides an organic compound having the following Chemical Formula 1:

Chemical Formula 1

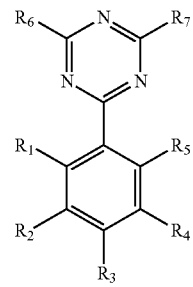

wherein each of $R_1$ to $R_5$ is independently protium, deuterium, tritium, halogen, $C_1 \sim C_{10}$ alkyl halide, cyano group, nitro group or a moiety having the following structure of Chemical Formula 2 or Chemical Formula 3, wherein at least one of $R_1$ to $R_5$ is selected from the group consisting of halogen, $C_1 \sim C_{10}$ alkyl halide, cyano group and nitro group and at least one of $R_1$ to $R_5$ is a moiety of Chemical Formula 2 or Chemical Formula 3; each of $R_6$ and $R_7$ is independently $C_5 \sim C_{30}$ aryl group or $C_4 \sim C_{30}$ hetero aryl group:

Chemical Formula 2

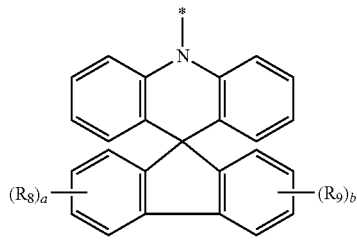

Chemical Formula 3

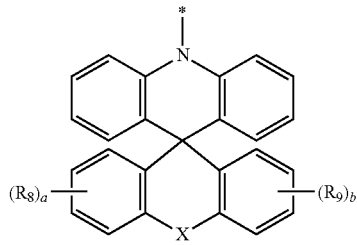

wherein each of $R_8$ and $R_9$ is independently selected from the group consisting of protium, deuterium, tritium, $C_1 \sim C_{20}$ alkyl group, $C_1 \sim C_{20}$ alkoxy group, $C_1 \sim C_{20}$ silyl group, $C_5 \sim C_{30}$ aryl group, $C_4 \sim C_{30}$ hetero aryl group, $C_5 \sim C_{30}$ aryl amino group and $C_4 \sim C_{30}$ hetero aryl amino group, wherein each of the $C_5 \sim C_{30}$ aryl group, the $C_4 \sim C_{30}$ hetero aryl group, the $C_5 \sim C_{30}$ aryl amino group and the $C_4 \sim C_{30}$ hetero aryl amino group is unsubstituted or substituted with an aromatic group, a hetero aromatic group or a combination thereof, respectively; each of a and b is a number of a substituent and is independently an integer of 1 to 3; X in Chemical Formula 3 is $CR_{11}R_{12}$, $NR_{13}$, $SiR_{14}R_{15}$, oxygen (O) or sulfur (S), wherein each of $R_{11}$ to $R_{15}$ is independently selected from the group consisting of protium, deuterium, tritium, $C_1$~$C_{20}$ alkyl group, $C_1$~$C_{20}$ alkoxy group, $C_1$~$C_{20}$ silyl group, $C_5$~$C_{30}$ aryl group and $C_4$~$C_{30}$ hetero aryl group.

According to another aspect, the present disclosure provides an organic light emitting diode (OLED) that comprises a first electrode; a second electrode facing the first electrode; and at least one emitting unit including an emitting material layer disposed between the first and second electrodes, wherein the emitting material layer comprises the above organic compound.

According to still another aspect, the present disclosure provides an organic light emitting device that comprises a substrate and the OLED disposed over the substrate, as described above.

It is to be understood that both the foregoing general description and the following detailed description are examples and are explanatory and are intended to provide further explanation of the disclosure as claimed.

BRIEF DESCRIPTION OF THE DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

DETAILED DESCRIPTION

Figure 1:
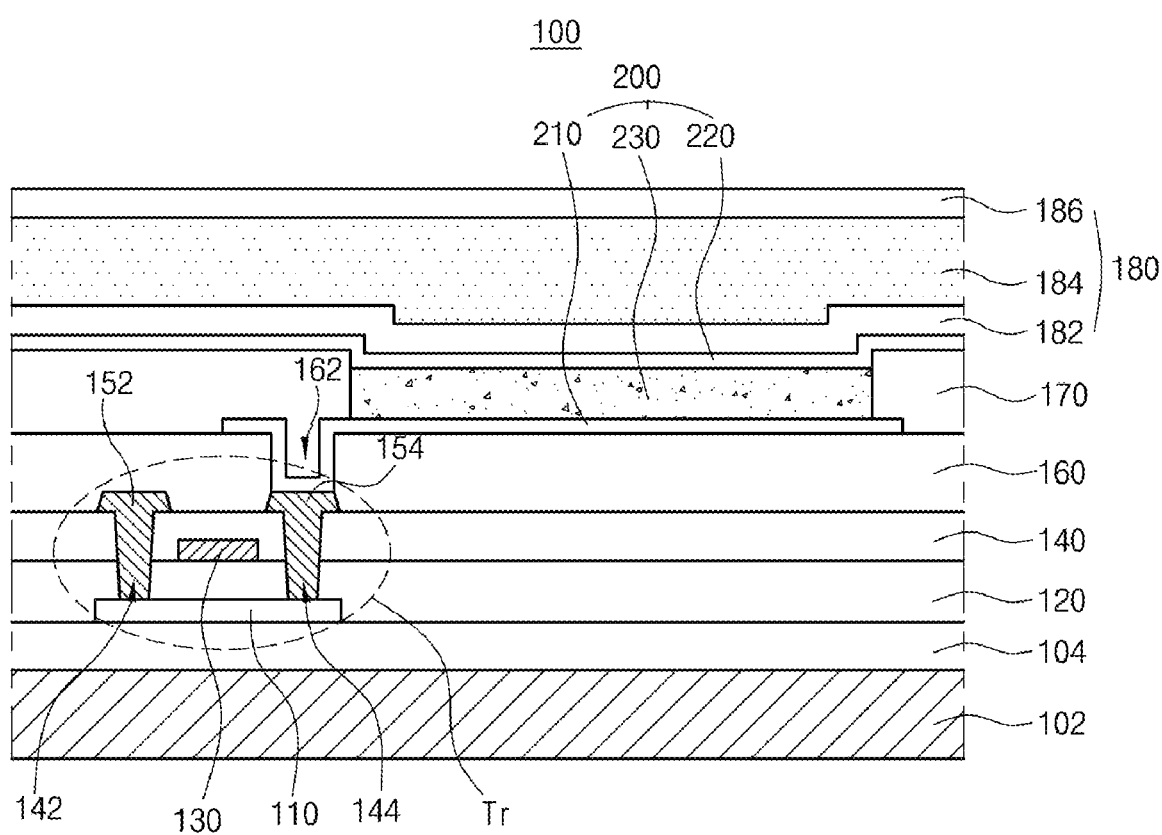
FIG. 1 is a schematic cross-sectional view illustrating an organic light emitting display device of the present disclosure.

Reference will now be made in detail to aspects of the disclosure, examples of which are illustrated in the accompanying drawings.

Organic Compound

An organic compound included in an organic light emitting diode should have excellent luminous properties and maintain stable properties during driving the diode. An organic compound of the present disclosure has a fused hetero aromatic moiety of a spiro structure as an electron donor and a triazine moiety as an electron acceptor which is bonded to the electron donor via an aromatic linker group. The organic compound of the present disclosure has the following structure of Chemical Formula 1:

Chemical Formula 1

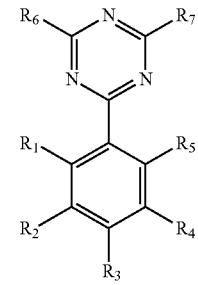

In Chemical Formula 1, each of $R_1$ to $R_5$ is independently protium, deuterium, tritium, halogen, $C_1$~$C_{10}$ alkyl halide, cyano group, nitro group or a moiety having the following structure of Chemical Formula 2 or Chemical Formula 3. At least one of $R_1$ to $R_5$ is selected from the group consisting of halogen, $C_1$~$C_{10}$ alkyl halide, cyano group and nitro group. At least one of $R_1$ to $R_5$ is a moiety of Chemical Formula 2 or Chemical Formula 3. Each of $R_6$ and $R_7$ is independently $C_5$~$C_{30}$ aryl group or $C_4$~$C_{30}$ hetero aryl group:

Chemical Formula 2

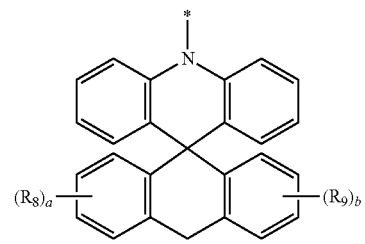

Chemical Formula 3

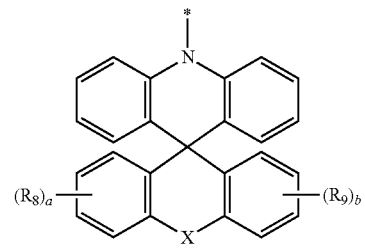

In Chemical Formulae 2 and 3, each of $R_8$ and $R_9$ is independently selected from the group consisting of protium, deuterium, tritium, $C_1$~$C_{20}$ alkyl group, $C_1$~$C_{20}$ alkoxy group, $C_1\sim C_{20}$ silyl group, $C_5\sim C_{30}$ aryl group, $C_4\sim C_{30}$ hetero aryl group, $C_5\sim C_{30}$ aryl amino group and $C_4\sim C_{30}$ hetero aryl amino group, wherein each of the $C_5\sim C_{30}$ aryl group, the $C_4\sim C_{30}$ hetero aryl group, the $C_5\sim C_{30}$ aryl amino group and the $C_4\sim C_{30}$ hetero aryl amino group is unsubstituted or substituted with an aromatic group, a hetero aromatic group or a combination thereof, respectively. Each of a and b is a number of a substituent and is independently an integer of 1 to 3. X in Chemical Formula 3 is $CR_{11}R_{12}$, $NR_{13}$, $SiR_{14}R_{15}$, oxygen (O) or sulfur (S), wherein each of $R_{11}$ to $R_{15}$ is independently selected from the group consisting of protium, deuterium, tritium, $C_1\sim C_{20}$ alkyl group, $C_1\sim C_{20}$ alkoxy group, $C_1\sim C_{20}$ silyl group, $C_5\sim C_{30}$ aryl group and $C_4\sim C_{30}$ hetero aryl group.

As used herein, the term "unsubstituted" means that hydrogen atom is bonded, and in this case hydrogen atom includes protium, deuterium and tritium.

As used herein the term "substituent" may include, but is not limited to, $C_1\sim C_{20}$ alkyl group unsubstituted or substituted with halogen, $C_1\sim C_{20}$ alkoxy group unsubstituted or substituted with halogen, halogen, cyano group, —$CF_3$, hydroxyl group, carboxyl group, carbonyl group, amino group, $C_1\sim C_{20}$ alkyl amino group, $C_5\sim C_{30}$ aryl amino group, $C_4\sim C_{30}$ hetero aryl amino group, nitro group, hydrazyl group, sulfonyl group, $C_5\sim C_{30}$ alkyl silyl group, $C_5\sim C_{30}$ alkoxy silyl group, $C_3\sim C_{30}$ cycloalkyl silyl group, $C_5\sim C_{30}$ aryl silyl group, $C_4\sim C_{30}$ hetero aryl silyl group, $C_5\sim C_{30}$ aryl group and $C_4\sim C_{30}$ hetero aryl group. As an example, when each of $R_1$ to $R_6$ is independently substituted with alkyl group, the alkyl group may be linear or branched $C_1\sim C_{20}$ alkyl group, and preferably linear or branched $C_1\sim C_{10}$ alkyl group.

As used herein, the term "hetero" described in "hetero aromatic ring", "hetero aromatic group", "hetero alicyclic ring", "hetero cyclic alkyl group", "hetero aryl group", "hetero aralkyl group", "hetero aryloxyl group", "hetero aryl amino group", "hetero arylene group", "hetero aralkylene group", "hetero aryloxylene group", and the like means that at least one carbon atoms, for example 1 to 5 carbon atoms, forming such aromatic or alicyclic rings are substituted with at least one hetero atoms selected from the group consisting of N, O, S and combination thereof.

In one exemplary embodiment, when each of $R_6$ and $R_7$ in Chemical Formula 1, $R_8$, $R_9$ and $R_{11}$ to $R_{15}$ in Chemical Formulae 2 and 3 and an aromatic group substituted with those groups is an aromatic substituent such as $C_5\sim C_{30}$ aryl group, the aromatic substituent may independently include, but is not limited to, unfused or fused aryl group such as phenyl, biphenyl, terphenyl, naphthyl, anthracenyl, pentalenyl, indenyl, indeno-indenyl, heptaleneyl, biphenylenyl, indacenyl, phenalenyl, phenanthrenyl, benzo-phenanthrenyl, dibenzo-phenanthrenyl, azulenyl, pyreneyl, fluoranthenyl, triphenylenyl, chrysenyl, tetraphenyl, tetracenyl, pleiadenyl, picenyl, pentaphenyl, pentacenyl, fluorenyl, indeno-fluorenyl or spiro-fluorenyl.

In an alternative embodiment, when each of $R_6$ and $R_7$ in Chemical Formula 1, $R_8$, $R_9$ and $R_{11}$ to $R_{15}$ in Chemical Formulae 2 and 3 and an aromatic group substituted with those groups is a hetero aromatic substituent such as $C_4\sim C_{30}$ hetero aryl group, the hetero aromatic substituent may independently include, but is not limited to, unfused or fused hetero aryl group such as furanyl, thiophenyl, pyrrolyl, pyridinyl, pyrimidinyl, pyrazinyl, pyridazinyl, triazinyl, tetrazinyl, imidazolyl, pyrazolyl, indolyl, carbazolyl, benzo-carbazolyl, dibenzo-carbazolyl, indolo-carbazolyl, indeno-carbazolyl, benzofuro-carbazolyl, benzothieno-carbazolyl, quinolinyl, iso-quinolinyl, phthalazinyl, quinoxalinyl, cinnolinyl, quinazolinyl, benzo-quinolinyl, benzo-iso-quinolinyl, benzo-quinazolinyl, benzo-quinoxalinyl, acridinyl, phenanthrolinyl, phenazinyl, phenoxazinyl, phenothiazinyl, pyranyl, oxazinyl, oxazolyl, iso-oxazolyl, oxadiazolyl, triazolyl, dioxinyl, benzo-furanyl, dibenzo-furanyl, thiopyranyl, thiazinyl, benzo-thiophenyl, dibenzo-thiophenyl, spiroacridinyl connected to a xanthene, dihydro-acridinyl substituted with at least one $C_1\sim C_{10}$ alkyl group and N-substituted spiro-fluorenyl.

The organic compound having the structure of Chemical Formula 1 includes a fused hetero aromatic moiety of spiro structure having a nitrogen atom as an electron donor and a triazine moiety linked to the electron donor moiety via a phenylene linker. As a streric hindrance between the electron donor and the electron acceptor increases, dihedral angles between those moieties increases. As a result, the organic compound can be divided easily into a highest occupied molecular orbital (HOMO) energy state and a lowest unoccupied molecular orbital (LUMO) energy state because the formation of the conjugate structure between those moieties is limited.

In addition, dipoles are formed between the electron donor moiety and the electron acceptor moiety, and the dipole moments within the molecule are increased. Therefore, an organic light emitting diode using the organic compound can enhance its luminous efficiency. Moreover, the organic compound has a limited conformational structure owing to the fused hetero aromatic moiety of the spiro structure with a large steric hindrance. As a result, when the organic compound having the structure of Chemical Formula 1 is laminated, the conformational structure of the organic compound is not changed, so the energy loss during the luminescent process is reduced and the luminescence spectrum of the organic compound can be limited to a specific range to improve its color purity. As the luminous efficiency of an OLED using the organic compound is improved, it is not necessary to increase a driving voltage of the OLED. Moreover, power consumption of the OLED and load applied to the OLED, each of which is increased as the driving voltage, can be reduced, so that the luminous lifetime of the OLED can be increased.

In one exemplary embodiment, the organic compound having the structure of Chemical Formula 1 may have one cyano group on the central phenylene linker. Such an organic compound may have the following structure of Chemical Formula 4:

Chemical Formula 4

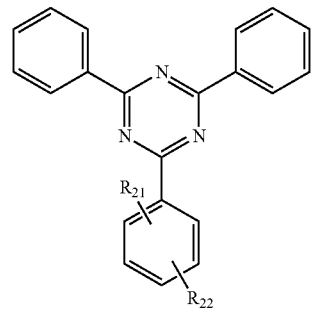

In Chemical Formula 4, $R_{21}$ is cyano group. $R_{22}$ is a moiety having the following structure of Chemical Formula 5 or Chemical Formula 6:

Chemical Formula 5

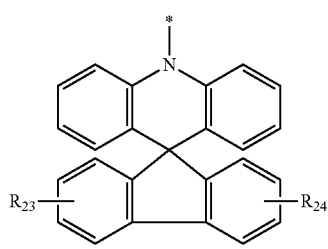

Chemical Formula 6

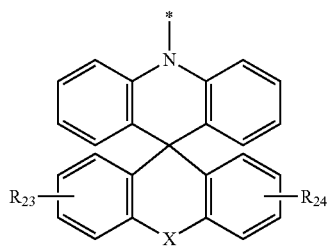

In Chemical Formulae 5 and 6, each of $R_{23}$ and $R_{24}$ is independently selected from the group consisting of protium, deuterium, tritium, $C_1$~$C_{20}$ alkyl group, $C_5$~$C_{30}$ aryl group unsubstituted or substituted with aromatic group, hetero aromatic group or combination thereof and $C_4$~$C_{30}$ hetero aryl group unsubstituted or substituted with aromatic group, hetero aromatic group or combination thereof. X in Chemical Formula 6 is $CR_{11}R_{12}$, $NR_{13}$, $SiR_{14}R_{15}$, oxygen (O) or sulfur (S), wherein each of $R_{11}$ to $R_{15}$ is independently selected from the group consisting of protium, deuterium, tritium, $C_1$~$C_{20}$ alkyl group, $C_1$~$C_{20}$ alkoxy group, $C_1$~$C_{20}$ silyl group, $C_5$~$C_{30}$ aryl group and $C_4$~$C_{30}$ hetero aryl group.

Particularly, the organic compound having one cyano group on the phenylene linker may have any one of the following structures of Chemical Formula 7.

Chemical Formula 7

Compound 1-1

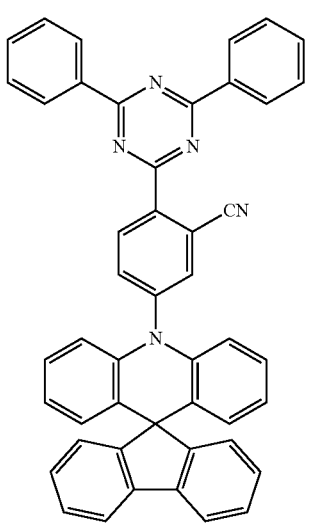

Compound 1-2

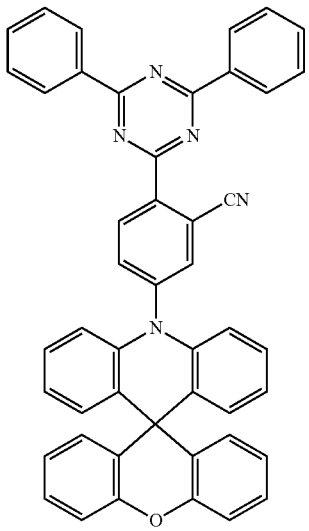

Compound 1-3

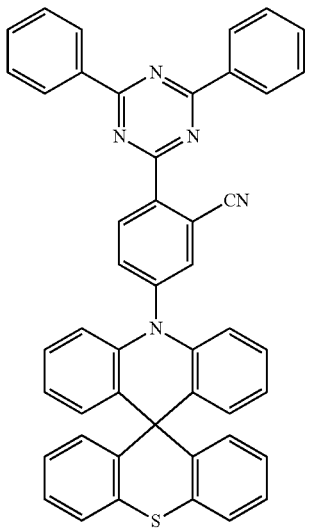

-continued
Compound 1-4
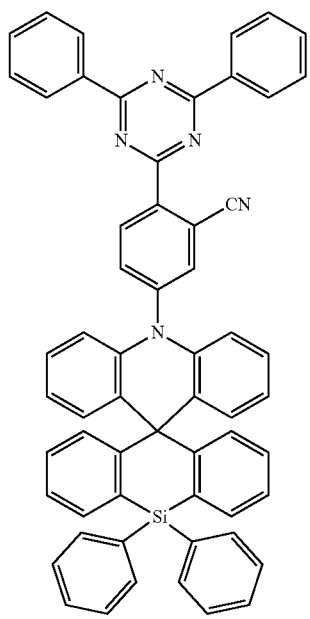
Compound 1-5
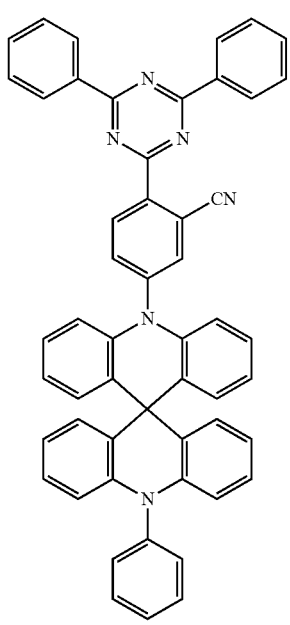
Compound 1-6
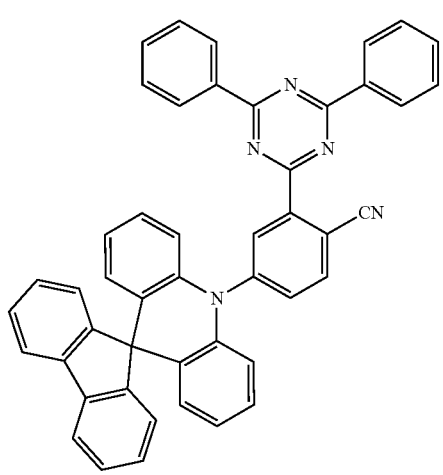
Compound 1-7
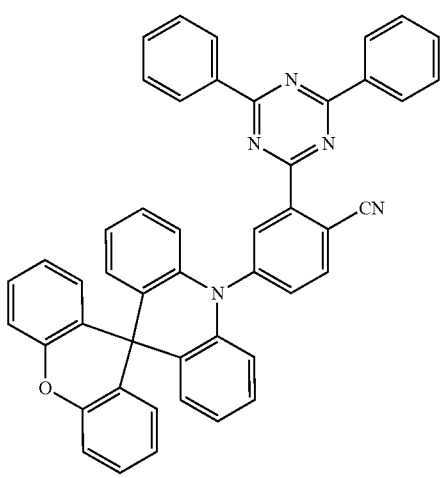
Compound 1-8
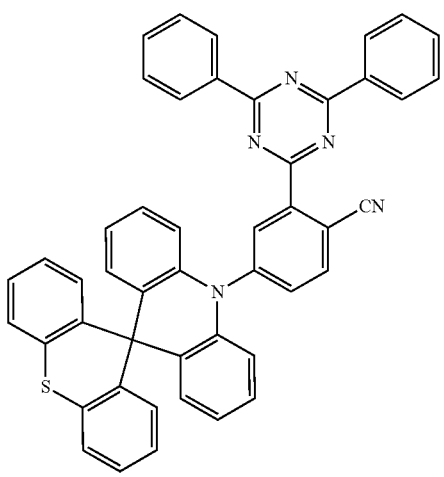

Compound 1-9
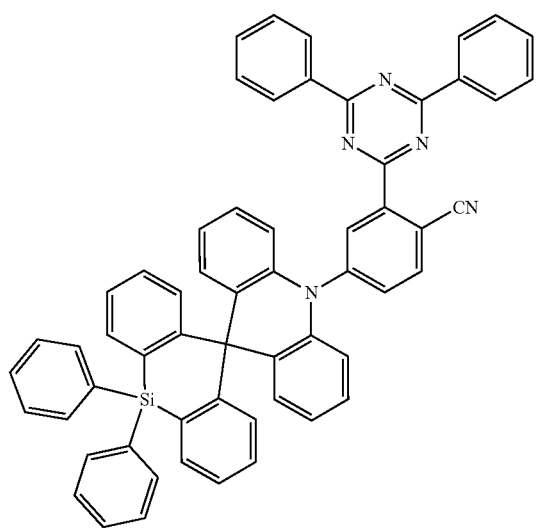
Compound 1-12
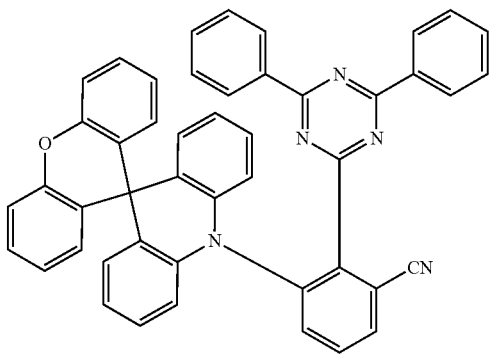
Compound 1-13
Compound 1-10
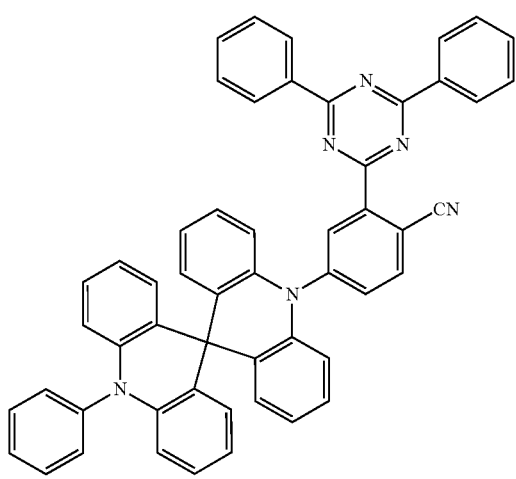
Compound 1-14
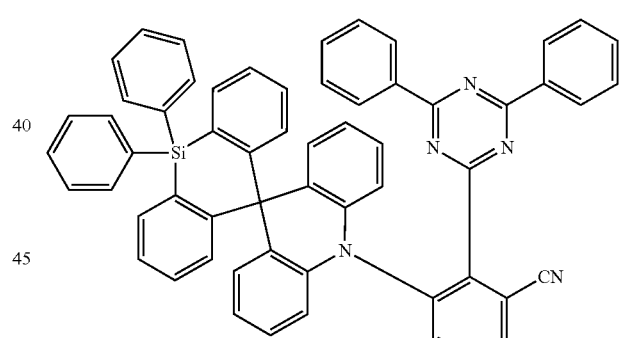
Compound 1-11
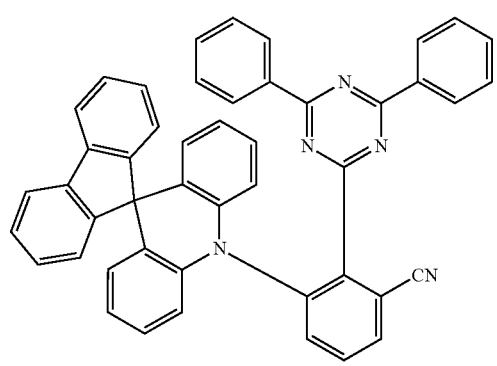
Compound 1-15
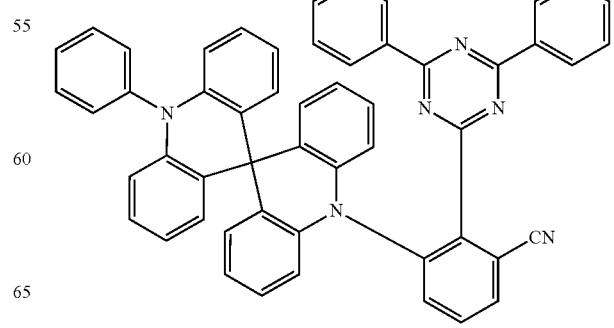

Compound 1-16
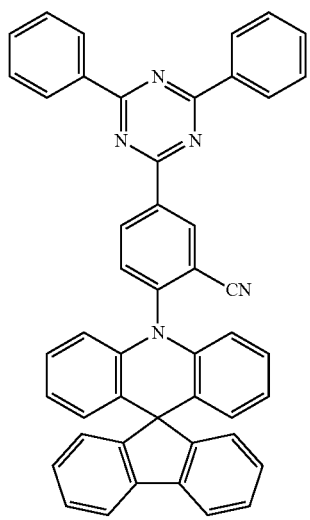
Compound 1-17
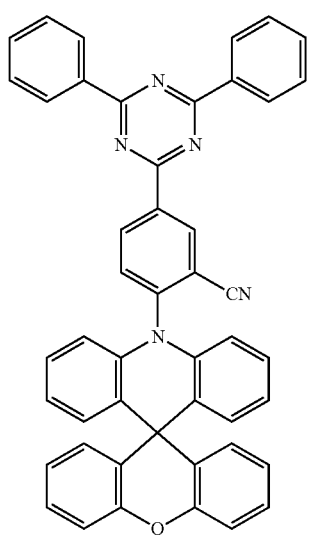
Compound 1-18
Compound 1-19
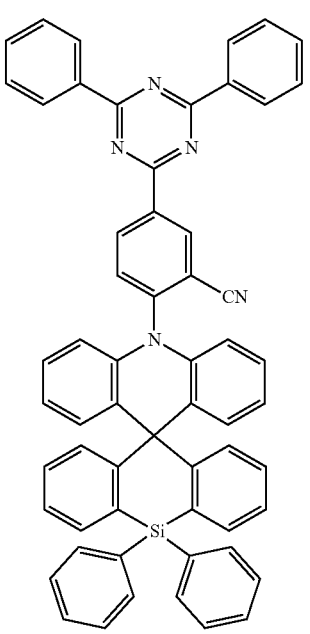
Compound 1-20
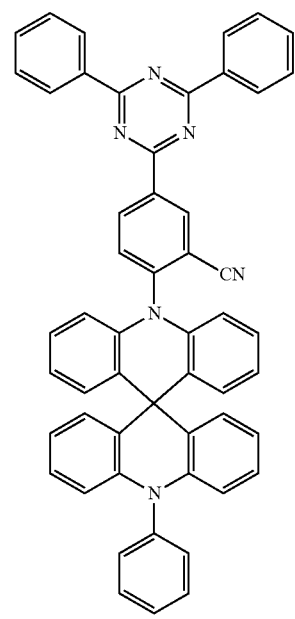

Compound 1-21
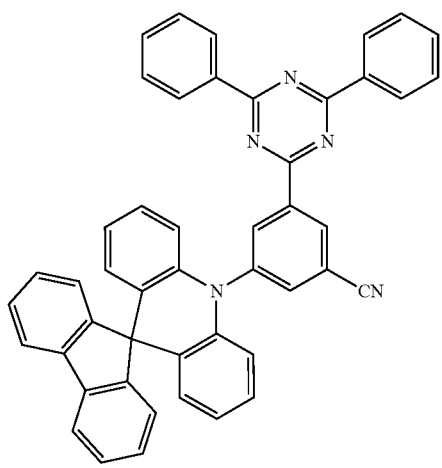
Compound 1-22
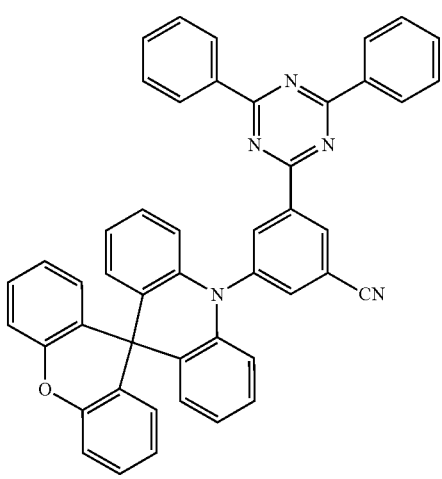
Compound 1-23
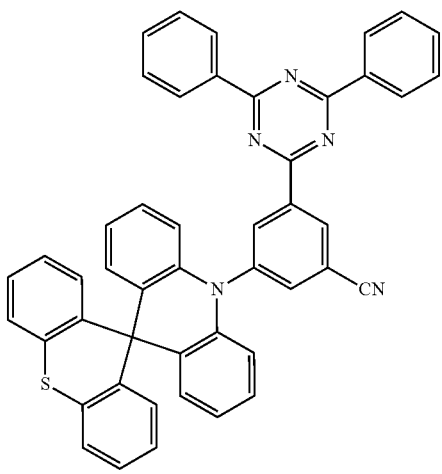
Compound 1-24
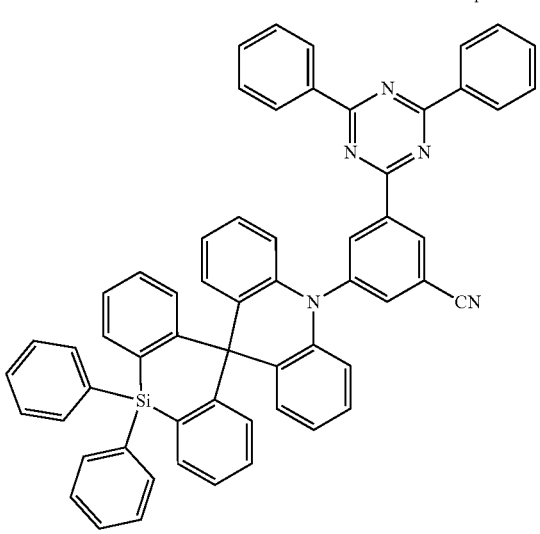
Compound 1-25
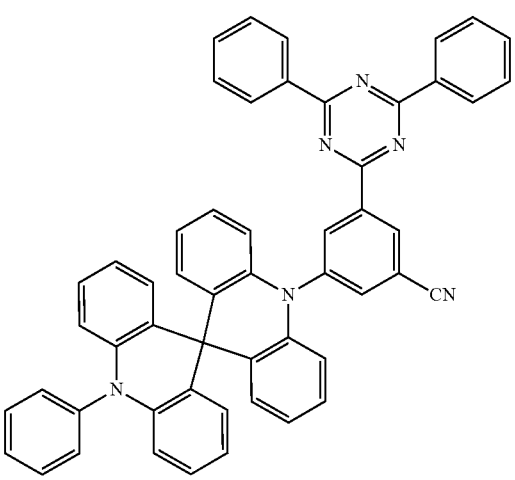
Compound 1-26
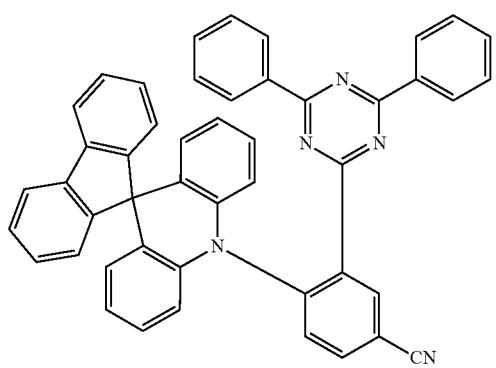

Compound 1-27
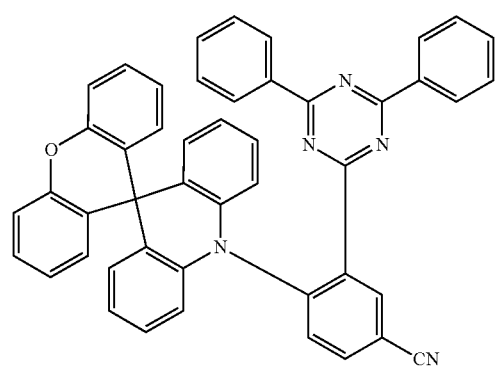
Compound 1-28
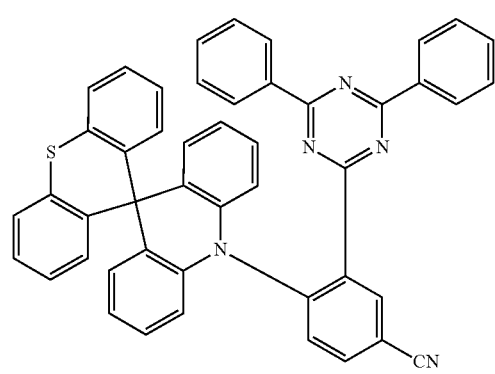
Compound 1-29
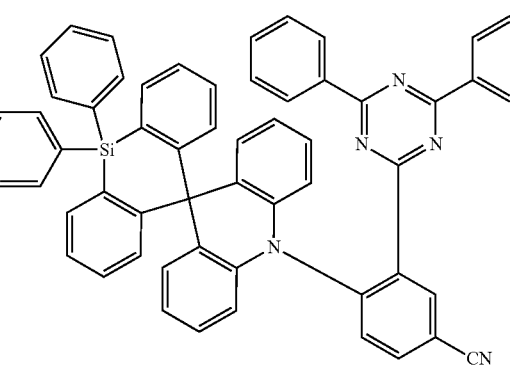
Compound 1-30
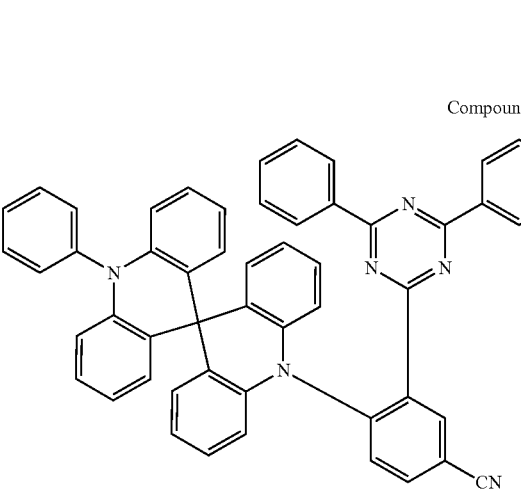
Compound 1-31
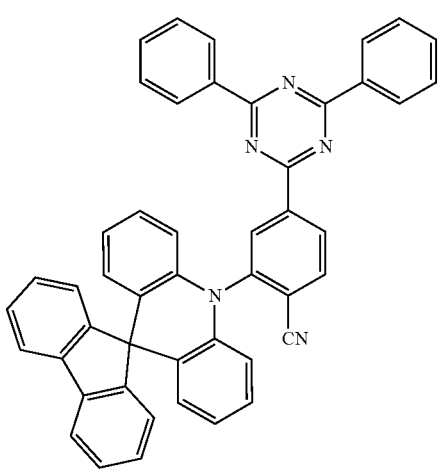
Compound 1-32
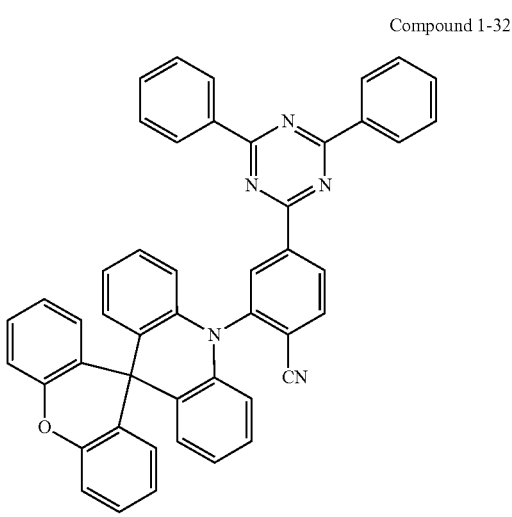
Compound 1-33
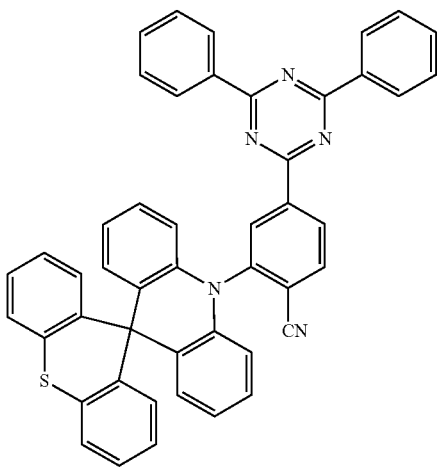

Compound 1-34
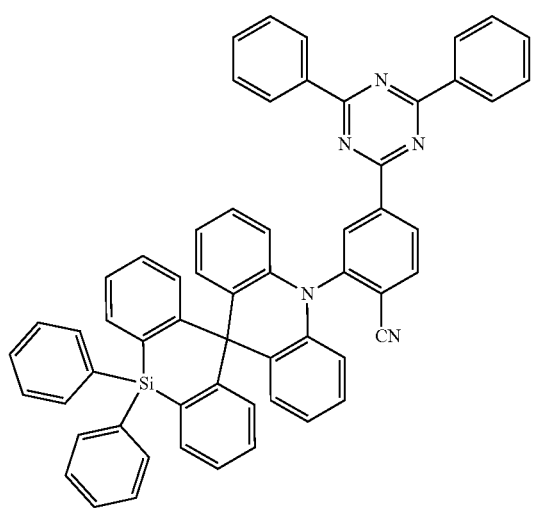
Compound 1-35
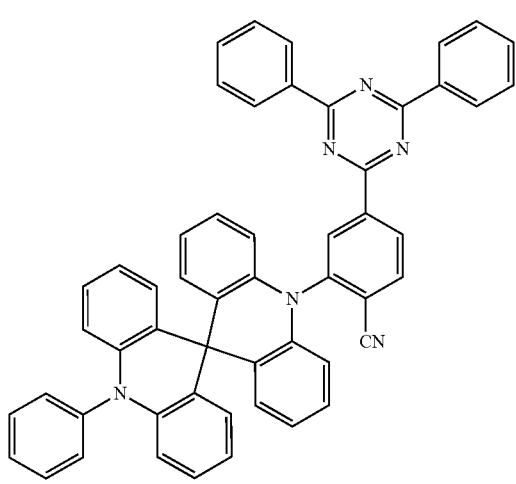
Compound 1-36
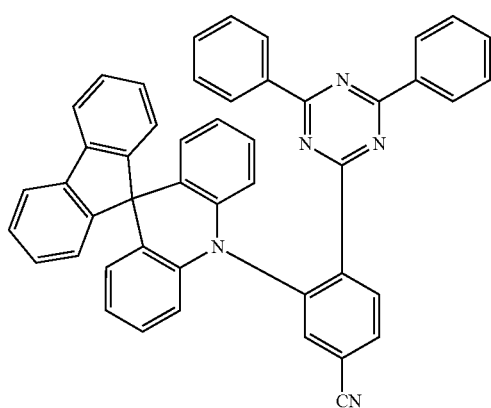
Compound 1-37
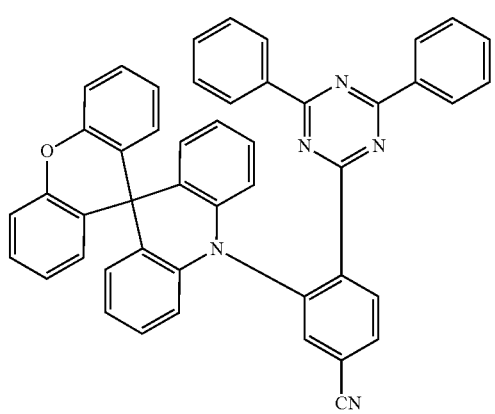
Compound 1-38
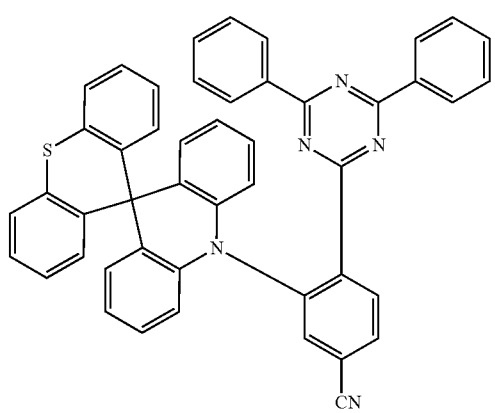
Compound 1-39
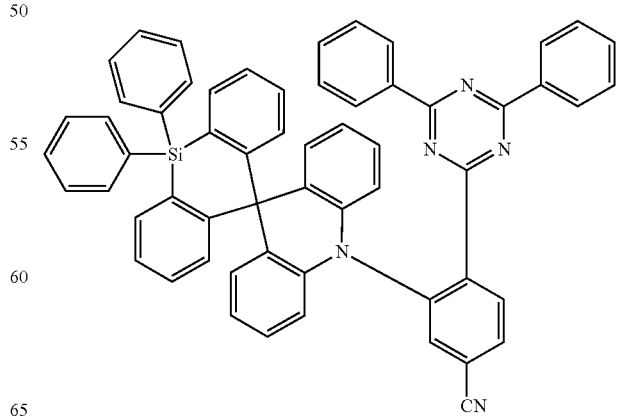

-continued
Compound 1-40
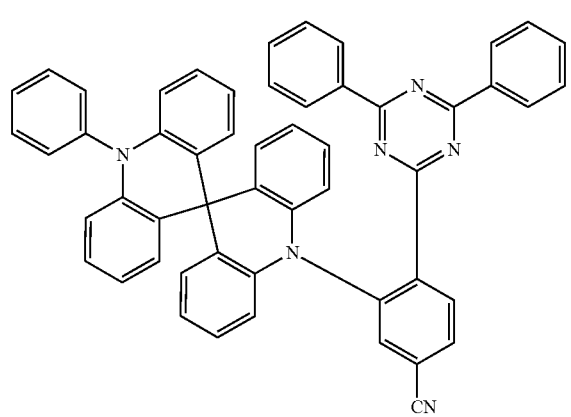
Compound 1-41
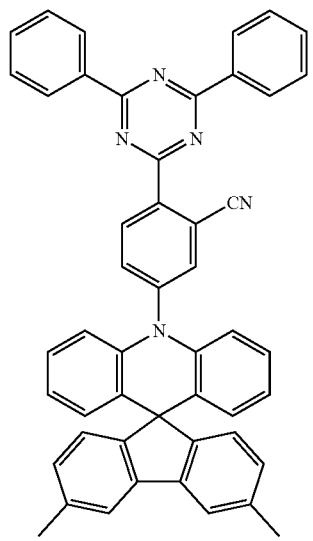
Compound 1-42
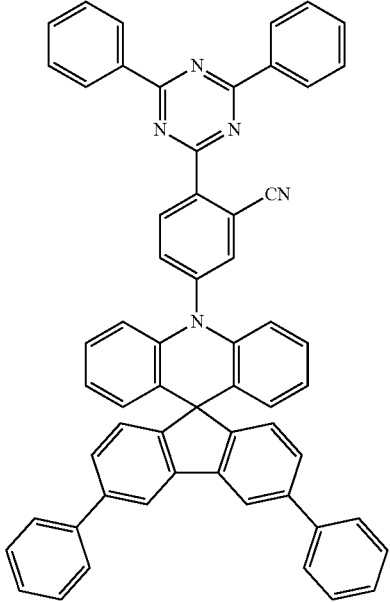
Compound 1-43
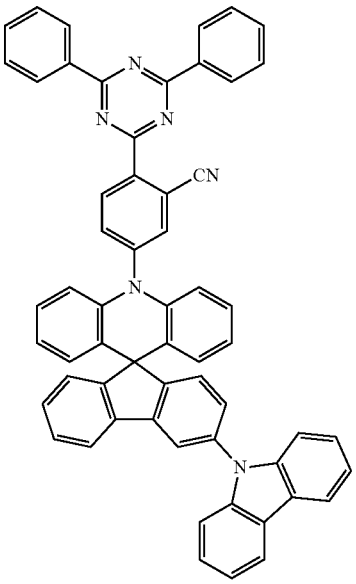
Compound 1-44
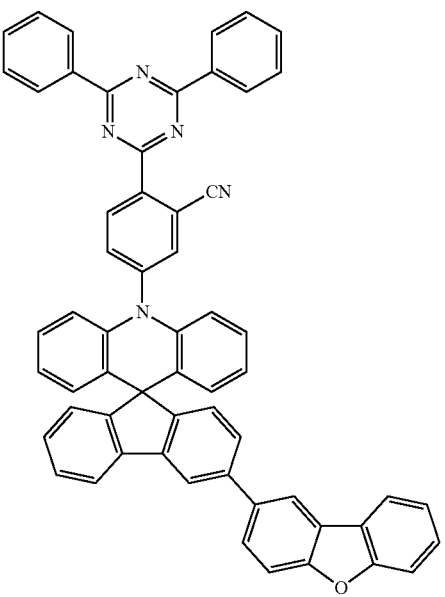

-continued
Compound 1-45
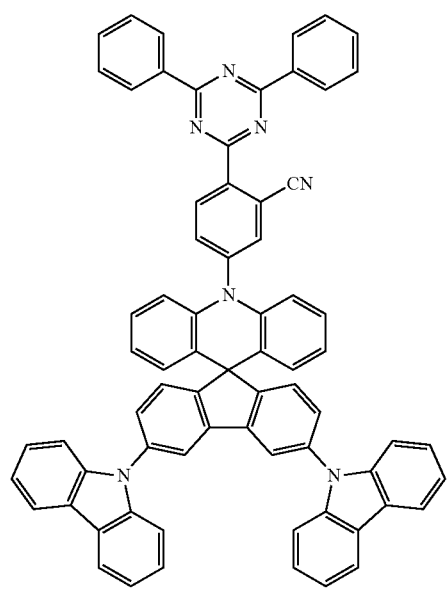
Compound 1-46
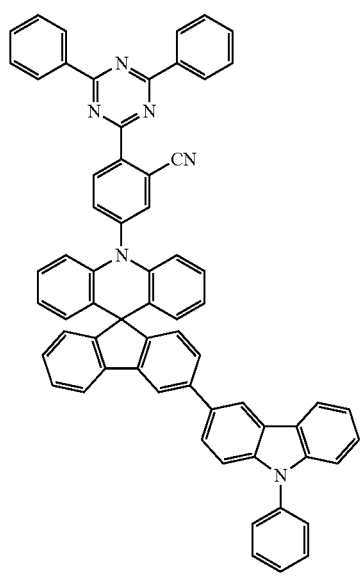
-continued
Compound 1-47
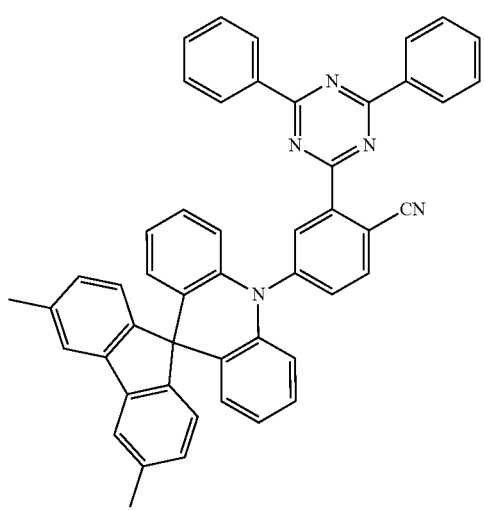
Compound 1-48
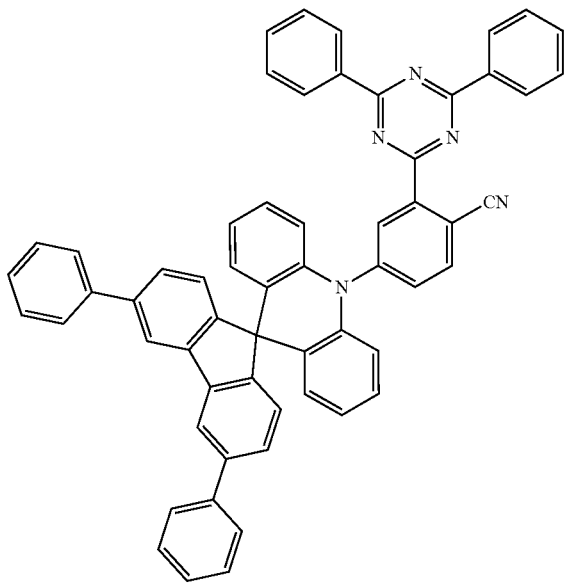

Compound 1-49
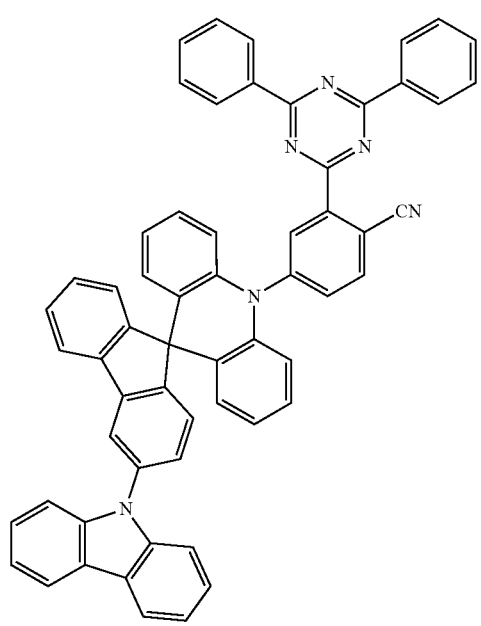
Compound 1-51
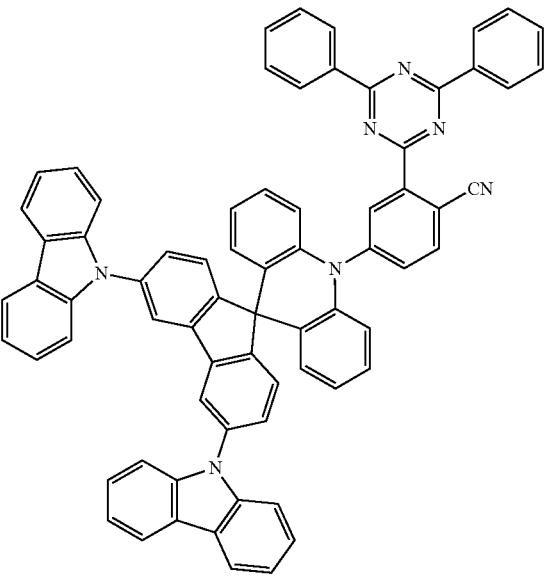
Compound 1-50
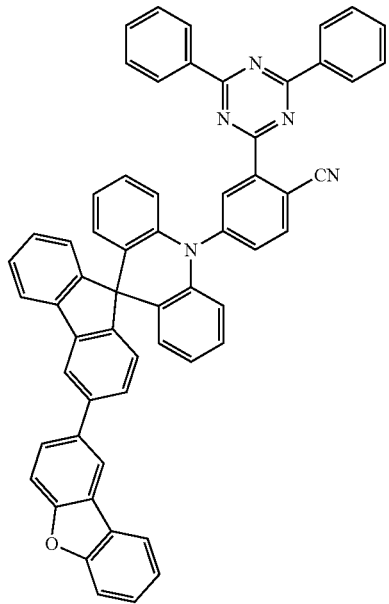
Compound 1-52
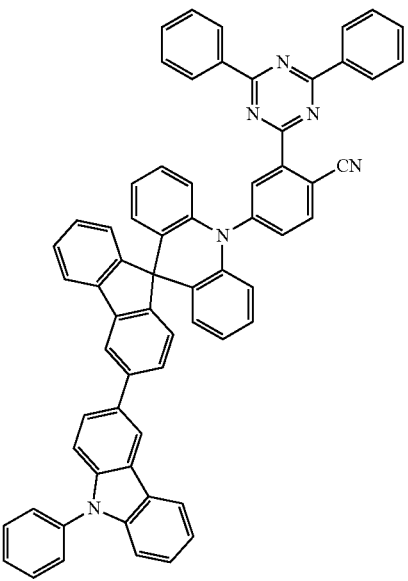

Compound 1-53
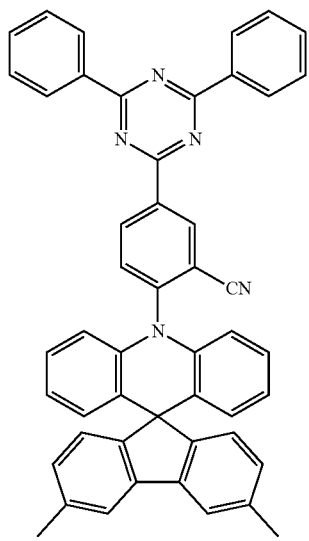
Compound 1-55
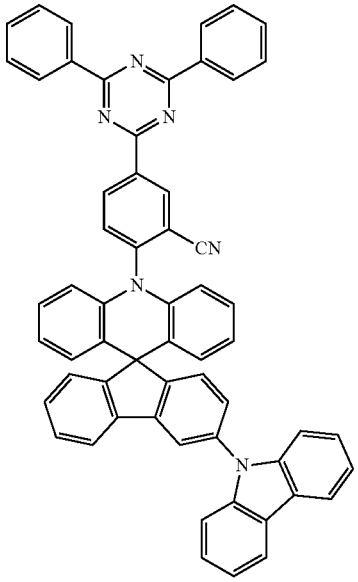
Compound 1-54
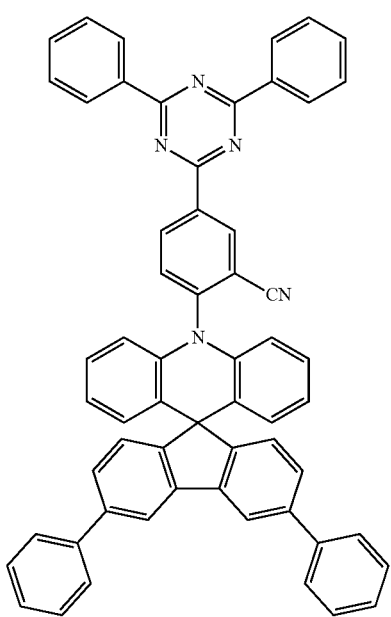
Compound 1-56
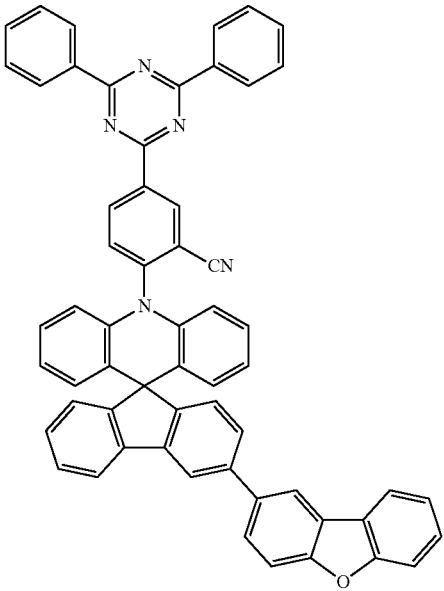

Compound 1-57
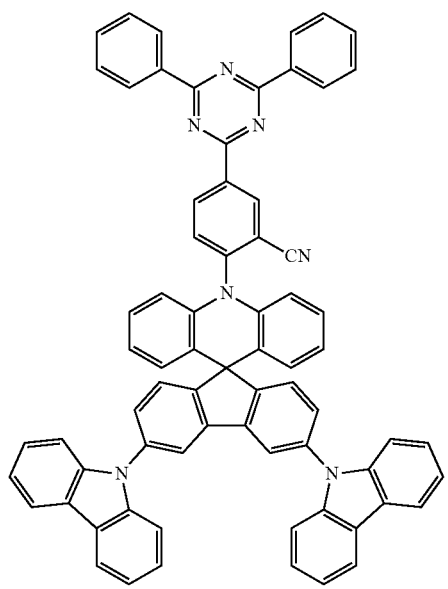
Compound 1-58
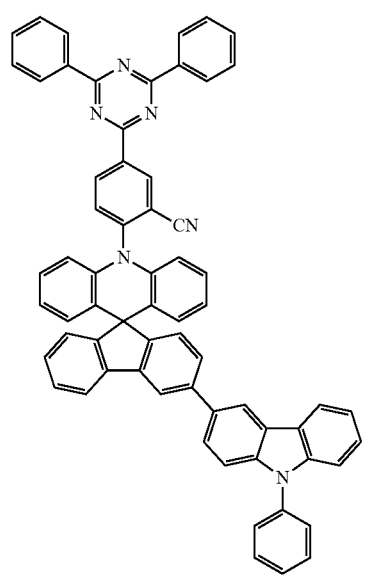
Compound 1-59
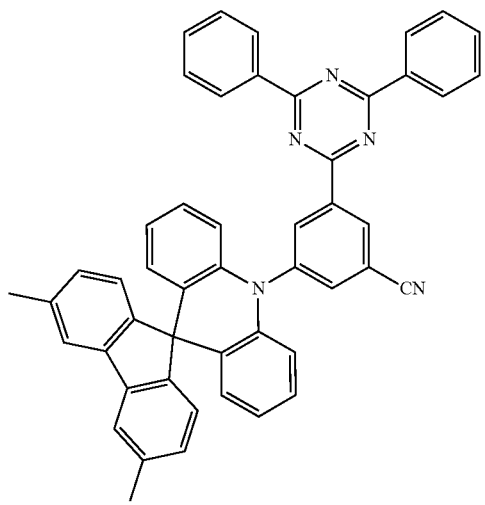
Compound 1-60
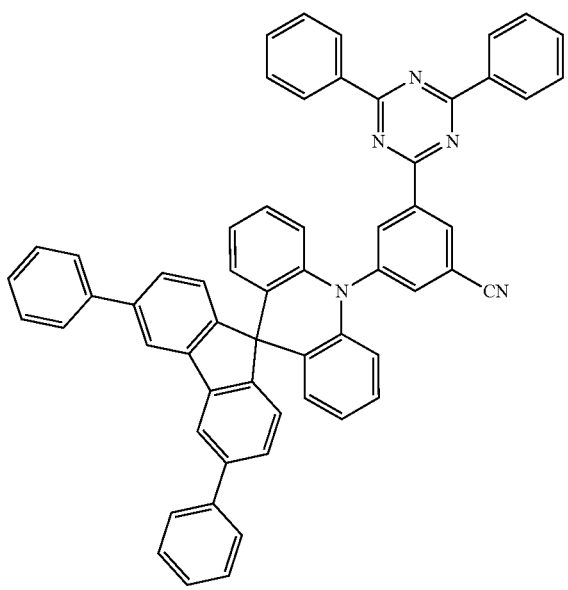

-continued
Compound 1-61
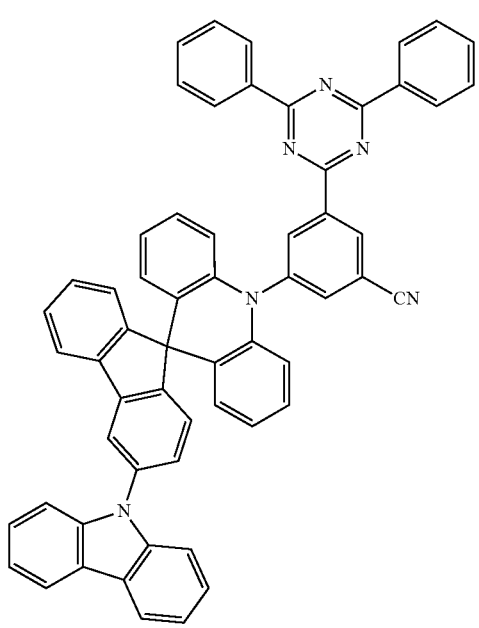
Compound 1-62
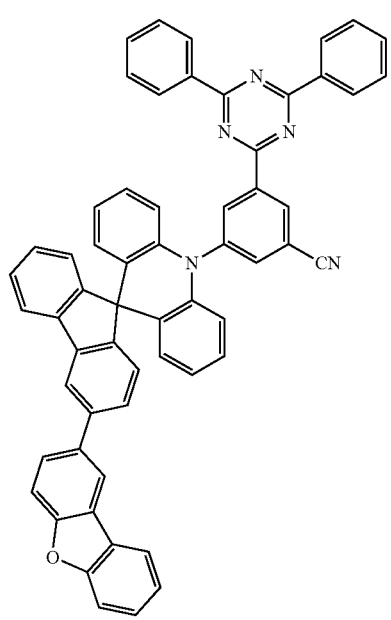
-continued
Compound 1-63
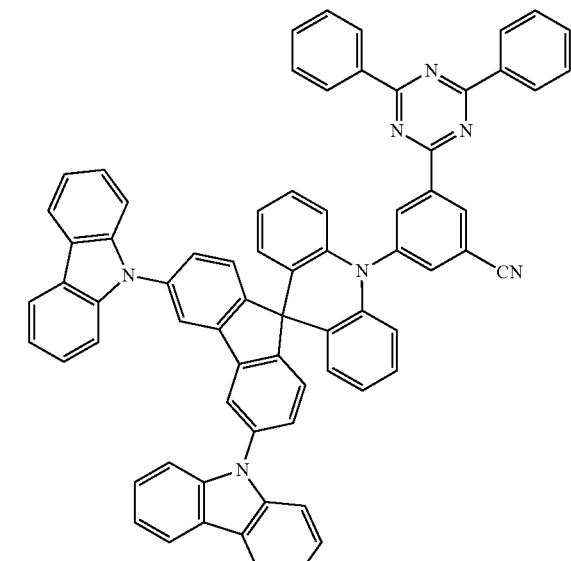
Compound 1-64
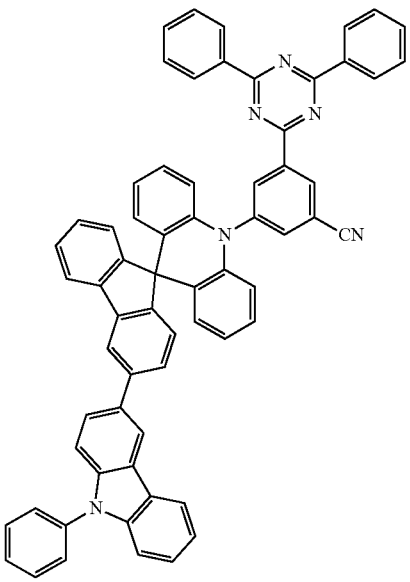
In another exemplary embodiment, the organic compound having the structure of Chemical Formula 1 may have two cyano groups on the central phenylene linker. Such an organic compound may have the following structure of Chemical Formula 8:

Chemical Formula 8

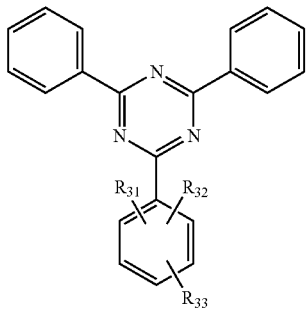

In Chemical Formula 8, each of $R_{31}$ and $R_{32}$ is cyano group. $R_{33}$ is a moiety having the following structure of Chemical Formula 9 or Chemical Formula 10:

Chemical Formula 9

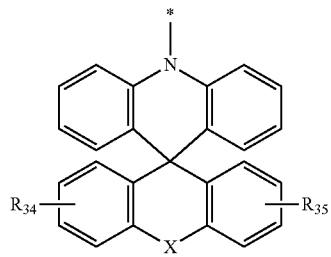

Chemical Formula 10

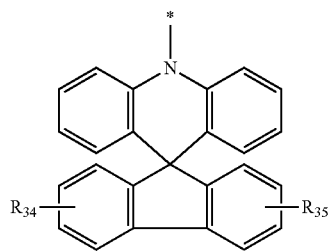

In Chemical Formulae 9 and 10, each of $R_{34}$ and $R_{35}$ is independently selected from the group consisting of protium, deuterium, tritium, $C_1$~$C_{20}$ alkyl group, $C_5$~$C_{30}$ aryl group unsubstituted or substituted with aromatic group, hetero aromatic group or combination thereof and $C_4$~$C_{30}$ hetero aryl group unsubstituted or substituted with aromatic group, hetero aromatic group or combination thereof. X in Chemical Formula 9 is $CR_{11}R_{12}$, $NR_{13}$, $SiR_{14}R_{15}$, oxygen (O) or sulfur (S), wherein each of $R_{11}$ to $R_{15}$ is independently selected from the group consisting of protium, deuterium, tritium, $C_1$~$C_{20}$ alkyl group, $C_1$~$C_{20}$ alkoxy group, $C_1$~$C_{20}$ silyl group, $C_5$~$C_{30}$ aryl group and $C_4$~$C_{30}$ hetero aryl group.

Particularly, the organic compound having two cyano groups on the phenylene linker may have any one of the following structures of Chemical Formula 11.

Chemical Formula 11

Compound 2-1

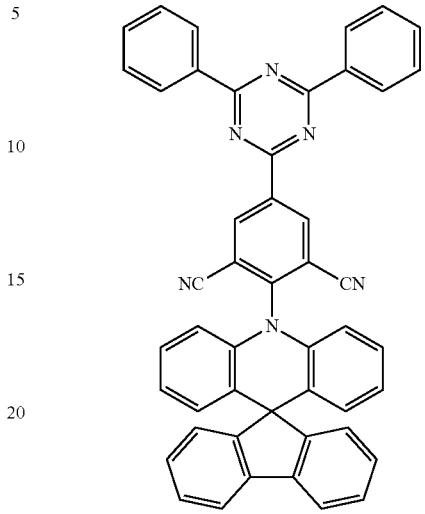

Compound 2-2

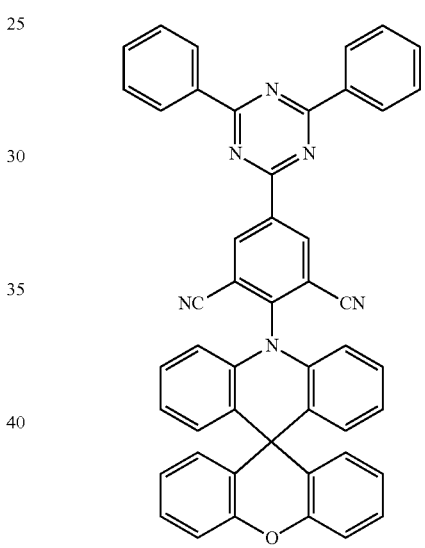

Compound 2-3

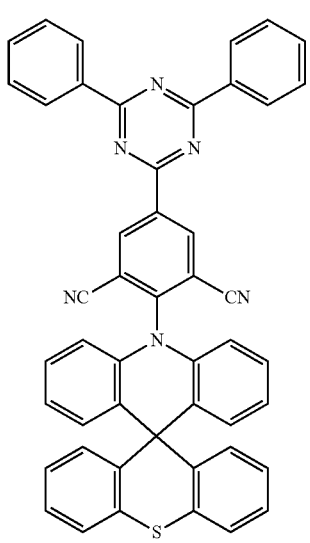

Compound 2-4
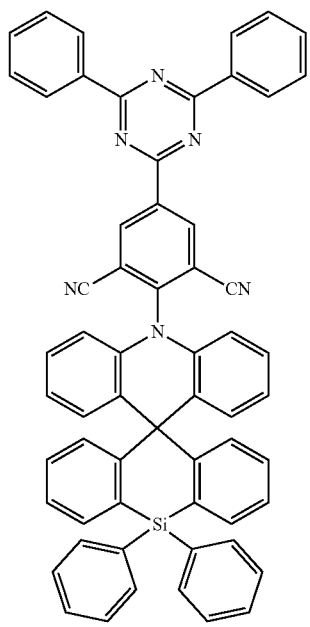
Compound 2-5
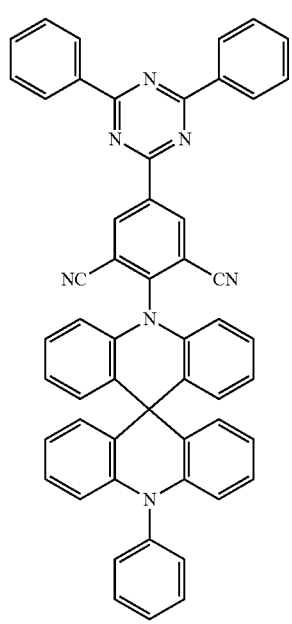
Compound 2-6
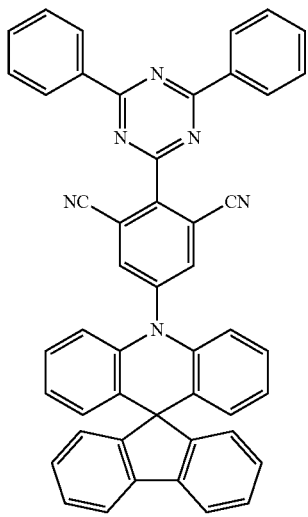
Compound 2-7
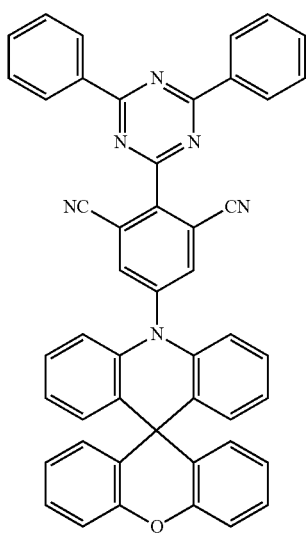
Compound 2-8
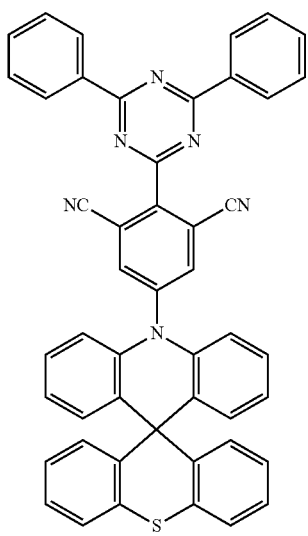

Compound 2-9
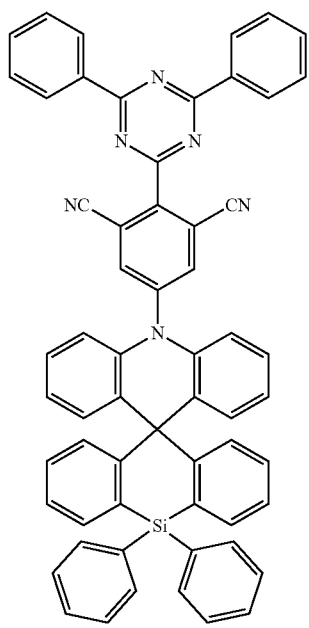
Compound 2-10
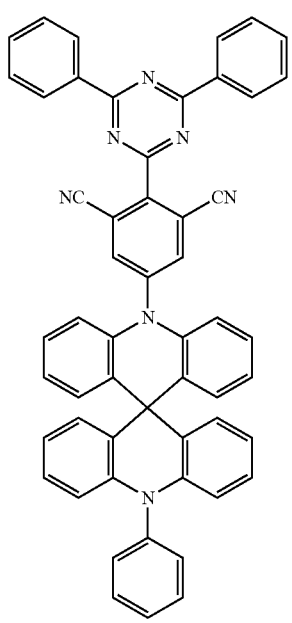
Compound 2-11
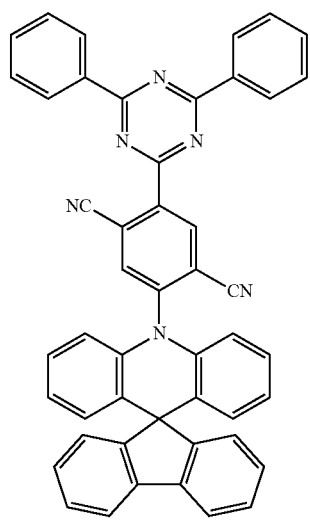
Compound 2-12
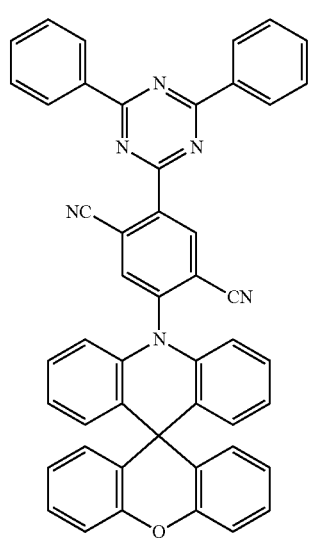
Compound 2-13

Compound 2-14
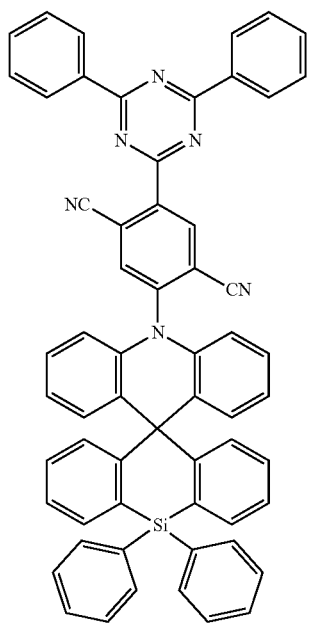
Compound 2-16
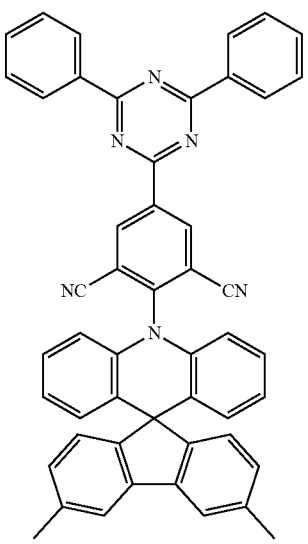
Compound 2-15
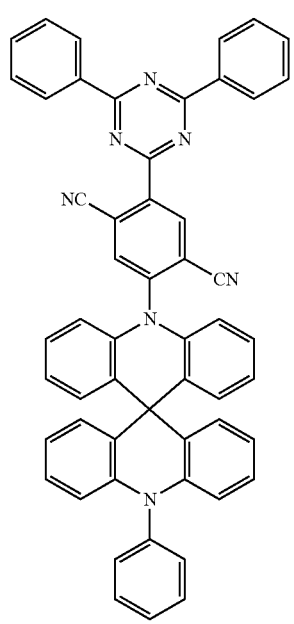
Compound 2-17
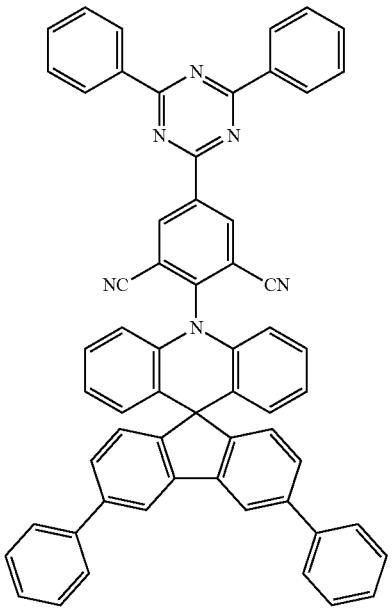

Compound 2-18
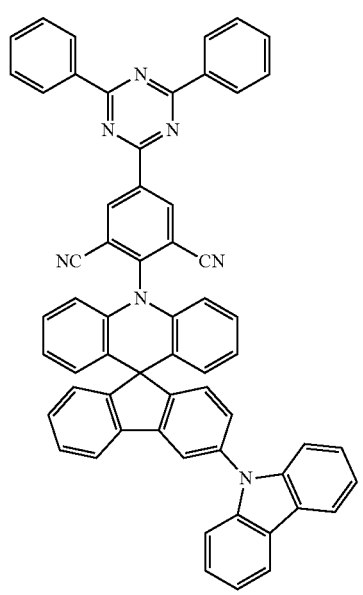
Compound 2-20
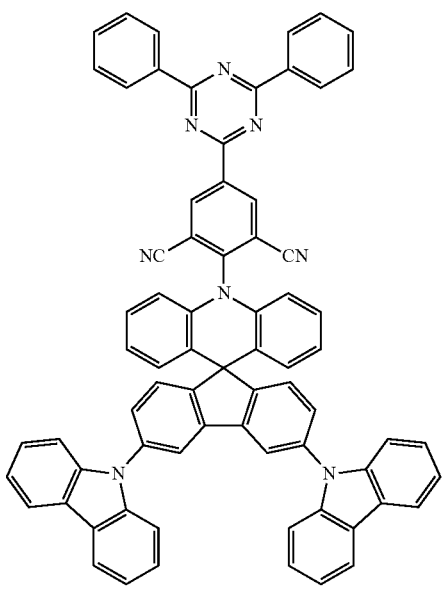
Compound 2-19
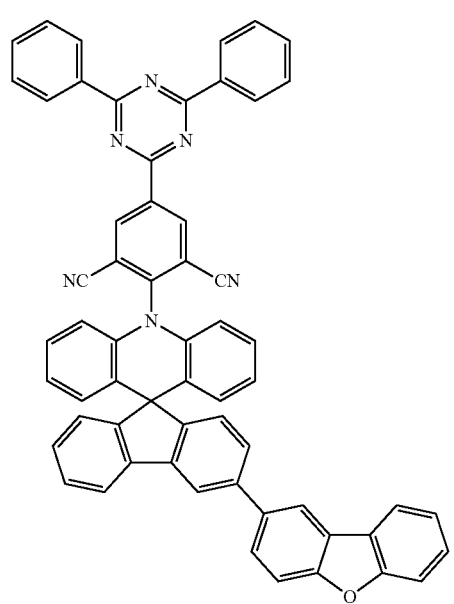
Compound 2-21
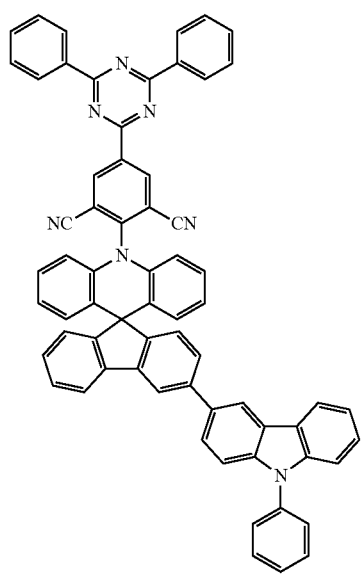

Compound 2-22
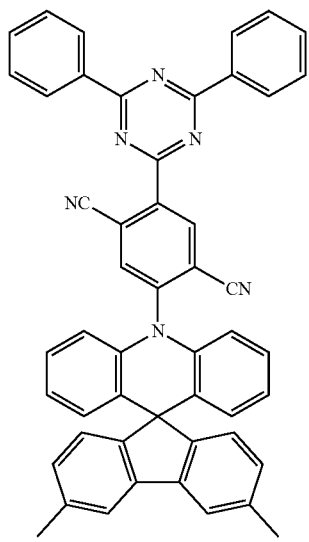
Compound 2-24
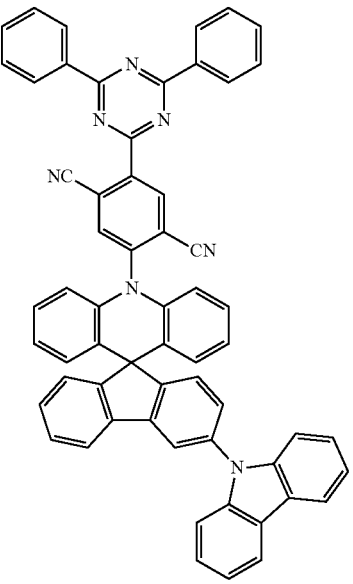
Compound 2-23
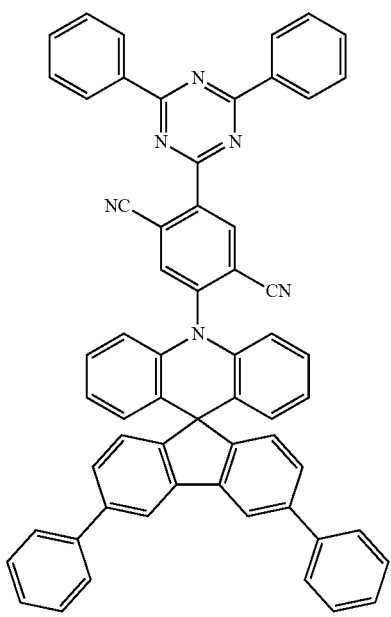
Compound 2-25
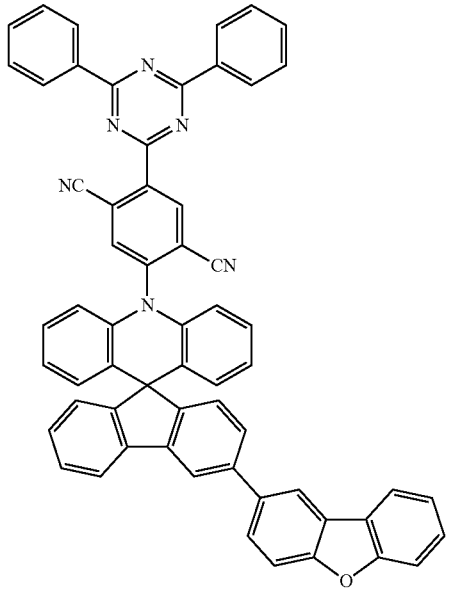

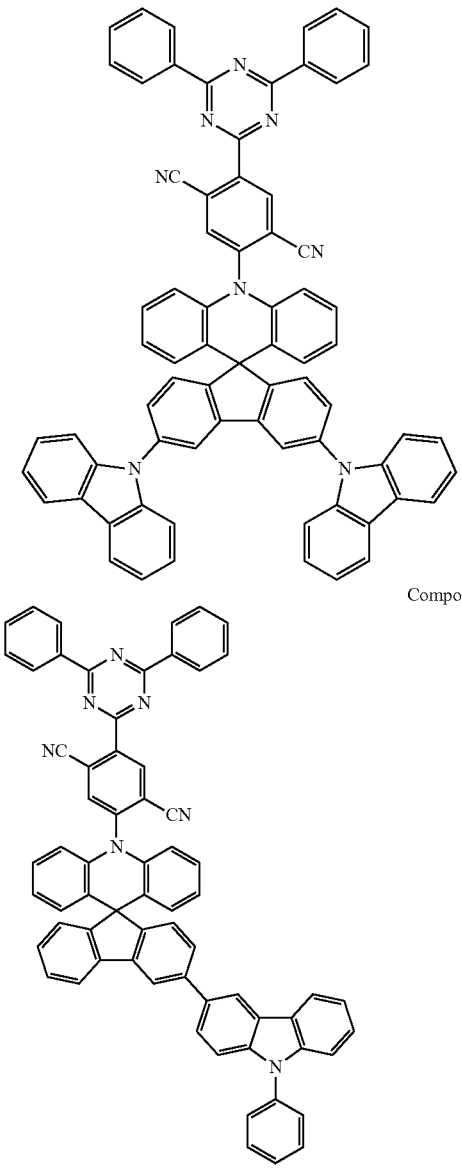

Compound 2-26

Compound 2-27

[Organic Light Emitting Device]

The organic compound having the structure of any one in Chemical Formulae 1, 4, 7, 8 and 11 has a delayed fluorescent property owing to co-existence of the electron donor moiety and the electron acceptor moiety within the molecule. The organic compound having the structure of any one in Chemical Formulae 1, 4, 7, 8 and 11 may be applied to an emitting material layer of an organic light emitting diode so as to implement an organic light emitting element having enhanced luminous efficiency and lower driving voltage.

The organic light emitting diode of the present disclosure may be applied to an organic light emitting device such as an organic light emitting display device and an organic light emitting illumination device. An organic light emitting display device will be explained. FIG. 1 is a schematic cross-sectional view of an organic light emitting display device in accordance with an exemplary embodiment of the present disclosure.

As illustrated in FIG. 1, the organic light emitting display device 100 includes a substrate 102, a thin-film transistor Tr on the substrate 102, and an organic light emitting diode 200 connected to the thin film transistor Tr.

The substrate 102 may include, but is not limited to, glass, thin flexible material and/or polymer plastics. For example, the flexible material may be selected from the group, but is not limited to, polyimide (PI), polyethersulfone (PES), polyethylenenaphthalate (PEN), polyethylene terephthalate (PET), polycarbonate (PC) and combination thereof. The substrate 102, over which The thin film transistor Tr and the organic light emitting diode 200 are arranged, form an array substrate.

A buffer layer 104 may be disposed over the substrate 102, and the thin film transistor Tr is disposed over the buffer layer 104. The buffer layer 104 may be omitted.

A semiconductor layer 110 is disposed over the buffer layer 104. In one exemplary embodiment, the semiconductor layer 110 may include, but is not limited to, oxide semiconductor materials. In this case, a light-shield pattern may be disposed under the semiconductor layer 110, and the light-shield pattern can prevent light from being incident toward the semiconductor layer 110, and thereby, preventing the semiconductor layer 110 from being deteriorated by the light. Alternatively, the semiconductor layer 110 may include, but is not limited to, polycrystalline silicon. In this case, opposite edges of the semiconductor layer 110 may be doped with impurities.

A gate insulating layer 120 formed of an insulating material is disposed on the semiconductor layer 110. The gate insulating layer 120 may include, but is not limited to, an inorganic insulating material such as silicon oxide ($SiO_x$) or silicon nitride ($SiN_x$).

A gate electrode 130 made of a conductive material such as a metal is disposed over the gate insulating layer 120 so as to correspond to a center of the semiconductor layer 110. While the gate insulating layer 120 is disposed over a whole area of the substrate 102 in FIG. 1, the gate insulating layer 120 may be patterned identically as the gate electrode 130.

An interlayer insulating layer 140 formed of an insulating material is disposed on the gate electrode 130 with covering over an entire surface of the substrate 102. The interlayer insulating layer 140 may include, but is not limited to, an inorganic insulating material such as silicon oxide ($SiO_x$) or silicon nitride ($SiN_x$), or an organic insulating material such as benzocyclobutene or photo-acryl.

The interlayer insulating layer 140 has first and second semiconductor layer contact holes 142 and 144 that expose both sides of the semiconductor layer 110. The first and second semiconductor layer contact holes 142 and 144 are disposed over opposite sides of the gate electrode 130 with spacing apart from the gate electrode 130. The first and second semiconductor layer contact holes 142 and 144 are formed within the gate insulating layer 120 in FIG. 1. Alternatively, the first and second semiconductor layer contact holes 142 and 144 are formed only within the interlayer insulating layer 140 when the gate insulating layer 120 is patterned identically as the gate electrode 130.

A source electrode 152 and a drain electrode 154, each of which is made of a conductive material such as a metal, are disposed on the interlayer insulating layer 140. The source electrode 152 and the drain electrode 154 are spaced apart from each other with respect to the gate electrode 130, and contact both sides of the semiconductor layer 110 through the first and second semiconductor layer contact holes 142 and 144, respectively.

The semiconductor layer 110, the gate electrode 130, the source electrode 152 and the drain electrode 154 constitute the thin film transistor Tr, which acts as a driving element. The thin film transistor Tr in FIG. 1 has a coplanar structure in which the gate electrode 130, the source electrode 152 and the drain electrode 154 are disposed over the semiconductor layer 110. Alternatively, the thin film transistor Tr may have an inverted staggered structure in which a gate electrode is disposed under a semiconductor layer and a source and drain electrodes are disposed over the semiconductor layer. In this case, the semiconductor layer may comprise amorphous silicon.

A gate line and a data line, which cross each other to define a pixel region, and a switching element, which is connected to the gate line and the data line is, may be further formed in the pixel region. The switching element is connected to the thin film transistor Tr, which is a driving element. Additionally, a power line is spaced apart in parallel from the gate line or the data line, and the thin film transistor Tr may further include a storage capacitor configured to constantly keep a voltage of the gate electrode for one frame.

In addition, the organic light emitting display device 100 may include a color filter for absorbing a part of the light emitted from the organic light emitting diode 200. For example, the color filter may absorb a light of specific wavelength such as red (R), green (G) or blue (B). In this case, the organic light emitting display device 100 can implement full-color through the color filter.

For example, when the organic light emitting display device 100 is a bottom-emission type, the color filter may be disposed on the interlayer insulating layer 140 with corresponding to the organic light emitting diode 200. Alternatively, when the organic light emitting display device 100 is a top-emission type, the color filter may be disposed over the organic light emitting diode 200, that is, above a second electrode 220.

A passivation layer 160 is disposed on the source and drain electrodes 152 and 154 over the whole substrate 102. The passivation layer 160 has a flat top surface and a drain contact hole 162 that exposes the drain electrode 154 of the thin film transistor Tr. While the drain contact hole 162 is disposed on the second semiconductor layer contact hole 154, it may be spaced apart from the second semiconductor layer contact hole 154.

The organic light emitting diode 200 includes a first electrode 210 that is disposed on the passivation layer 160 and connected to the drain electrode 154 of the thin film transistor Tr. The organic light emitting diode 200 further includes an emitting unit 230 as an emission layer and a second electrode 220 each of which is disposed sequentially on the first electrode 210.

The first electrode 210 is disposed in each pixel region. The first electrode 210 may be an anode and include a conductive material having a relatively high work function value. For example, the first electrode 210 may include, but is not limited to, a transparent conductive material such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the like.

In one exemplary embodiment, when the organic light emitting display device 100 is a top-emission type, a reflective electrode or a reflective layer may be disposed under the first electrode 210. For example, the reflective electrode or the reflective layer may include, but is not limited to, aluminum-palladium-copper (APC) alloy.

In addition, a bank layer 170 is disposed on the passivation layer 160 in order to cover edges of the first electrode 210. The bank layer 170 exposes a center of the first electrode 210.

An emitting unit 230 is disposed on the first electrode 210. In one exemplary embodiment, the emitting unit 230 may have a mono-layered structure of an emitting material layer. Alternatively, the emitting unit 230 may have a multiple-layered structure of a hole injection layer, a hole transport layer, an electron blocking layer, an emitting material layer, a hole blocking layer, an electron transport layer and/or an electron injection layer (See, FIGS. 2, 5, 7, 9 and 11). In one embodiment, the organic light emitting diode 200 may have one emitting unit 230. Alternatively, the organic light emitting diode 200 may have multiple emitting units 230 to form a tandem structure. The emitting unit 230 includes an organic compound having the structure of any one in Chemical Formulae 1, 4, 7, 8 and 11. As an example, the organic compound having the structure of any one in Chemical Formulae 1, 4, 7, 8 and 11 may be used a dopant of an emitting material layer which may further includes at least one host.

The second electrode 220 is disposed over the substrate 102 above which the emitting unit 230 is disposed. The second electrode 220 may be disposed over a whole display area and may include a conductive material with a relatively low work function value compared to the first electrode 210. The second electrode 220 may be a cathode. For example, the second electrode 220 may include, but is not limited to, aluminum (Al), magnesium (Mg), calcium (Ca), silver (Ag), alloy thereof or combination thereof such as aluminum-magnesium alloy (Al—Mg).

In addition, an encapsulation film 180 may be disposed over the second electrode 220 in order to prevent outer moisture from penetrating into the organic light emitting diode 200. The encapsulation film 180 may have, but is not limited to, a laminated structure of a first inorganic insulating film 182, an organic insulating film 184 and a second inorganic insulating film 186.

The emitting unit 230 of the OLED 200 includes the organic compound having the structure of any one in Chemical Formulae 1, 4, 7, 8 and 11, as described above. Since the organic compound has both an electron donor moiety and an electron acceptor moiety, the organic compound exhibits a delayed fluorescent property. The OLED 200 can enhance its luminous efficiency and lower its driving voltage so as to reduce its consumption power by applying the organic compound having the structure of any one in Chemical Formulae 1, 4, 7, 8 and 11 into the emitting unit 230.

[Organic Light Emitting Diode]

Figure 2:
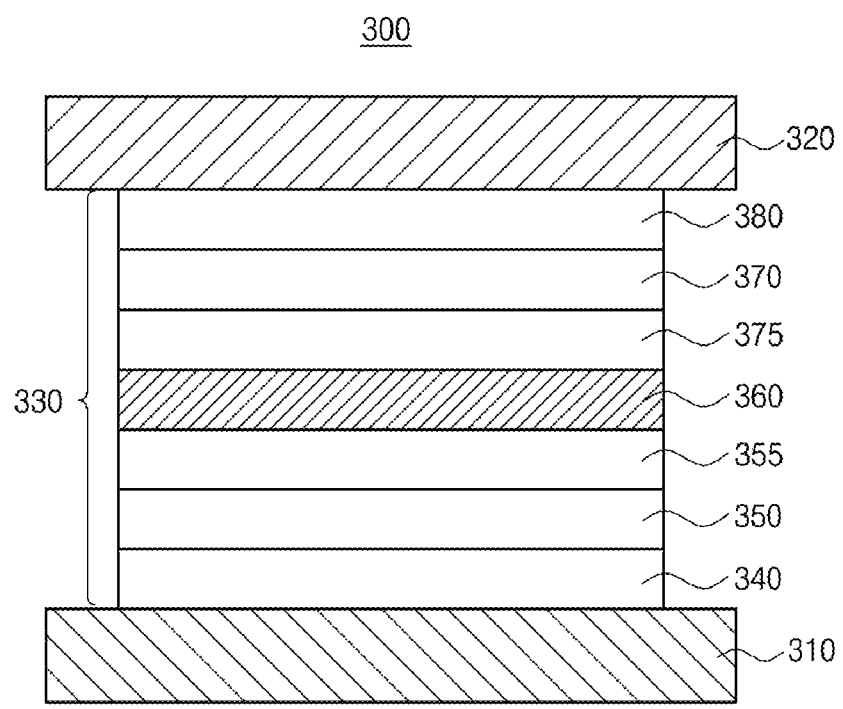
FIG. 2 is a schematic cross-sectional view illustrating an organic light emitting diode in accordance with an exemplary embodiment of the present disclosure.

FIG. 2 is a schematic cross-sectional view illustrating an organic light emitting diode in accordance with an exemplary embodiment of the present disclosure. As illustrated in FIG. 2, the organic light emitting diode (OLED) 300 in accordance with the first embodiment of the present disclosure includes first and second electrodes 310 and 320 facing each other, an emitting unit 330 as an emission layer disposed between the first and second electrodes 310 and 320. In one exemplary embodiment, the emitting unit 330 include a hole injection layer (HIL) 340, a hole transport layer (HTL) 350, an emitting material layer (EML) 360, an electron transport layer (ETL) 370 and an electron injection layer (EIL) 380 each of which is laminated sequentially from the first electrode 310. Alternatively, the emitting unit 330 may further include a first exciton blocking layer, i.e. an electron blocking layer (EBL) 355 disposed between the HTL 350 and the EML 360 and/or a second exciton blocking layer. i.e. a hole blocking layer (HBL) 375 disposed between the EML 360 and the ETL 370.

The first electrode 310 may be an anode that provides a hole into the EML 360. The first electrode 310 may include, but is not limited to, a conductive material having a relatively high work function value, for example, a transparent conductive oxide (TCO). In an exemplary embodiment, the first electrode 310 may include, but is not limited to, ITO, IZO, ITZO, SnO, ZnO, ICO, AZO, and the like.

The second electrode 320 may be a cathode that provides an electron into the EML 360. The second electrode 320 may include, but is not limited to, a conductive material having a relatively low work function values, i.e., a highly reflective material such as Al, Mg, Ca, Ag, alloy thereof, combination thereof, and the like. As an example, each of the first and second electrodes 310 and 320 may be laminated with a thickness of, but not limited to, about 30 nm to about 300 nm.

The HIL 340 is disposed between the first electrode 310 and the HTL 350 and improves an interface property between the inorganic first electrode 310 and the organic HTL 350. In one exemplary embodiment, the HIL 340 may include, but is not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino)triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f:2'3'-h]quinoxaline-2,3,6,7,10,11-hexacarbonitrile; HAT-CN), 1,3,5-tris[4-(diphenylamino)phenyl]benzene (TDAPB), poly(3,4-ethylenedioxythiophene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HIL 340 may be omitted in compliance with a structure of the OLED 300.

The HTL 350 is disposed adjacently to the EML 360 between the first electrode 310 and the EML 360. In one exemplary embodiment, the HTL 350 may include, but is not limited to, N,N'-Diphenyl-N,N'-bis(3-methylphenyl)-1,1'-biphenyl-4,4'-diamine (TPD), NPB, 4,4'-bis(N-carbazolyl)-1,1'-biphenyl (CBP), Poly[N,N'-bis(4-butylphenyl)-N,N'-bis(phenyl)-benzidine] (Poly-TPD), Poly[(9,9-dioctylfluorenyl-2,7-diyl)-co-(4,4'-(N-(4-sec-butylphenyl) diphenylamine))] (TFB), Di-[4-(N,N-di-p-tolyl-amino)-phenyl]cyclohexane (TAPC), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

In one exemplary embodiment, each of the HIL 340 and the HTL 350 may be laminated with a thickness of, but is not limited to, about 5 nm to about 200 nm, and preferably about 5 nm to about 100 nm.

The EML 360 may include a host doped with a dopant where a substantial light emission is occurred. In this exemplary embodiment, the EML 360 may include a host (a first host) doped with a dopant (a first dopant). For example, the organic compound having the structure of any one in Chemical Formulae 1, 4, 7, 8 and 11 may be used as a delayed fluorescent dopant (dopant 1 or T dopant) in the EML 360. The EML 360 may emit light of green color. The configuration and energy levels among the luminous materials in the EML 360 will be explained in more detail.

The ETL 370 and the EIL 380 are laminated sequentially between the EML 360 and the second electrode 320. The ETL 370 may include a material having high electron mobility so as to provide electrons stably with the EML 360 by fast electron transportation.

In one exemplary embodiment, the ETL 370 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like.

As an example, the ETL 370 may include, but is not limited to, tris-(8-hydroxyquinoline aluminum ($Alq_3$), 2-biphenyl-4-yl-5-(4-t-butylphenyl)-1,3,4-oxadiazole (PBD), spiro-PBD, lithium quinolate (Liq), 1,3,5-Tris(N-phenyl-benzimidazol-2-yl)benzene (TPBi), Bis(2-methyl-8-quinolinolato-N1,O8)-(1,1'-biphenyl-4-olato)aluminum (BAlq), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenanthroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl)1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)] (PFNBr) and/or tris(phenylquinoxaline) (TPQ).

The EIL 380 is disposed between the second electrode 320 and the ETL 370, and can improve physical properties of the second electrode 320 and therefore, can enhance the life span of the OLED 300. In one exemplary embodiment, the EIL 380 may include, but is not limited to, an alkali halide such as LiF, CsF, NaF, $BaF_2$ and the like, and/or an organic metal compound such as lithium benzoate, sodium stearate, and the like.

As an example, each of the ETL 370 and the EIL 380 may be laminated with a thickness of, but is not limited to, about 10 nm to about 100 nm.

When holes are transferred to the second electrode 320 via the EML 360 and/or electrons are transferred to the first electrode 310 via the EML 360, the luminous lifetime and the luminous efficiency of the OLED 300 may be reduced. In order to prevent those phenomena, the OLED 300 in accordance with this embodiment of the present disclosure has at least one exciton blocking layer disposed adjacently to the EML 360.

For example, the OLED 300 of the exemplary embodiment includes the EBL 355 between the HTL 350 and the EML 360 so as to control and prevent electron transfers. In one exemplary embodiment, the EBL 355 may include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, 1,3-bis(carbazol-9-yl)benzene (mCP), 3,3'-bis(N-carbazolyl)-1,1'-biphenyl (mCBP), CuPc, N,N'-bis[4-(bis(3-methylphenyl)amino)phenyl]-N,N'-diphenyl[1,1'-biphenyl]-4,4'-diamine (DNTPD), TDAPB, 2,8-bis(9-phenyl-9H-carbazol-3-yl)dibenzo[b,d]thiophene, and/or 3,6-bis(N-carbazolyl)-N-phenyl-carbazole.

In addition, the OLED 300 further includes the HBL 375 as a second exciton blocking layer between the EML 360 and the ETL 370 so that holes cannot be transferred from the EML 360 to the ETL 370. In one exemplary embodiment, the HBL 375 may include, but is not limited to, oxadiazole-based compounds, triazole-based compounds, phenanthroline-based compounds, benzoxazole-based compounds, benzothiazole-based compounds, benzimidazole-based compounds, and triazine-based compounds.

For example, the HBL 375 may include a compound having a relatively low HOMO energy level compared to the emitting material in EML 360. The HBL 375 may include, but is not limited to, BCP, BAlq, Alq$_3$, PBD, spiro-PBD, Liq, Bis-4,5-(3,5-di-3-pyridylphenyl)-2-methylpyrimidine (B3PYMPM), Oxybis(2,1-phenylene))bis(diphenylphosphine oxide (DPEPO), 9-(6-(9H-carbazol-9-yl)pyridine-3-yl)-9H-3,9'-bicarbazole and combination thereof.

As described schematically above, the EML 360 of the OLED 300 in accordance with the first embodiment of the present disclosure include a host, and a dopant having a delayed fluorescent property (T dopant), which is the organic compound having the structure of any one in Chemical Formulae 1, 4, 7, 8 and 11. When the EML 360 includes the dopant having the delayed fluorescent property, the OLED 300 improves its luminous efficiency and its luminous lifetime and has a lower driving voltage.

An Organic Light Emitting Diode (OLED) emits light as holes injected from the anode and electrons injected from the cathode are combined to form excitons in EML, and then unstable excited state excitons return to a stable ground state. Theoretically, when electrons meet holes to form exciton, a singlet exciton of a paired spin and a triplet exciton of an unpaired spin are produced by a ratio of 1:3 by spin arrangements. Only the singlet exciton among the excitons can be involved in emission process in case of fluorescent materials. Accordingly, the OLED may exhibit luminous efficiency by maximum 5% in case of using the common fluorescent material.

In contrast, phosphorescent materials use different luminous mechanism of converting both singlet excitons and triplet exciton into light. The phosphorescent materials can convert singlet excitons into triplet excitons through inter-system crossing (ISC). Therefore, it is possible to enhance luminous efficiency in case of applying the phosphorescent materials that use both the singlet excitons and the triplet excitons during the luminous process compared to the fluorescent materials. However, prior art blue phosphorescent materials exhibits too low of a color purity to use with the display device and exhibits a very short luminous lifetime, and therefore, they have not been used in commercial display devices.

A delayed fluorescent material, which can solve the limitations accompanied by the prior art fluorescent dopants and the phosphorescent dopants, has been developed recently. Representative delayed fluorescent material is a thermally-activated delayed fluorescent (TADF) material. Since the delayed fluorescent material generally has both an electron donor moiety and an electron acceptor moiety within its molecular structure, its triplet exciton energy can be converted upwardly to an intramolecular charge transfer (ICT) state. In case of using the delayed fluorescent material as a dopant, it is possible to use both the excitons of singlet energy level $S_1$ and the excitons of triplet energy level $T_1$ during the emission process.

Figure 3:
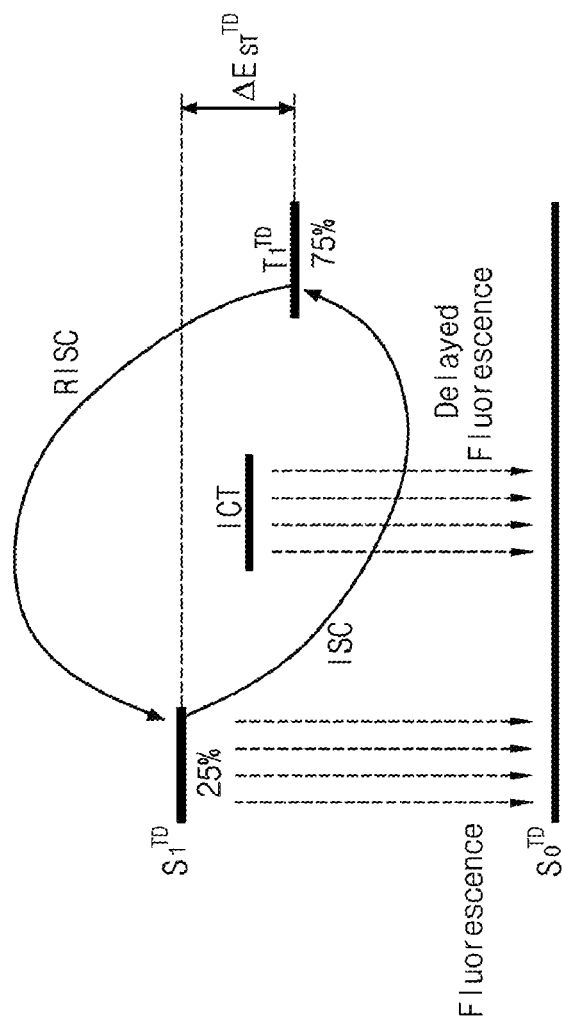
FIG. 3 is a schematic diagram illustrating a luminous mechanism of the delayed fluorescent material in an EML in accordance with an exemplary embodiment of the present disclosure.

The luminous mechanism of the delayed fluorescent material will be explained with referring to FIG. 3, which is a schematic diagram illustrating a luminous mechanism of the delayed fluorescent material in an EML in accordance with another exemplary embodiment of the present disclosure. As illustrated in FIG. 3, both the excitons of singlet energy level $S_1^{TD}$ and the excitons of triplet energy level $T_1^{TD}$ in the delayed fluorescent material can move to an intermediate energy level state, i.e. ICT state, and then the intermediate stated excitons can be transferred to a ground state ($S_0$; $S1 \to ICT \leftarrow T_1$). Since the excitons of singlet energy level $S_1^{TD}$ as well as the excitons of triplet energy level $T_1^{TD}$ in the delayed fluorescent material are involved in the emission process, the delayed fluorescent material has improved luminous efficiency.

Because both the HOMO and the LUMO are widely distributed over the whole molecule within the common fluorescent material, it is not possible to inter-convert between the singlet energy level and the triplet energy level within it (selection rule). In contrast, since the delayed fluorescent material, which can be converted to ICT state, has little orbital overlaps between HOMO and LUMO, there is little interaction between the HOMO state molecular orbital and the LUMO state molecular orbital in the state where dipole moment is polarized within the delayed fluorescent material. As a result, the changes of spin states of electrons does not have an influence on other electrons, and a new charge transfer band (CT band) that does not follow the selection rule is formed in the delayed fluorescent material.

In other words, since the delayed fluorescent material has the electron acceptor moiety spacing apart from the electron donor moiety within the molecule, it exists as a polarized state having a large dipole moment within the molecule. As the interaction between HOMO molecular orbital and LUMO molecular orbital becomes little in the state where the dipole moment is polarized, both the triplet energy level excitons and the singlet energy level excitons can be converted to ICT state. Accordingly, the excitons of triplet energy level $T_1$ as well as the excitons of singlet energy level $S_1$ can be involved in the emission process.

In case of driving the diode that includes the delayed fluorescent material, 25% excitons of singlet energy level $S_1^{TD}$ and 75% excitons of triplet energy level $T_1^{TD}$ are converted to ICT state by heat or electrical field, and then the converted excitons transfer to the ground state $S_0$ with luminescence. Therefore, the delayed fluorescent material may have 100% internal quantum efficiency in theory.

The delayed fluorescent material must have an energy level bandgap $\Delta E_{ST}^{TD}$ equal to or less than about 0.3 eV, for example, from about 0.05 to about 0.3 eV, between the singlet energy level $S_1^{TD}$ and the triplet energy level $T_1^{TD}$ so that exciton energy in both the singlet energy level and the triplet energy level can be transferred to the ICT state. The material having little energy level bandgap between the singlet energy level $S_1^{TD}$ and the triplet energy level $T_1^{TD}$ can exhibit common fluorescence in which the excitons of singlet energy level $S_1^{TD}$ can be transferred to the ground state $S_0$, as well as delayed fluorescence with Reverse Inter System Crossing (RISC) in which the excitons of triplet energy level $T_1^{TD}$ can be transferred upwardly to the excitons of singlet energy level $S_1^{TD}$, and then the exciton of singlet energy level $S_1^{TD}$ transferred from the triplet energy level $T_1^{TD}$ can be transferred to the ground state $S_0$.

The delayed fluorescent material can realize identical quantum efficiency as the prior art phosphorescent material including heavy metals because the delayed fluorescent material can obtain a theoretical luminous efficiency up to 100%. The host for implementing the delayed fluorescence can induce triplet exciton energy generated at the delayed fluorescent material to be involved in the luminous process without quenching as a non-emission. In order to induce such exciton energy transfer, energy levels among the host and the delayed fluorescent material should be adjusted.

Figure 4:
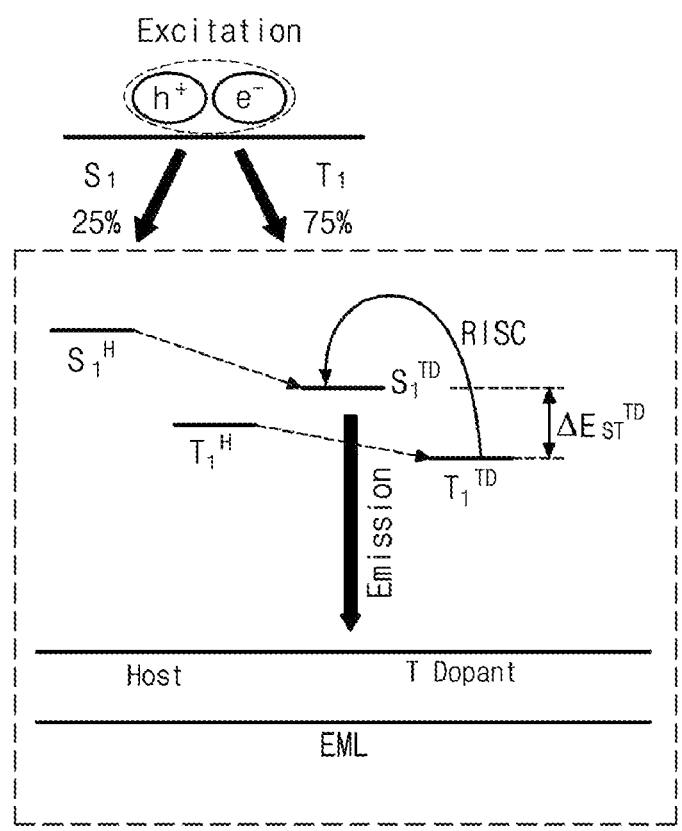
FIG. 4 is a schematic diagram illustrating a luminous mechanism by energy level bandgaps between luminous materials in accordance with an exemplary embodiment of the present disclosure.

FIG. 4 is a schematic diagram illustrating a luminous mechanism by energy level bandgaps between luminous materials in accordance with an exemplary embodiment of the present disclosure. As illustrated schematically in FIG. 4, each of an excited state singlet energy level $S_1^H$ and an excited state triplet energy level $T_1^H$ of the host should be higher than each of an excited state singlet energy level $S_1^{TD}$ and an excited state triple energy level $T_1^{TD}$ of the dopant, which has the delayed fluorescent property and is the organic compound having the structure of any one in Chemical Formulae 1, 4, 7, 8 and 11, respectively. For example, the excited triplet energy level $T_1^H$ of the host may be higher than the excited state triplet energy level $T_1^{TD}$ of the dopant by at least about 0.2 eV.

As an example, when the excited state triplet energy level $T_1^H$ of the host is not sufficiently higher than the excited state triplet energy levels of the dopant, which may be a delayed fluorescent material, the excitons of the triplet state level $T_1^H$ of the dopant can be reversely transferred to the excited state triplet energy level $T_1^H$ of the host, which cannot utilize triplet exciton energy. Accordingly, the excitons of the triplet state level $T_1^{TD}$ of the dopant having the delayed fluorescent property may be quenched as a non-emission and the triplet state excitons of the dopant cannot be involved in the emission. As an example, the host may have an excited state singlet energy level $S_1^H$ of equal to or more than about 2.8 eV and an excited state triplet energy level $T_1^H$ of equal to or more than about 2.6 eV, but are not limited thereto.

The dopant (TD), which has the delayed fluorescent material, which may be the organic compound having the structure of any one in Chemical Formulae 1, 4, 7, 8 and 11, should have an energy level bandgap $\Delta E_{ST}^{TD}$ between the excited stated singlet energy level $S_1^{TD}$ and the excited state triplet energy level $T_1^{TD}$ equal to or less than about 0.3 eV, for example between about 0.05 and about 0.3 eV, in order to realize delayed fluorescence (See, FIG. 3).

In addition, it is necessary to adjust properly HOMO energy levels and LUMO energy levels of the host and the dopant, which may be the fluorescent material. For example, it is preferable that an energy level bandgap (|HOMO$^H$-HOMO$^{TD}$|) between a HOMO energy level (HOMO$^H$) of the host and a HOMO energy level (HOMO$^{TD}$) of the dopant, or an energy level bandgap (|LUMO$^H$-LUMO$^{TD}$|) between a LUMO energy level (LUMO$^H$) of the host and a LUMO energy level (LUMO$^{TD}$) of the dopant may be equal to or less than about 0.5 eV, for example, between about 0.1 eV to about 0.5 eV. In this case, the charges can be transported efficiently from the host to the first dopant and thereby enhancing an ultimate luminous efficiency.

Moreover, an energy level bandgap (Eg$^H$) between the HOMO energy level (HOMO$^H$) and the LUMO energy level (LUMO$^H$) of the host may be larger than an energy level bandgap (Eg$^{TD}$) between the HOMO energy level (HOMO$^{TD}$) and the LUMO energy level (LUMO$^{TD}$) of the dopant. As an example, the HOMO energy level (HOMO$^H$) of the host is deeper or lower than the HOMO energy level (HOMO$^{TD}$) of the dopant, and the LUMO energy level (LUMO$^H$) of the host is shallower or higher than the LUMO energy level (LUMO$^{TD}$) of the dopant.

In one exemplary embodiment, the organic compound having the structure of any one in Chemical Formulae 1, 4, 7, 8 and 11, as the dopant having the delayed fluorescent dopant, may have a HOMO energy level (HOMO$^{TD}$) between about −5.0 and about −6.0 eV, and preferably between about −5.0 and about −5.5 eV and a LUMO energy level (LUMO$^{TD}$) between about −2.5 and about −3.5 eV, and preferably about −2.5 and about −3.0 eV. Also, an energy level bandgap (Eg$^{TD}$) between those HOMO and LUMO energy levels of the organic compound may be between about 2.2 to about 3.0 eV, and preferably about 2.4 and about 2.8 eV. In addition, the host may have a HOMO energy level (HOMO') between about −5.0 and about −6.5 eV, and preferably between about −5.5 and about −6.2 eV and a LUMO energy level (LUMO$^{TD}$) between about −1.5 and about −3.0 eV, and preferably about −1.5 and about −2.0 eV. Also, an energy level bandgap (Eg$^H$) between those HOMO and LUMO energy levels of the host may be between about 3.0 to about 4.0 eV, and preferably about 3.0 and about 3.5 eV.

In one exemplary embodiment, the host in the EML 360 may include, but is not limited to, 9-(3-(9H-carbazol-9-yl)phenyl)-9H-carbazole-3-carbonitrile (mCP-CN), CBP, mCBP, mCP, DPEPO, 2,8-bis(diphenylphosphoryl)dibenzothiophene (PPT), 1,3,5-tri[(3-pyridyl)-phen-3-yl]benzene (TmPyPB), 2,6-di(9H-carbazol-9-yl)pyridine (PYD-2Cz), 2,8-di(9H-carbazol-9-yl)dibenzothiophene (DCzDBT), 3',5'-Di(carbazol-9-yl)-[1,1'-bipheyl]-3,5-dicarbonitrile (DCzTPA), 4-(9H-carbazol-9-yl)biphenyl-3,5-dicarbonitrile (pCzB-2CN), 3'-(9H-carbazol-9-yl)biphenyl-3,5-dicarbonitrile (mCzB-2CN), diphenyl-4-triphenylsilylphenyl-phosphine oxide (TSPO1), 9-(9-phenyl-9H-carbazol-6-yl)-9H-carbazole (CCP), 9-(4-(9H-carbazol-9-yl)phenyl)-9H-3,9'-bicarbazole, 9-(3-(9H-carbazol-9-yl)phenyl)-9H-3,9'-bicarbazole, 9-(6-(9H-carbazol-9-yl)pyridin-3-yl)-9H-3,9'-bicarbazole and/or 4-(3-(triphenylen-2-yl)phenyl)dibenzo[b,d]thiophene.

When the EML 360 includes the host and the dopant, i.e. the organic compound having the structure of any one in Chemical Formulae 1, 4, 7, 8 and 11, the weight ratio of the host may be equal to or more than the weight ratio of the dopant. As an example, the EML 360 may include the dopant of about 1 to about 50% by weight, preferably of about 10 to about 40% by weight, and more preferably of about 20 to about 40% by weight. The EML 360 may be laminated with a thickness of, but is not limited to, about 10 nm to about 200 nm, preferably about 20 nm to about 100 nm, and more preferably about 30 nm to about 50 nm.

Figure 5:
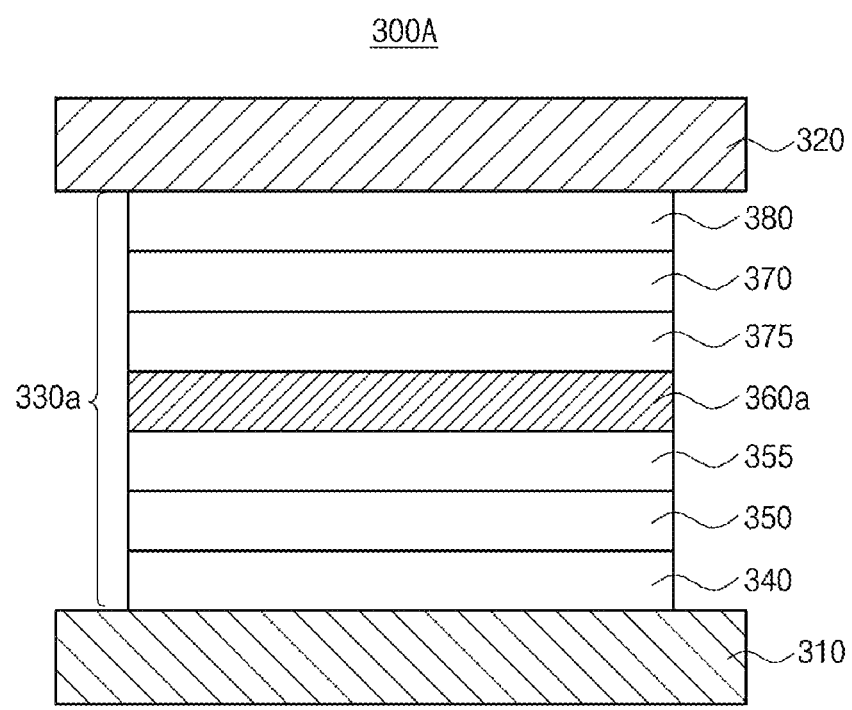
FIG. 5 is a schematic cross-sectional view illustrating an organic light emitting diode in accordance with another exemplary embodiment of the present disclosure.

In the above first embodiment, the EML 360 includes only one dopant having the delayed fluorescent property. Unlike that embodiment, the EML may include plural dopants having different luminous properties. FIG. 5 is a schematic cross-sectional view illustrating an organic light emitting diode in accordance with another exemplary embodiment of the present disclosure. As illustrated in FIG. 5, the OLED 300A according to the second embodiment of the present disclosure includes first and second electrodes 310 and 320 facing each other and an emitting unit 330a disposed between the first and second electrodes 310 and 320.

In one exemplary embodiment, the emitting unit 330a as an emission layer includes a HIL 340, a HTL 350, an EML 360a, an ETL 370 and an EIL 380 each of which is laminated sequentially over the first electrode 310. Alternatively, the emitting unit 330a may further include a first exciton blocking layer, i.e. an EBL 355 disposed between the HTL 350 and the EML 360a and/or a second exciton blocking layer, i.e. a HBL 375 disposed between the EML 360a and the ETL 370. The emitting unit 330a may have the same configurations and materials as the emitting unit 330 in FIG. 2 except the EML 360a.

The EML 360a may include a host (a first host), a first dopant and a second dopant. The first dopant may be a delayed fluorescent dopant (T dopant; TD) and the second dopant may be a fluorescent dopant (F dopant; FD). In this case, the organic compound having the structure of any one in Chemical Formulae 1, 4, 7, 8 and 11 may be used as the first dopant and a fluorescent or phosphorescent material may be sued as the second dopant. The OLED 300A can implement hyper-fluorescence enhancing its luminous efficiency by adjusting energy levels among the luminous materials, i.e. the host and the dopants.

Figure 6:
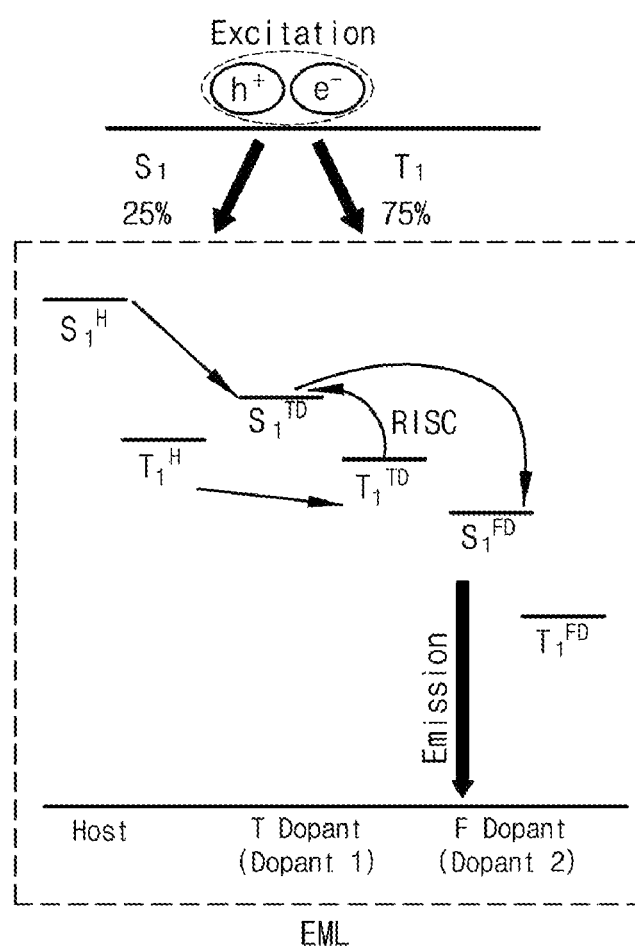
FIG. 6 is a schematic diagram illustrating a luminous mechanism by energy level bandgaps among luminous materials in accordance with another exemplary embodiment of the present disclosure.

FIG. 6 is a schematic diagram illustrating luminous mechanism by energy level bandgap among luminous materials in accordance with another exemplary embodiment of the present disclosure.

When an EML includes only the dopant which has the delayed fluorescent property and has the structure of any one in Chemical Formula 1, 4, 7, 8 and 11, the EML may implement high internal quantum efficiency as the prior art phosphorescent materials including heavy metals because the dopant can exhibit 100% internal quantum efficiency in theory.

However, because of the bond formation between the electron acceptor and the electron donor and conformational twists within the delayed fluorescent material, additional charge transfer transition (CT transition) within the delayed fluorescent material is caused thereby, and the delayed fluorescent material have various geometry. As a result, the delayed fluorescent materials show emission spectra having very broad FWHM (full-width at half maximum) in the course of emission, which results in poor color purity. In addition, the delayed fluorescent material utilizes the triplet exciton energy as well as the singlet exciton energy in the luminous process with rotating each moiety within its molecular structure, which results in twisted internal charge transfer (TICT). As a result, the luminous lifetime of an OLED including only the delayed fluorescent materials may be reduced owing to weakening of molecular bonding forces among the delayed fluorescent materials.

In the second embodiment, the EML 360a further includes the second dopant, which may be a fluorescent or phosphorescent material, in order to prevent the color purity and luminous lifetime from being reduced in case of using only the delayed fluorescent materials. The triplet exciton energy of the first dopant (T dopant), which may be the delayed fluorescent material, is converted upwardly to the singlet exciton energy of its own by RISC mechanism, then the converted singlet exciton energy of the first dopant can be transferred to the second dopant (F dopant), which may be the fluorescent or phosphorescent material, in the same EML 360a by Dexter energy transfer mechanism, which transfer exciton energies depending upon wave function overlaps among adjacent molecules by inter-molecular electron exchanges and exciton diffusions.

When the EML 360a includes the host, the first dopant (T dopant) which may be the organic compound having the structure of any one in Chemical Formulae 1, 4, 7, 8 and 11 and having the delayed fluorescent property and the second dopant (F dopant) which may be the fluorescent or phosphorescent material, it is necessary to adjust properly energy levels amount those luminous materials.

An energy level bandgap between an excited state singlet energy level $S_1^{TD}$ and an excited state triplet energy level $T_1^{TD}$ of the first dopant (T dopant), which is the organic compound having the structure of any one in Chemical Formulae 1, 4, 7, 8 and 11, may be equal to or less than about 0.3 eV in order to realize the delayed fluorescence. In addition, each of an excited state singlet energy level $S_1^H$ and an excited state triplet energy level $T_1^H$ of the host is higher than each of the excited state singlet energy level $S_1^{TD}$ and the excited state triplet energy level $T_1^{TD}$ of the first dopant, respectively. As an example, the excited state triplet energy level $T_1^H$ of the host may be higher than the excited state triplet energy level $T_1^{TD}$ of the first dopant by at least about 0.2 eV. Moreover, the excited state triplet energy level $T_1^{TD}$ of the first dopant is higher than an excited state triplet energy level $T_1^{FD}$ of the second dopant. In one exemplary embodiment, the excited state singlet energy level $S_1^{TD}$ of the first dopant may be higher than an excited state singlet energy level $S_1^{FD}$ of the second dopant as a fluorescent material.

In addition, an energy level bandgap ($|HOMO^H-HOMO^{TD}|$) between a HOMO energy level ($HOMO^H$) of the host and a HOMO energy level ($HOMO^{TD}$) of the first dopant, or an energy level bandgap ($|LUMO^H-LUMO^{TD}|$) between a LUMO energy level ($LUMO^H$) of the host and a LUMO energy level ($LUMO^{TD}$) of the first dopant may be equal to or less than about 0.5 eV.

For example, the host may include, but is not limited to, mCP-CN, CBP, mCBP, mCP, DPEPO, PPT, TmPyPB. PYD-2Cz, DCzDBT, DCzTPA, pCzB-2CN, mCzB-2CN, TSPO1, CCP, 9-(4-(9H-carbazol-9-yl)phenyl)-9H-3,9'-bicarbazole, 9-(3-(9H-carbazol-9-yl)phenyl)-9H-3,9'-bicarbazole, 9-(6-(9H-carbazol-9-yl)pyridin-3-yl)-9H-3,9'-bicabazole and/or 4-(3-(triphenylen-2-yl)phenyl)dibenzo[b,d]thiophene.

The exciton energy should be effectively transferred from the first dopant as the delayed fluorescent material to the second dopant as the fluorescent or phosphorescent material in order to implement hyper-fluorescence. With regard to energy transfer efficiency from the delayed fluorescent material to the fluorescent or phosphorescent material, an overlap between an emission spectrum of the delayed fluorescent material and an absorption spectrum of the fluorescent or phosphorescent material can be considered. As an example, a fluorescent or phosphorescent material having an absorption spectrum with overlapping area with an emission spectrum of the first dopant, i.e. the organic compound having the structure of any one in Chemical Formulae 1, 4, 7, 8 and 11, may be used as the second dopant in order to transfer exciton energy efficiently from the first dopant to the second dopant.

In one exemplary embodiment, the fluorescent material as the second dopant may have, but is not limited to, quinolino-acridine core. As an example, the second dopant having the quinolino-acridine core may include 5,12-dimethylquinolino[2,3-b]acridine-7,14(5H, 12H)-dione($S_1$: 2.3 eV; $T_1$: 2.0 eV; LUMO: −3.0 eV; HOMO: −5.4 eV), 5,12-diethylquinolino[2,3-b]acridine-7,14(5H, 12H)-dione($S_1$: 2.3 eV; $T_1$: 2.2 eV; LUMO: −3.0 eV; HOMO: −5.4 eV), 5,12-dibutyl-3,10-difluoroquinolino[2,3-b]acridine-7,14(5H, 12H)-dione($S_1$: 2.2 eV; $T_1$: 2.0 eV; LUMO: −3.1 eV; HOMO: −5.5 eV), 5,12-dibutyl-3,10-bis(trifluoromethyl)quinolino[2,3-b]acridine-7,14(5H, 12H)-dione($S_1$: 2.2 eV; $T_1$: 2.0 eV; LUMO: −3.1 eV; HOMO: −5.5 eV), 5,12-dibutyl-2,3,9,10-tetrafluoroquinolino[2,3-b]acridine-7,14(5H, 12H)-dione(S: 2.0 eV; $T_1$: 1.8 eV; LUMO: −3.3 eV; HOMO: −5.5 eV).

In addition, the fluorescent material as the second dopant may include, but is not limited to, 1,1,7,7-tetramethyl-2,3,6,7-tetrahydro-1H,5H-benzo[ij]quinolizin-9-yl)ethenyl]-4H-pyran-4-ylidene}propanedinitrile(DCJTB; $S_1$: 2.3 eV; $T_1$: 1.9 eV; LUMO: −3.1 eV; HOMO: −5.3 eV). Moreover, metal complexes which can emit light of green color may be used as the second dopant.

In one exemplary embodiment, the weight ratio of the host may be larger than the weight ratio of the first and second dopants in the EML 360a, and the weight ratio of the first dopant may be larger larger than the weight ratio of the second dopant. In an alternative embodiment, the weight ratio of the host is larger than the weight ratio of the first dopant and the weight ratio of the first dopant is larger than the weight ratio of the second dopant. When the weight ratio of the first dopant is larger than the weight ratio of the second dopant, excition energy can be transferred enough from the first dopant to the second dopant by Dexter energy transfer mechanism. As an example, the EML 360a includes the host of about 60 to about 75% by weight, the first dopant of about 20 to about 40% by weight and the second dopant of about 0.1 to about 5% by weight.

Figure 7:
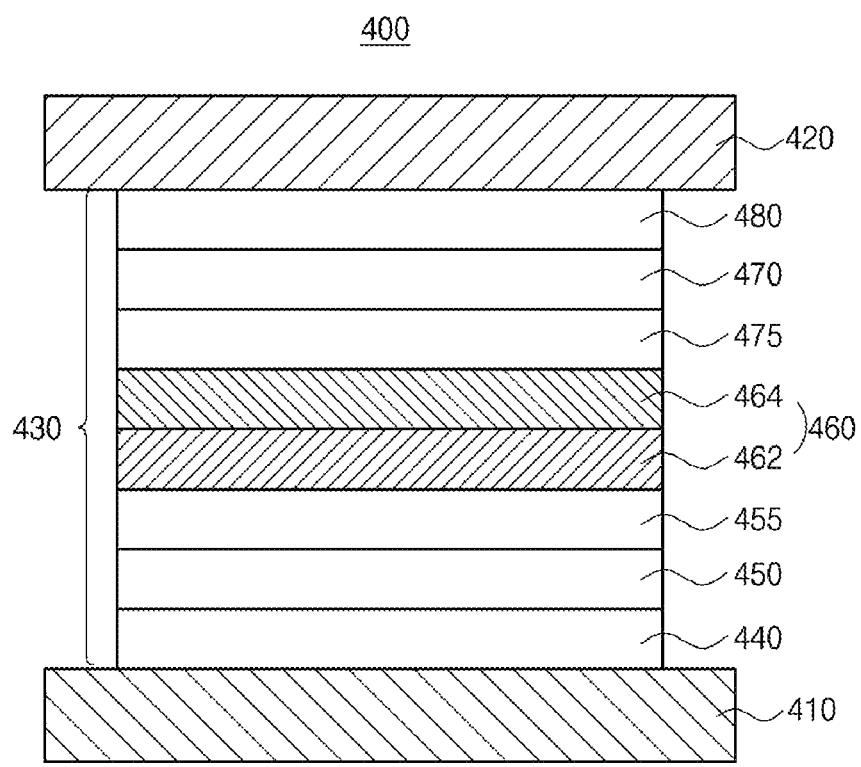
FIG. 7 is a schematic cross-sectional view illustrating an organic light emitting diode in accordance with another exemplary embodiment of the present disclosure.
Figure 8:
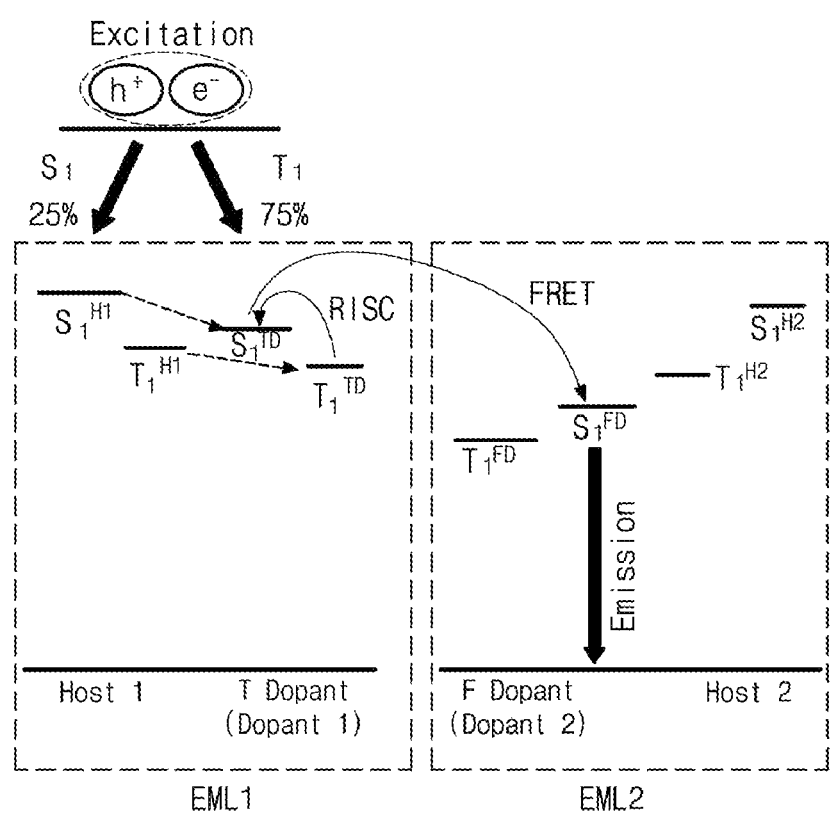
FIG. 8 is a schematic diagram illustrating a luminous mechanism by energy level bandgaps among luminous materials in accordance with another exemplary embodiment of the present disclosure.

The OLEDs in accordance with the previous embodiments have a single-layered EML. Alternatively, an OLED in accordance with the present disclosure may include multiple-layered EML. FIG. 7 is a schematic cross-sectional view illustrating an organic light emitting diode having a double-layered EML in accordance with another exemplary embodiment of the present disclosure. FIG. 8 is a schematic diagram illustrating luminous mechanism by energy level bandgap among luminous materials in accordance with another exemplary embodiment of the present disclosure.

As illustrated in FIG. 7, the OLED 400 in accordance with an exemplary third embodiment of the present disclosure includes first and second electrodes 410 and 420 facing each other and an emitting unit 430 as an emission layer disposed between the first and second electrodes 410 and 420.

In one exemplary embodiment, the emitting unit 430 includes an HIL 440, an HTL 450, and EML 460, an ETL 470 and an EIL 480 each of which is laminated sequentially over the first electrode 410. In addition, the emitting unit 430 may further include an EBL 455 as a first exciton blocking layer disposed between the HTL 450 and the EML 460, and/or an HBL 475 as a second exciton blocking layer disposed between the EML 460 and the ETL 470.

As described above, the first electrode 410 may be an anode and may include, but is not limited to, a conductive material having a relatively large work function values such as ITO, IZO, SnO, ZnO, ICO, AZO, and the like. The second electrode 420 may be a cathode and may include, but is not limited to, a conductive material having a relatively small work function values such as Al, Mg, Ca, Ag, alloy thereof or combination thereof.

The HIL 440 is disposed between the first electrode 410 and the HTL 450. The HIL 440 may include, but is not limited to, MTDATA. NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 440 may be omitted in compliance with the structure of the OLED 400.

The HTL 450 is disposed adjacently to the EML 460 between the first electrode 410 and the EML 460. The HTL 450 may include, but is not limited to, aromatic amine compounds such as TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EML 460 includes a first EML (EML1) 462 and a second EML (EML2) 464. The EML1 462 is disposed between the EBL 455 and the HBL 475 and the EML2 464 is disposed between the EML1 462 and the HBL 475. One of the EML1 462 and the EML2 464 includes a first dopant (T dopant) having a delayed fluorescent property, for example, an organic compound having the structure of any one in Chemical Formulae 1, 4, 7, 8 and 11, the other of the EML 1462 and the EML2 464 includes a second dopant (F dopant) as a fluorescent or phosphorescent material. The configuration and energy levels among the luminous materials in the EML 460 will be explained in more detail below.

The ETL 470 is disposed between the EML 460 and the EIL 480. In one exemplary embodiment, the ETL 470 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like. As an example, the ETL 470 may include, but is not limited to, $Alq_3$, PBD, spiro-PBD, Liq, TPBi, BAlq, Bphen, NBphen, BCP, TAZ, NTAZ, TpPyPB, TmPPPyTz, PFNBr and/or TPQ.

The EIL 480 is disposed between the second electrode 420 and the ETL 470. In one exemplary embodiment, the EIL 480 may include, but is not limited to, an alkali halide such as LiF, CsF, NaF, $BaF_2$, and the like, and/or an organic metal compound such as lithium benzoate, sodium stearate, and the like.

The EBL 455 is disposed between the HTL 450 and the EML 460 for controlling and preventing electron transportations between the HTL 450 and the EML 460. As an example, The EBL 455 may include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, DNTPD, TDAPB, 2,8-bis(9-phenyl-9H-carbazol-3-yl)dibenzo[b,d]thiophene and/or 3,6-bis(N-carbazolyl)-N-phenyl-carbazole.

The HBL 475 is disposed between the EML 460 and the ETL 470 for preventing hole transportations between the EML 460 and the ETL 470. In one exemplary embodiment, the HBL 475 may include, but is not limited to, oxadiazole-based compounds, triazole-based compounds, phenanthroline-based compounds, benzoxazole-based compounds, benzothiazole-based compounds, benzimidazole-based compounds, and triazine-based compounds. As an example, the HBL 475 may include a compound having a relatively low HOMO energy level compared to the emitting material in EML 460. The HBL 475 may include, but is not limited to, BCP, BAlq, $Alq_3$, PBD, spino-PBD, Liq, B3PYMPM, DPEPO, 9-(6-(9H-carbazol-9-yl)pyridine-3-yl)-9H-3,9'-bicarbazole and combination thereof.

In the exemplary third embodiment, the EML1 462 includes a first host and a first dopant, which is a delayed fluorescent material and the EML 464 includes a second host and a second dopant, which is a fluorescent or phosphorescent material.

The EML1 462 includes the first host and the first dopant which is the delayed fluorescent material, i.e. the organic compound having the structure of any one in Chemical Formulae 1, 4, 7, 8 and 11. An energy level bandgap ($\Delta E_{ST}^{TD}$) between the excited state singlet energy level $S_1^{TD}$ and the excited state triplet energy level $T_1^{TD}$ of the first dopant is very small ($\Delta E_{ST}^{TD}$ is equal to or less than about 0.3 eV; See, FIG. 3) so that triplet exciton energy of the first dopant can be transferred to the singlet exciton energy of its own by RISC mechanism. While the first dopant has high internal quantum efficiency, but it has poor color purity due to its wide FWHM (full-width half maximum).

On the contrary, the EML2 464 may include the second host and the second dopant as a fluorescent material. While the second dopant as a fluorescent material has advantage in terms of color purity due to its narrow FWHM, but its internal quantum efficiency is low because its triplet exciton cannot be involved in a luminous process.

However, in this exemplary embodiment, the singlet exciton energy and the triplet exciton energy of the first dopant, which has the delayed fluorescent property, in the EML 1 462 can be transferred to the second dopant, which may be the fluorescent or phosphorescent material, in the EML2 464 disposed adjacently to the EML1 462 by FRET (Forster resonance energy transfer) mechanism, which transfers energy non-radially through electrical fields by dipole-dipole interactions. Accordingly, the ultimate emission occurs in the second dopant within the EML2 464.

In other words, the triplet exciton energy of the first dopant is converted upwardly to the singlet exciton energy of its own in the EML1 462 by RISC mechanism. Then, the converted singlet exciton energy of the first dopant is transferred to the singlet exciton energy of the second dopant because the excited state singlet energy level $S_1^{TD}$ of the first dopant is higher than the excited state singlet energy level $S_1^{TD}$ of the second dopant (See, FIG. 8). The second dopant in the EML2 464 can emit light using the triplet exciton energy as well as the singlet exciton energy.

As the exciton energy, which is generated at the first dopant as the delayed fluorescent material in the EML1 462, is efficiently transferred from the first dopant to the second dopant in the EML2 464, a hyper-fluorescence can be realized. In this case, the first dopant only acts as transferring exciton energy to the second dopant. Substantial light emission is occurred in the EML2 464 including the second dopant which is the fluorescent or phosphorescent dopant and has a narrow FWHM. Accordingly, the OLED 400 can enhance its quantum efficiency and improve its color purity due to narrow FWHM.

Each of the EML1 462 and the EML2 464 includes the first host and the second host, respectively. The exciton energies generated at the first and second hosts should be transferred to the first dopant as the delayed fluorescent material to emit light. It is necessary to adjust energy levels among the luminous materials in order to realize a hyper-fluorescence.

As illustrated in FIG. 8, each of excited state singlet energy levels $S_1^{H1}$ and $S_1^{H2}$ and excited state triplet energy levels $T_1^{H1}$ and $T_1^{H2}$ of the first and second hosts should be higher than each of the excited state singlet energy level $S_1^{TD}$ and the excited state triplet energy level $T_1^{TD}$ of the first dopant as the delayed fluorescent material, respectively.

For example, when each of the excited triplet energy levels $T_1^{H1}$ and $T_1^{H2}$ of the first and second hosts is not high enough than the excited state triplet energy level $T_1^{TD}$ of the first dopant, the triplet exciton of the first dopant may be reversely transferred to the excited state triplet energy levels $T_1^{H1}$ and $T_1^{H2}$ of the first and second hosts, which cannot utilize triplet exciton energy. Accordingly, the excitons of the triplet state level $T_1^{TD}$ of the first dopant may be quenched as a non-emission and the triplet state excitons of the first dopant cannot be involved in the emission. As an example, each of the excited state triplet energy levels $T_1^{H1}$ and $T_1^{H2}$ of the first and second hosts may be higher than the excited state triplet energy level $T_1^{TD}$ of the first dopant by at least about 0.2 eV.

The excited state singlet energy level $S_1^{H2}$ of the second host is higher than an excited state singlet energy level $S_1^{FD}$ of the second dopant. In this case, the singlet exciton energy generated at the second host can be transferred to the excited singlet energy level $S_1^{FD}$ of the second dopant.

In addition, it is necessary for the EML 460 to implement high luminous efficiency and color purity as well as to transfer exciton energy efficiently from the first dopant, which is converted to ICT complex state by RISC mechanism in the EML1 462, to the second dopant which is the fluorescent or phosphorescent material in the EML2 464. In order to realize such an OLED 400, the excited state triplet energy level $T_1^{TD}$ of the first dopant is higher than an excited state triplet energy level $T_1^{FD}$ of the second dopant. In one exemplary embodiment, the excited state singlet energy level $S_1^{TD}$ of the first dopant is higher than an excited state singlet energy level $S_1^{FD}$ of the second dopant as a fluorescent material.

In one exemplary embodiment, the energy level bandgap between the excited state singlet energy level $S_1^{TD}$ and the excited state triplet energy level $T_1^{TD}$ of the first dopant may be equal to or less than about 0.3 eV. In addition, an energy level bandgap ($|HOMO^H-HOMO^{TD}|$) between a HOMO energy level ($HOMO^H$) of the first and/or second hosts and a HOMO energy level ($HOMO^{TD}$) of the first dopant, or an energy level bandgap ($|LUMO^H-LUMO^{TD}|$) between a LUMO energy level ($LUMO^H$) of the first and/or second hosts and a LUMO energy level ($LUMO^{TD}$) of the first dopant may be equal to or less than about 0.5 eV.

When the luminous materials do not satisfy the required energy levels as described above, exciton energies are quenched at the first and second dopants or exciton energies cannot transferred efficiently from the host to the dopants, so that OLED 400 may have reduced quantum efficiency.

The first host and the second host may be the same or different from each other. For example, each of the first host and the second host may independently include, but is not limited to, mCP-CN, CBP, mCBP, mCP, DPEPO, PPT, TmPyPB, PYD-2Cz, DCzDBT, DCzTPA, pCzB-2CN, mCzB-2CN, TSPO1, CCP, 9-(4-(9H-carbazol-9-yl)phenyl)-9H-3,9'-bicarbazole, 9-(3-(9H-carbazol-9-yl)phenyl)-9H-3, 9'-bicarbazole, 9-(6-(9H-carbazol-9-yl)pyridin-3-yl)-9H-3, 9'-bicarbazole and/or 4-(3-(triphenylen-2-yl)phenyl)dibenzo [b,d]thiophene.

The second dopant may have narrow FWHM and have luminous spectrum having large overlapping area with the absorption spectrum of the first dopant. As an example, the second dopant may include, but is not limited to, an organic compound having a quinolino-acridine core such as 5,12-dimethylquinolino[2,3-b]acridine-7,14(5H, 12H)-dione, 5,12-diethylquinolino[2,3-b]acridine-7,14(5H, 12H)-dione, 5,12-dibutyl-3,10-difluoroquinolino[2,3-b]acridine-7,14 (5H, 12H)-dione, 5,12-dibutyl-3,10-bis(trifluoromethyl)qui-nolino[2,3-b]acridine-7,14(5H, 12H)-dione, 5,12-dibutyl-2, 3,9,10-tetrafluoroquinolino[2,3-]acridine-7,14(5H, 12H)-dione, DCJTB and any metal complexes which can emit light of green color.

In one exemplary embodiment, each of the first and second hosts in the EML1 462 or the EML2 464 may have weight ratio equal to or more than the first dopant and the second dopant in the same EMLs 462 and 464, respectively. In addition, the weight ratio of the first dopant in the EML1 462 may be larger than the weight ratio of the second dopant in the EML2 464. In this case, it is possible to transfer enough exciton energy from the first dopant in the EML1 462 to the second dopant in the EML2 464.

Particularly, the weight ratio of the first host may be equal to or more than the weight ratio of the first dopant in the EML1 462. As an example, the EML1 462 may include the first host of about 50 to about 90% by weight, preferably about 60 to about 90% by weight, and more preferably about 60 to about 80% by weight, and the first dopant of about 1 to about 50% by weight, preferably about 10 to about 40% by weight, and more preferably about 20 to about 40% by weight.

The weight ratio of the second host may be more than the weight ratio of the second dopant in the EML2 464. As an example, the EML2 464 may include the second host of about 90 to about 99% by weight, and preferably about 95 to about 99% by weight and the second dopant of about 1 to about 10% by weight, and preferably about 1 to about 5% by weight.

Each of the EML1 462 and the EML2 464 may be laminated with a thickness of, but is not limited to, about 5 to about 100 nm, preferably about 10 nm to about 30 nm, and more preferably about 10 nm to about 20 nm.

When the EML2 464 is disposed adjacently to the HBL 475 in one exemplary embodiment, the second host, which is included in the EML2 464 together with the second dopant, may be the same material as the HBL 475. In this case, the EML2 464 may have a hole blocking function as well as an emission function. In other words, the EML2 464 can act as a buffer layer for blocking holes. In one embodiment, the HBL 475 may be omitted where the EML2 464 may be a hole blocking layer as well as an emitting material layer.

When the EML2 464 is disposed adjacently to the EBL 455 in another exemplary embodiment, the second host may be the same material as the EBL 455. In this case, the EML2 464 may have an electron blocking function as well as an emission function. In other words, the EML2 464 can act as a buffer layer for blocking electrons. In one embodiment, the EBL 455 may be omitted where the EML2 464 may be an electron blocking layer as well as an emitting material layer.

Figure 9:
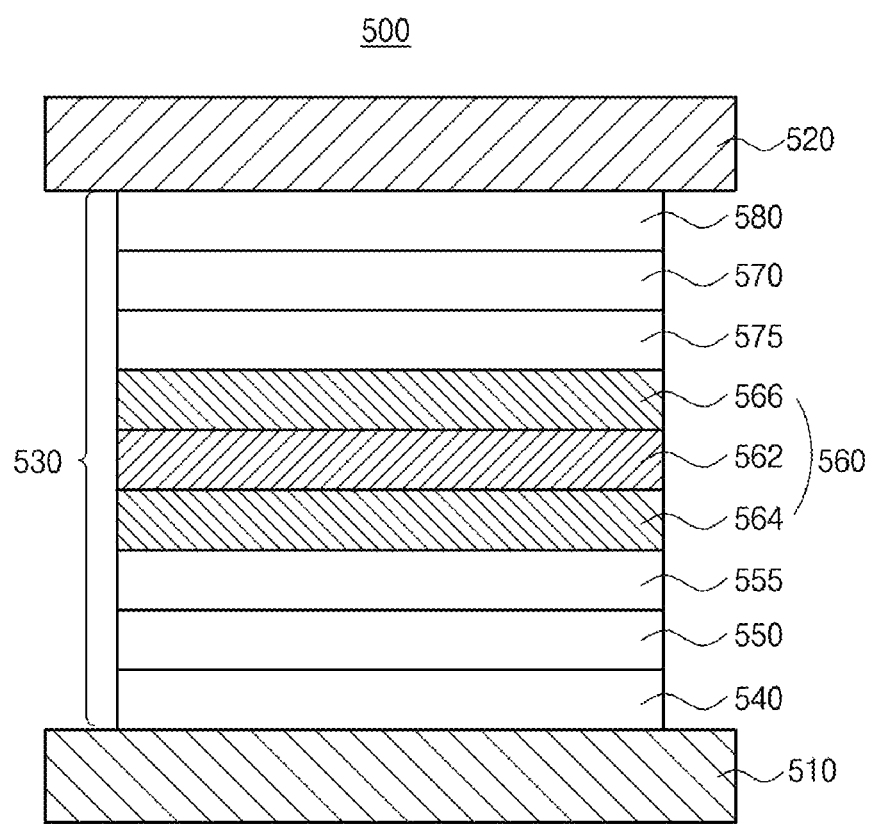
FIG. 9 is a schematic cross-sectional view illustrating an organic light emitting diode in accordance with another exemplary embodiment of the present disclosure.
Figure 10:
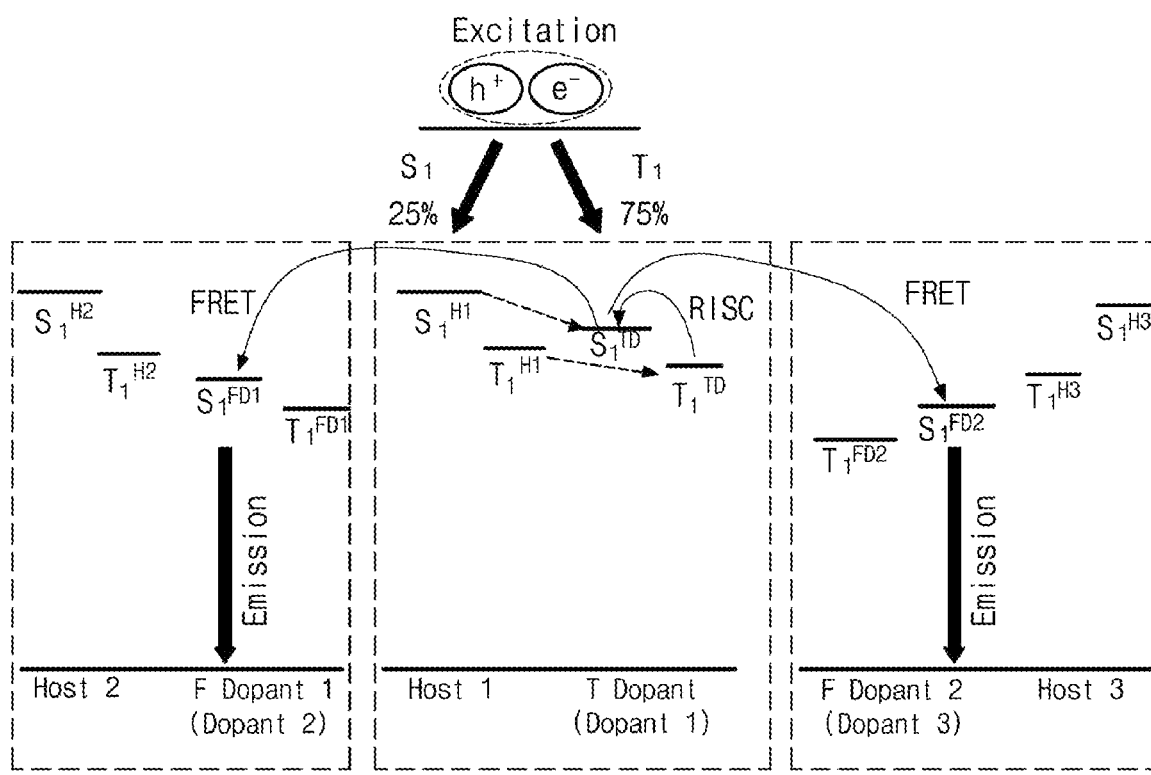
FIG. 10 is a schematic diagram illustrating a luminous mechanism by energy level bandgaps among luminous materials in accordance with another exemplary embodiment of the present disclosure.

An OLED having a triple-layered EML will be explained. FIG. 9 is a schematic cross-sectional view illustrating an organic light emitting diode having a triple-layered EML in accordance with another exemplary embodiment of the present disclosure. FIG. 10 is a schematic diagram illustrating luminous mechanism by energy level bandgap among luminous materials in accordance with another exemplary embodiment of the present disclosure.

As illustrated in FIG. 9, an OLED 500 in accordance with the fourth embodiment of the present disclosure includes first and second electrodes 510 and 520 facing each other and an emitting unit 530 as an emission layer disposed between the first and second electrodes 510 and 520.

In one exemplary embodiment, the emitting unit 530 includes an HIL 540, an HTL 550, and EML 560, an ETL 570 and an EIL 580 each of which is laminated sequentially over the first electrode 510. In addition, the emitting unit 530 may further include an EBL 555 as a first exciton blocking layer disposed between the HTL 550 and the EML 560, and/or an HBL 575 as a second exciton blocking layer disposed between the EML 560 and the ETL 570.

As described above, the first electrode 510 may be an anode and may include, but is not limited to, a conductive material having a relatively large work function values such as ITO, IZO, SnO, ZnO, ICO, AZO, and the like. The second electrode 520 may be a cathode and may include, but is not limited to, a conductive material having a relatively small work function values such as Al, Mg, Ca, Ag, alloy thereof or combination thereof.

The HIL 540 is disposed between the first electrode 510 and the HTL 550. The HIL 540 may include, but is not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 540 may be omitted in compliance with the structure of the OLED 500.

The HTL 550 is disposed adjacently to the EML 560 between the first electrode 510 and the EML 560. The HTL 550 may include, but is not limited to, aromatic amine compounds such as TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EML 560 includes a first EML (EML1) 562, a second EML (EML2) 564 and a third EML (EML3) 566. The EML1 562 is disposed between the EBL 555 and the HBL 575, the EML2 564 is disposed between the EBL 555 and the EML1 562 and the EML3 566 is disposed between the EML1 562 and the HBL 575. The configuration and energy levels among the luminous materials in the EML 560 will be explained in more detail below.

The ETL 570 is disposed between the EML 560 and the EIL 580. In one exemplary embodiment, the ETL 570 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like. As an example, the ETL 570 may include, but is not limited to, Alq$_3$, PBD, spiro-PBD, Liq, TPBi, BAlq, Bphen. NBphen. BCP, TAZ, NTAZ, TpPyPB, TmPPPyTz, PFNBr and/or TPQ.

The EIL 580 is disposed between the second electrode 520 and the ETL 570. In one exemplary embodiment, the EIL 580 may include, but is not limited to, an alkali halide such as LiF, CsF, NaF, BaF$_2$ and the like, and/or an organic metal compound such as lithium benzoate, sodium stearate, and the like.

The EBL 555 may be disposed between the HTL 550 and the EML 560 for controlling and preventing electron transportations between the HTL 550 and the EML 560. As an example, The EBL 555 may include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPe, DNTPD, TDAPB, 2,8-bis(9-phenyl-9H-carbazol-3-yl)dibenzo[b,d]thiophene and/or 3,6-bis(N-carbazolyl)-N-phenyl-carbazole.

The HBL 575 may be disposed between the EML 560 and the ETL 570 for preventing hole transportations between the EML 560 and the ETL 570. In one exemplary embodiment, the HBL, 575 may include, but is not limited to, oxadiazole-based compounds, triazole-based compounds, phenanthroline-based compounds, benzoxazole-based compounds, benzothiazole-based compounds, benzimidazole-based compounds, and triazine-based compounds. As an example, the HBL 575 may include a compound having a relatively low HOMO energy level compared to the emitting material in EML 560. The HBL 575 may include, but is not limited to, BCP, BAlq, Alq$_3$, PBD, spiro-PBD, Liq, B3PYMPM, DPEPO, 9-(6-(9H-carbazol-9-yl)pyridine-3-yl)-9H-3,9'-bi-carbazole and combination thereof.

The EML1 562 includes a first dopant (T dopant) having a delayed fluorescent property, i.e. the organic compound having the structure of any one in Chemical Formulae 1, 4, 7, 8 and 11. Each of the EML2 564 and the EML3 566 includes a second dopant (a first fluorescent or phosphorescent dopant, F dopant 2) and a third dopant (a second fluorescent or phosphorescent dopant). Each of the EML1 562, EML2 564 and EML3 566 further includes a first host, a second host and a third host, respectively.

In accordance with this embodiment, the singlet energy as well as the triplet energy of the first dopant (T dopant) as the delayed fluorescent material, i.e. the organic compound having the structure of any one in Chemical Formulae 1, 4, 7, 8 and 11 in the EML1 562 can be transferred to the second and third dopants (F dopants 1 and 2) each of which is included in the EML2 564 and EML3 566 disposed adjacently to the EML1 562 by FRET energy transfer mechanism. Accordingly, the ultimate emission occurs in the second and third dopants in the EML2 564 and the EML3 566.

In other words, the triplet exciton energy of the first dopant is converted upwardly to the singlet exciton energy of its own in the EML1 562 by RISC mechanism, then the singlet exciton energy of the first dopant is transferred to the singlet exciton energy of the second and third dopants in the EML2 564 and the EML3 566 because the excited state singlet energy level $S_1^{TD}$ of the first dopant is higher than each of the excited state singlet energy levels $S_1^{FD1}$ and $S_1^{FD2}$ of the second and third dopants (See, FIG. 10). The singlet exciton energy of the first dopant in the EML1 562 is transferred to the second and third dopants in the EML2 564 and the EML3 566 which are disposed adjacently to the EML1 562 by FRET mechanism.

The second and third dopants in the EML2 564 and EML3 566 can emit light using the singlet exciton energy and the triplet exciton energy derived from the first dopant. Each of the second and third dopants may have narrower FWHM compared to the first dopant. As the exciton energy, which is generated at the first dopant as the delayed fluorescent material in the EML1 562, is transferred to the second and third dopants in the EML2 564 and the EML3 566, a hyper-fluorescence can be realized. In this case, the first dopant only acts as transferring energy to the second and third dopants. The EML1 562 including the first dopant is not involved in the ultimate emission process. Substantial light emission is occurred in the EML2 564 and in the EML3 566 each of which includes the second dopant and the third dopant with a narrow FWHM. Accordingly, the OLED 500 can enhance its quantum efficiency and improve its color purity due to narrow FWHM. As an example, each of the second and third dopants may have an emission wavelength range having a large overlapping area with an absorption wavelength range of the first dopant, so that exciton energy of the first dopant may be transferred efficiently to each of the second and third dopants.

In this case, it is necessary to adjust properly energy levels among the hosts and the dopants in the EML1 562, the EML2 564 and the EML3 566. As illustrated in FIG. 10, each of excited state singlet energy levels $S_1^{H1}$, $S_1^{H2}$ and $S_1^{H3}$ and excited triplet energy levels $T_1^{H1}$, $T_1^{H2}$ and $T_1^{H3}$ of the first to third hosts should be higher than each of the excited state singlet energy level $S_1^{TD}$ and the excited state triplet energy level $T_1^{TD}$ of the first dopant as the delayed fluorescent material, respectively.

For example, when each of the excited triplet energy levels $T_1^{H1}$, $T_1^{H2}$ and $T_1^{H3}$ of the first to third hosts is not high enough than the excited state triplet energy level $T_1^{TD}$ of the first dopant, the triplet exciton of the first dopant may be reversely transferred to the excited state triplet energy levels $T_1^{H1}$, $T_1^{H2}$ and $T_1^{H3}$ of the first to third hosts, which cannot utilize triplet exciton energy. Accordingly, the excitons of the triplet state level $T_1^{TD}$ of the first dopant may be quenched as a non-emission and the triplet state excitons of the first dopant cannot be involved in the emission. As an example, each of the excited state triplet energy levels $T_1^{H1}$, $T_1^{H2}$ and $T_1^{H3}$ of the first to third hosts may be higher than the excited state triplet energy level $T_1^{TD}$ of the first dopant by at least about 0.2 eV.

In addition, it is necessary for the EML 560 to implement high luminous efficiency and color purity as well as to transfer exciton energy efficiently from the first dopant, which is converted to ICT complex state by RISC mechanism in the EML1 562, to the second and third dopants each of which is the fluorescent or phosphorescent material in the EML2 564 and the EML3 566. In order to realize such an OLED 500, the excited state triplet energy level $T_1^{TD}$ of the first dopant in the EML1 562 is higher than each of excited state triplet energy levels $T_1^{FD1}$ and $T_1^{FD2}$ of the second and third dopants. In one exemplary embodiment, the excited state singlet energy level $S_1^{TD}$ of the first dopant may be higher than each of excited state singlet energy levels $S_1^{FD1}$ and $S_1^{FD2}$ of the second and third dopants as fluorescent material.

Moreover, the exciton energy, which is transferred from the first dopant to each of the second and third dopants, should not be transferred to the second and third hosts in order to realize efficient light emission. As an example, each of the excited singlet energy levels $S_1^{H2}$ and $S_1^{H3}$ of the second and third hosts may be higher than each of the excited state energy level $S_1^{FD1}$ and $S_1^{FD2}$ of the second and third dopants, respectively. In one exemplary embodiment, the energy level bandgap between the excited state singlet energy level $S_1^{TD}$ and the excited state triplet energy level $T_1^{TD}$ of the first dopant may be equal to or less than about 0.3 eV in order to implement a delayed fluorescence.

In addition, an energy level bandgap ($|HOMO^{H1}-HOMO^{TD}|$) between a HOMO energy level ($HOMO^{H1}$) of the first host and a HOMO energy level ($HOMO^{TD}$) of the first dopant, or an energy level bandgap ($|LUMO^{H1}-LUMO^{TD}|$) between a LUMO energy level ($LUMO^{H1}$) of the first host and a LUMO energy level ($LUMO^{TD}$) of the first dopant may be equal to or less than about 0.5 eV.

Each of the EML1 562, the EML2 564 and the EML3 566 may include the first host, the second host and the third host, respectively. For example, each of the first to third hosts may be the same or different from each other. For Example, each of the first to third hosts may independently include, but is not limited to, mCP-CN, CBP, mCBP, mCP, DPEPO, PPT, TmPyPB, PYD-2Cz, DCzDBT, DCzTPA, pCzB-2CN, mCzB-2CN, TSPO1, CCP, 9-(4-(9H-carbazol-9-yl)phenyl)-9H-3,9'-bicarbazole, 9-(3-(9H-carbazol-9-yl)phenyl)-9H-3,9'-bicarbazole, 9-(6-(9H-carbazol-9-yl)pyridin-3-yl)-9H-3,9'-bicarbazole and/or 4-(3-(triphenylen-2-yl)phenyl)dibenzo[b,d]thiophene.

Each of the second and third dopants may have narrow FWHM and have luminous spectrum having large overlapping area with the absorption spectrum of the first dopant. As an example, each of the second and third dopants may independently include, but is not limited to, an organic compound having a quinolino-acridine core such as 5,12-dimethylquinolino[2,3-b]acridine-7,14(5H, 12H)-dione, 5,12-diethylquinolino[2,3-b]acridine-7,14(5H, 12H)-dione, 5,12-dibutyl-3,10-difluoroquinolino[2,3-b]acridine-7,14 (5H, 12H)-dione, 5,12-dibutyl-3,10-bis(trifluoromethyl)quinolino[2,3-b]acridine-7,14(5H, 12H)-dione, 5,12-dibutyl-2,3,9,10-tetrafluoroquinolino[2,3-b]acridine-7,14(5H, 12H)-dione, DCJTB and any metal complexes which can emit light of green color.

In one exemplary embodiment, each of the first to third hosts in the EML1 562, EML2 564 and the EML3 566 may have weigh ratio equal to or more than the weight ratio of the first to third dopants within the same EMLs 562, 564 and 566. The weight ratio of the first dopant in the EML1 562 may be more than each of the weight ratio of the second and third dopants in the EML2 564 and the EML3 566. In this case, it is possible to transfer enough exciton energy from the first dopant in the EML1 562 to the second and third dopants in the EML2 564 and the EML3 566 through FRET energy transfer mechanism.

Particularly, the weight ratio of the first host may be equal to or more than the weight ratio of the first dopant in the EML1 562. As an example, the EML1 562 may include the first host of about 50 to about 99% by weight, preferably about 60 to about 90% by weight, and more preferably about 60 to about 80% by weight, and the first dopant of about 1 to about 50% by weight, preferably about 10 to about 40% by weight, and more preferably about 20 to about 40% by weight.

Each of the weight ratios of the second and thirds hosts may be larger than each of the weight ratios of the second and third dopants in the EML2 564 and the EML3 566. As an example, each of the EML2 564 and EML3 566 may include the second or third host, but is not limited to, about 90 to about 99% by weight, and preferably about 95 to about 99% by weight, and the second or third dopant, but is not limited to, about 1 to about 10% by weight, and preferably about 1 to about 5% by weight.

The EML1 562 may be laminated with a thickness of, but is not limited to, about 2 nm to about 100 nm, preferably about 2 nm to about 30 nm, and preferably about 2 to about 20 nm. Each of the EML2 564 and the EML3 566 may be laminated with a thickness of, but is not limited to, about 5 nm to about 100 nm, preferably about 10 nm to about 30 nm, and more preferably about 10 nm to about 20 nm.

When the EML2 564 is disposed adjacently to the EBL 555 in one exemplary embodiment, the second host, which is included in the EML2 564 together with the second dopant, may be the same material as the EBL 555. In this case, the EML2 564 may have an electron blocking function as well as an emission function. In other words, the EML2 564 can act as a buffer layer for blocking electrons. In one embodiment, the EBL 555 may be omitted where the EML2 564 may be an electron blocking layer as well as an emitting material layer.

When the EML3 566 is disposed adjacently to the HBL 575 in another exemplary embodiment, the third host, which is included in the EML3 566 together with the third dopant, may be the same material as the HBL 575. In this case, the EML3 566 may have a hole blocking function as well as an emission function. In other words, the EML3 566 can act as a buffer layer for blocking holes. In one embodiment, the HBL 575 may be omitted where the EML3 566 may be a hole blocking layer as well as an emitting material layer.

In still another exemplary embodiment, the second host in the EML2 564 may be the same material as the EBL 555 and the third host in the EML3 566 may be the same material as the HBL 575. In this embodiment, the EML2 564 may have an electron blocking function as well as an emission function, and the EML3 566 may have a hole blocking function as well as an emission function. In other words, each of the EML2 564 and the EML3 566 can act as a buffer layer for blocking electrons or hole, respectively. In one embodiment, the EBL 555 and the HBL 575 may be omitted where the EML2 564 may be an electron blocking layer as well as an emitting material layer and the EML3 566 may be a hole blocking layer as well as an emitting material layer.

Figure 11:
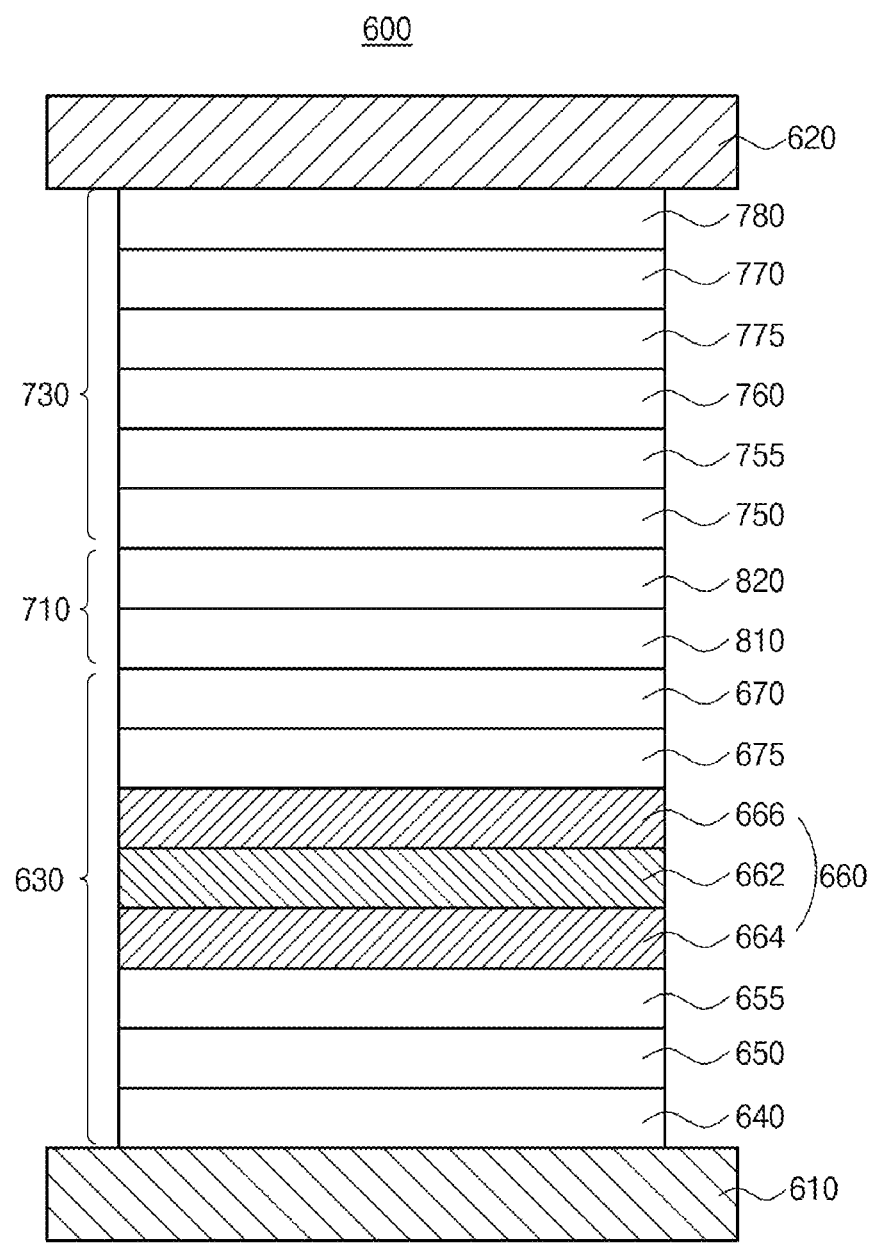
FIG. 11 is a schematic cross-section view illustrating an organic light emitting diode in accordance with another exemplary embodiment of the present disclosure.

In the above embodiments, the OLED having only one emitting unit is described. Unlike the above embodiment, the OLED may have multiple emitting units so as to form a tandem structure. FIG. 11 is a cross-sectional view illustrating an organic light emitting diode in accordance with still another embodiment of the present disclosure.

As illustrated in FIG. 11, the OLED 600 in accordance with the fifth embodiment of the present disclosure includes first and second electrodes 610 and 620 facing each other, a first emitting unit 630 as a first emission layer disposed between the first and second electrodes 610 and 620, a second emitting unit 730 as a second emission layer disposed between the first emitting unit 630 and the second electrode 620, and a charge generation layer 710 disposed between the first and second emitting units 630 and 730.

As mentioned above, the first electrode 610 may be an anode and include, but is not limited to, a conductive material having a relatively large work function values. As an example, the first electrode 610 may include, but is not limited to, ITO, IZO, SnO, ZnO, ICO, AZO, and the like. The second electrode 620 may be a cathode and may include, but is not limited to, a conductive material having a relatively small work function values such as Al, Mg, Ca, Ag, alloy thereof or combination thereof. Each of the first and second electrodes 610 and 620 may be laminated with a thickness of, but is not limited to, about 30 nm to about 300 nm.

The first emitting unit 630 includes a HIL 640, a first HTL (a lower HTL) 650, a lower EML 660 and a first ETL (a lower ETL) 670. The first emitting unit 630 may further include a first EBL (a lower EBL) 655 disposed between the first HTL 650 and the lower EML 660 and/or a first HBL (a lower HBL) 675 disposed between the lower EML 660 and the first ETL 670.

The second emitting unit 730 includes a second HTL (an upper HTL) 750, an upper EML 760, a second ETL (an upper ETL) 770 and an EIL 780. The second emitting unit 730 may further include a second EBL (an upper EBL) 755 disposed between the second HTL 750 and the upper EML 760 and/or a second HBL (an upper HBL) 775 disposed between the upper EML 760 and the second ETL 770.

At least one of the lower EML 660 and the upper EML 760 may include the organic compound having the structure of any one in Chemical Formulae 1, 4, 7, 8 and 11 and emit green (G) light. As an example, one of the lower and upper EMLs 660 and 760 may emit green (G) light, and the other of the lower and upper EMLs 660 and 760 may emit blue (B) and/or red (R) light. Hereinafter, the OLED 600, where the lower EML 660 emits green light and includes the organic compound having the structure of any one in Chemical Formulae 1, 4, 7, 8 and 11 and the upper EML 760 emits blue and/or red lights, will be explained.

The HIL 640 is disposed between the first electrode 610 and the first HTL 650 and improves an interface property between the inorganic first electrode 610 and the organic first HTL 650. In one exemplary embodiment, the HIL 640 may include, but is not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 640 may be omitted in compliance with a structure of the OLED 600.

Each of the first and second HTLs 650 and 750 may independently include, but is not limited to, TPD, NPD (NPB), CBP, poly-TPD, TFB, TAPC, N-(biphenyl-4-yl)-9, 9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine. Each of the HIL 640 and the first and second HTLs 650 and 750 may be laminated with a thickness of, but is not limited to, about 5 nm to about 200 nm, and preferably about 5 nm to about 100 nm.

Each of the first and second ETLs 670 and 770 facilitates electron transportations in the first emitting unit 630 and the second emitting unit 730, respectively. Each of the first and second ETLs 670 and 770 may independently include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like, respectively. As an example, each of the first and second ETLs 670 and 770 may independently include, but is not limited to, Alq$_3$, PBD, spiro-PBD, Liq, TPBi, BAlq, Bphen, NBphen, BCP, TAZ, NTAZ, TpPyPB, TmPPPyTz, PFNBr and/or TPQ, respectively.

The EIL 780 is disposed between the second electrode 620 and the second ETL 770, and can improve physical properties of the second electrode 620 and therefore, can enhance the life span of the OLED 600. In one exemplary embodiment, the EIL 780 may include, but is not limited to, an alkali halide such as LiF, CsF, NaF, BaF$_2$ and the like, and/or an organic metal compound such as lithium benzoate, sodium stearate, and the like.

As an example, each of the first and second EBLs 655 and 755 may independently include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, DNTPD, TDAPB 2,8-bis(9-phneyl-9H-carbazol-3-yl) dibenzo[b,d]thiophene and/or 3,6-bis(N-carbazolyl)-N-phenyl-carbazole, respectively.

Each of the first and second HBLs 675 and 775 may independently include, but is not limited to, oxadiazole-based compounds, triazole-based compounds, phenanthroline-based compounds, benzoxazole-based compounds, benzothiazole-based compounds, benzimidazole-based compounds, and triazine-based compounds. As an example, each of the first and second HBLs 675 and 775 may independently include, but is not limited to, BCP, BAlq, Alga, PBD, spiro-PBD, Liq, B3PYMPM, DPEPO, 9-(6-(9H-carbazol-9-yl)pyridine-3-yl)-9H-3,9'-bicarbazole and combination thereof, respectively.

In one exemplary embodiment, when the upper EML 760 emits red light, the upper EML 760 may be, but is not limited to, a phosphorescent material layer including a host such as CBP and the like and at least one dopant selected from the group consisting of PIQIr(acac) (bis(1-phenylisoquinoline) acetylacetonate iridium). PQIr(acac) (bis(1-phenylquinoline)acetylacetonate iridium), PQIr (tris(1-phenylquinoline) iridium) and PtOEP(octaethylporphyrin platinum). Alternatively, the upper EML 760 may be a fluorescent material layer including PBD:Eu(DMB)$_3$(phen), perylene and/or their derivatives. In this case, the upper EML 760 may emit red light having, but is not limited to, emission wavelength ranges of about 600 nm to about 650 nm.

In another exemplary embodiment, when the upper EML 760 emits blue light, the upper EML 760 may be, but is not limited to, a phosphorescent material layer including a host such as CBP and the like and at least one iridium-based dopant. Alternatively, the upper EML 760 may be a fluorescent material layer including any one selected from the group consisting of spiro-DPVBi, spiro-CBP, distrylbenzene (DSB), distrylarylene (DSA), PFO-based polymers and PPV-based polymers. The upper EML 760 may emit light of sky-blue color or deep blue color as well as blue color. In this case, the upper EML 760 may emit red light having, but is not limited to, emission wavelength ranges of about 440 nm to about 480 nm.

In one exemplary embodiment, the second emitting unit 730 may have double-layered EML 760, for example, a blue emitting material layer and a red emitting material layer, in order to enhance luminous efficiency of the red light. In this case, the upper EML 760 may emit light having, but is not limited to, emission wavelength ranges of about 440 nm to about 650 nm.

The charge generation layer (CGL) 710 is disposed between the first emitting unit 630 and the second emitting unit 730. The CGL 710 include an N-type CGL 810 disposed adjacently to the first emitting unit 630 and a P-type CGL 820 disposed adjacently to the second emitting unit 730. The N-type CGL 810 injects electrons into the first emitting unit 630 and the P-type CGL 820 injects holes into the second emitting unit 730.

As an example, the N-type CGL 810 may be a layer doped with an alkali metal such as Li, Na, K and/or Cs and/or an alkaline earth metal such as Mg, Sr, Ba and/or Ra. For example, a host used in the N-type CGL 810 may include, but is not limited to, an organic compound such as Bphen or MTDATA. The alkali metal or the alkaline earth metal may be doped by about 0.01 wt % to about 30 wt %.

The P-type CGL 820 may include, but is not limited to, an inorganic material selected from the group consisting of tungsten oxide (WO$_x$), molybdenum oxide (MoO$_x$), beryllium oxide (Be$_2$O$_3$), vanadium oxide (V$_2$O$_5$) and combination thereof, and/or an organic material selected from the group consisting of NPD, HAT-CN, 2,3,5,6-Tetrafluoro-7,7,8,8-tetracyanoquinodimethane (F4TCNQ), TPD, N,N,N',N'-Tetranaphthalenyl-benzidine (TNB), TCTA, N,N'-dioctyl-3,4,9,10-perylenedicarboximide (PTCDI-C8) and combination thereof.

The lower EML 660 includes a first EML (EML1) 662 disposed between the first EBL 655 and the first HBL 675, a second EML (EML2) 664 disposed between the first EBL 655 and the EML1 662 and a third EML (EML3) 666 disposed between the EML1 662 and the first HBL 675. The EML1 662 includes a first dopant (T dopant) which is a delayed fluorescent material. i.e. the organic compound having the structure of any one in Chemical Formulae 1, 4, 7, 8 and 11. Each of the EML2 664 and the EML3 666 includes a second dopant (a first F dopant) and a third dopant (a second F dopant) each of which is a fluorescent or phosphorescent material, respectively. Each of the EML1 662, the EML2 664 and the EML3 666 includes a first host, a second host and a third host, respectively.

In this case, the singlet exciton energy as well as the triplet exciton energy of the first dopant in the EML1 662 can be transferred to each of the second and third dopants each of which is included in the EML2 664 and EML3 666 disposed adjacently to the EML1 662 by FRET energy transfer mechanism. Accordingly, the ultimate emission occurs in the second and third dopants in the EML2 664 and the EML3 666.

In other words, the triplet exciton energy of the first dopant is converted to the singlet exciton energy of its own in the EML1 662 by RISC mechanism, then the singlet exciton energy of the first dopant is transferred to each of the singlet exciton energy of the second and third dopants because the excited state singlet energy level $S_1^{TD}$ of the first dopant is higher than each of the excited state singlet energy levels $S_1^{FD1}$ and $S_1^{FD2}$ of the second and third dopants (See, FIG. 10).

The second and third dopants in the EML2 664 and EML3 666 can emit light using the singlet exciton energy and the triplet exciton energy derived from the first dopant. Since the second and third dopants have relatively narrow FWHM as compared with the first dopant, the OLED 600 can enhance its luminous efficiency and color purity.

Each of the EML1 662, the EML2 664 and the EML3 666 includes the first host, the second host and the third host, respectively. For example, each of the first to third hosts may be the same or different from each other. As an example, each of the first to third hosts may independently include, but is not limited to, mCP-CN, CBP, mCBP, mCP, DPEPO, PPT, TmPyPB, PYD-2Cz, DCzDBT, DCzTPA, pCzB-2CN, mCzB-2CN, TSPO1, CCP, 9-(4-(9H-carbazol-9-yl)phenyl)-9H-3,9'-bicarbazole, 9-(3-(9H-carbazol-9-yl)phenyl)-9H-3,9'-bicarbazole, 9-(6-(9H-carbazol-9-yl)pyridin-3-yl)-9H-3,9'-bicarbazole and/or 4-(3-(triphenylen-2-yl)phenyl)dibenzo[b,d]thiophene.

Each of the second and third dopants may have narrow FWHM and have luminous spectrum having large overlapping area with the absorption spectrum of the first dopant. As an example, each of the second and third dopants may independently include, but is not limited to, an organic compound having a quinolino-acridine core such as 5,12-dimethylquinolino[2,3-b]acridine-7,14(5H, 12H)-dione, 5,12-diethylquinolino[2,3-b]acridine-7,14(5H, 12H)-dione, 5,12-dibutyl-3,10-di fluoroquinolino[2,3-b]acridine-7,14(5H, 12H)-dione, 5,12-dibutyl-3,10-bis(trifluoromethyl)quinolino[2,3-b]acridine-7,14(5H, 12H)-dione, 5,12-dibutyl-2,3,9,10-tetrafluoroquinolino[2,3-b]acridine-7,14(5H, 12H)-dione, DCJTB and any metal complexes which can emit light of green color.

In this case, the energy levels among the first to third hosts and the first to third dopant within the lower EML 660 are the same as described in FIG. 10.

In one exemplary embodiment, each of the first to third hosts in the EML1 662, EML2 664 and the EML3 666 may have weigh ratio equal to or more than the weight ratio of the first to third dopants within the same EMLs 662, 664 and 666. The weight ratio of the first dopant in the EML1 662 may be more than each of the weight ratio of the second and third dopants in the EML2 664 and the EML3 666. In this case, it is possible to transfer enough exciton energy from the first dopant in the EML1 662 to the second and third dopants in the EML2 664 and the EML3 666 through FRET energy transfer mechanism.

When the EML2 664 is disposed adjacently to the first EBL 655 in one exemplary embodiment, the second host, which is included in the EML2 664 together with the second dopant, may be the same material as the first EBL 655. In this case, the EML2 664 may have an electron blocking function as well as an emission function. In other words, the EML2 664 can act as a buffer layer for blocking electrons. In one embodiment, the first EBL 655 may be omitted where the EML2 664 may be an electron blocking layer as well as an emitting material layer.

When the EML3 666 is disposed adjacently to the first HBL 675 in another exemplary embodiment, the third host, which is included in the EML3 666 together with the third dopant, may be the same material as the first HBL 675. In this case, the EML3 666 may have a hole blocking function as well as an emission function. In other words, the EML3 666 can act as a buffer layer for blocking holes. In one embodiment, the first HBL 675 may be omitted where the EML3 666 may be a hole blocking layer as well as an emitting material layer.

In still another exemplary embodiment, the second host in the EML2 664 may be the same material as the first EBL 655 and the third host in the EML3 666 may be the same material as the first HBL 675. In this embodiment, the EML2 664 may have an electron blocking function as well as an emission function, and the EML3 666 may have a hole blocking function as well as an emission function. In other words, each of the EML2 664 and the EML3 666 can act as a buffer layer for blocking electrons or hole, respectively. In one embodiment, the first EBL 655 and the first HBL 675 may be omitted where the EML2 664 may be an electron blocking layer as well as an emitting material layer and the EML3 666 may be a hole blocking layer as well as an emitting material layer.

In an alternative embodiment, the lower EML 660 may have a single-layered structure as illustrated in FIGS. 2 and 5. In this case, the lower EML 660 may include a host and a first dopant which may be a delayed fluorescent material, i.e. the organic compound having the structure of any one in Chemical Formulae 1, 4, 7, 8 and 11. Alternatively, the lower EML 660 may include a host, a first dopant which may be a delayed fluorescent material and a second dopant which may be a fluorescent or phosphorescent material.

In another alternative embodiment, the lower EML 660 may have a double-layered structure as illustrated in FIG. 7. In this case, the lower EML 660 may include a first EML and a second EML. The first EML may include a first host and a first dopant which may be a delayed fluorescent material, i.e. the organic compound having the structure of any one in Chemical Formulae 1, 4, 7, 8 and 11, and the second EML may include a second host and a second dopant which may be a fluorescent or phosphorescent material.

In another exemplary embodiment, an OLED of the present disclosure may further includes a third emitting unit disposed between the second emitting unit 730 and the second electrode 620 and a second CGL disposed between the second emitting unit 730 and the third emitting unit. In this case, at least one of the first emitting unit 630, the second emitting unit 730 and the third emitting unit may include the organic compound having the structure of any one in Chemical Formulae 1, 4, 7, 8 and 11 as the dopant.

Synthesis Example 1: Synthesis of Compound 1-2

(1) Synthesis of Intermediate A1

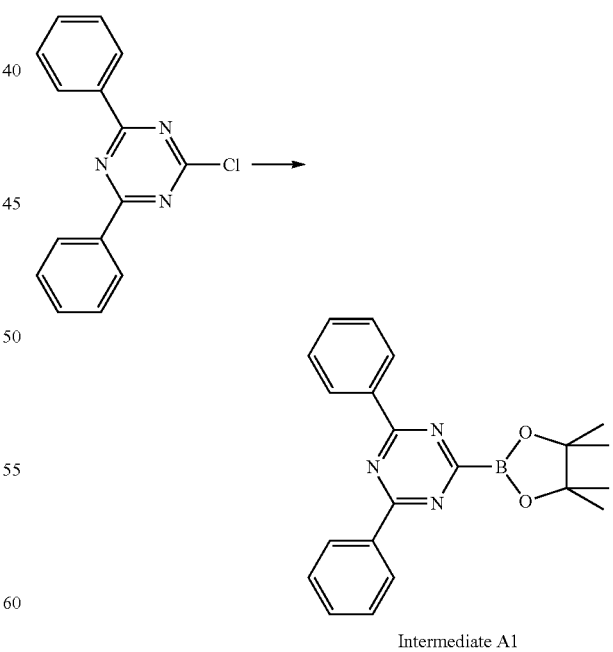

Intermediate A1

10 g (1 equivalent) of 2-chloro-4,6-diphenyl-1,3,5-triazine was dissolved in 80 mL of 1,4-dioxane with stirring under nitrogen atmosphere. 28.46 g (3 equivalents) of bis(pinacolato)diboron, 1 g (0.03 equivalent) of tris(dibenzylideneacetone) dipalladium (0) (Pd$_2$(dba)$_3$), 0.24 g (0.1 equivalent) of 2-dicyclohexylphosphino-2',4',6'-triisopropylbiphenyl (Xphos) and 11 g (3 equivalents) of potassium acetate were added into the solution, and then the solution was refluxed with stirring for more than 12 hours to proceed a reaction. After the reaction was completed, the solution was cooled down to room temperature, was extracted with ethyl acetate and distilled water, and then MgSO$_4$ was added into the organic solution to remove moisture. A crude extract was separated and isolated by column chromatography using hexane and ethyl acetate (4:1) as a developing solvent and was re-crystallized to give 10.2 g of Intermediate A1 (yield: 72%).

(2) Synthesis of Intermediate A2

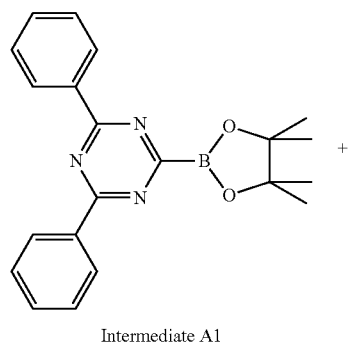

Intermediate A1

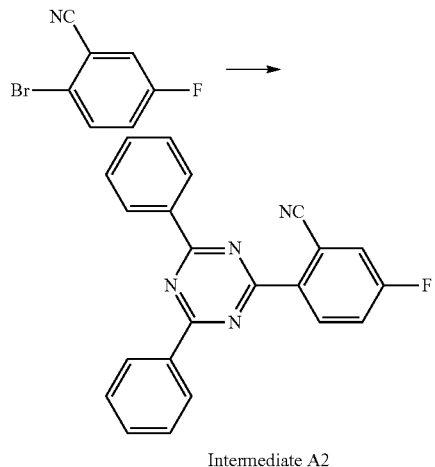

Intermediate A2

19.24 g (5 equivalents) of potassium carbonate was dissolved in 50 mL of water. 10 g (1 equivalent) of Intermediate A1, 8.35 g (1.5 equivalents) of 2-bromo-5-fluorobenzonitrile, 1.61 g (0.05 equivalent) of tetrakis(triphenylphosphine) palladium (0) (Pd(PPh$_3$)$_4$) and 150 mL of THF was added into the aqueous solution, and then the mixed solution was refluxed with stirring for more than 96 hours to proceed to a reaction. After the reaction was completed, the solution was cooled down to room temperature, was extracted with ethyl acetate and distilled water, and then MgSO$_4$ was added into the organic solution to remove moisture. A crude extract was separated and purified by column chromatography using hexane and methylene chloride (3:1) as a developing solvent and was re-crystallized to give 6.4 g of Intermediate A2 (yield: 65%).

(3) Synthesis of Intermediate D1

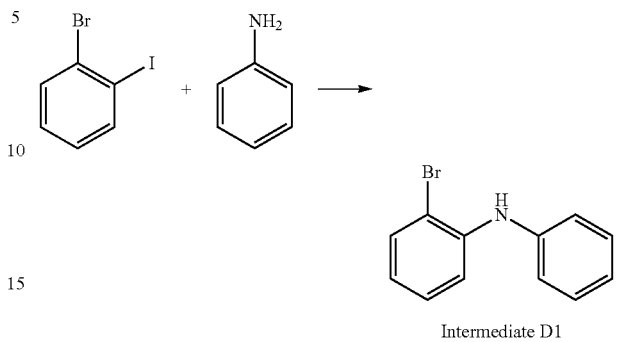

Intermediate D1

10 g (1 equivalent) of 1-bromo-2-iodobenzene, 3.6 mL (1 equivalent) of aniline, 0.4 g (0.05 equivalent) of Pd$_2$(dba)$_3$, 1 mL (0.1 equivalent) of tri-tert-butylphosphine and 5.1 g (5 equivalents) of sodium-tert-butoxide was suspended in 120 mL of toluene, and then the suspension was refluxed with stirring for 20 hours. After the reaction was completed, the suspension was extracted with methylene chloride and distilled water and then organic layer was distilled under reduced pressure. A crude extract was separated and purified by column chromatography using hexane and methylene chloride (5:1) as a developing solvent and was re-crystallized to give 7.5 g of Intermediate D1 (yield: 85%).

(4) Synthesis of Intermediate D2

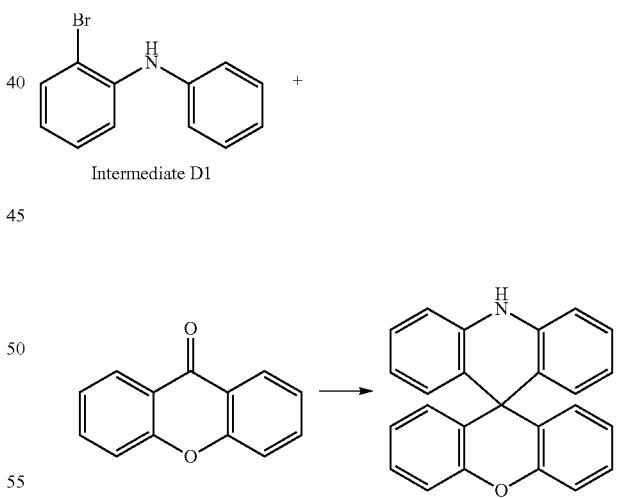

Intermediate D2

7.5 g of intermediate D1 was added into 80 mL of THF under nitrogen atmosphere, and then the solution was cooled down to −78° C. using dry ice. 24 mL of 2.5 M n-BuLi was added into the solution drop wisely and then the solution was stirred for 1 hour. 5.88 g of xanthone dissolved in 50 mL of THF was added into the solution. After removing solvents, 100 mL of acetic acid/HCl (1:10 v/v) was added to give 8.35 g of Intermediate D2 (yield: 80%).

(5) Synthesis of Compound 1-2

Synthesis Example 2: Synthesis of Compound 1-16

(1) Synthesis of Intermediate A3

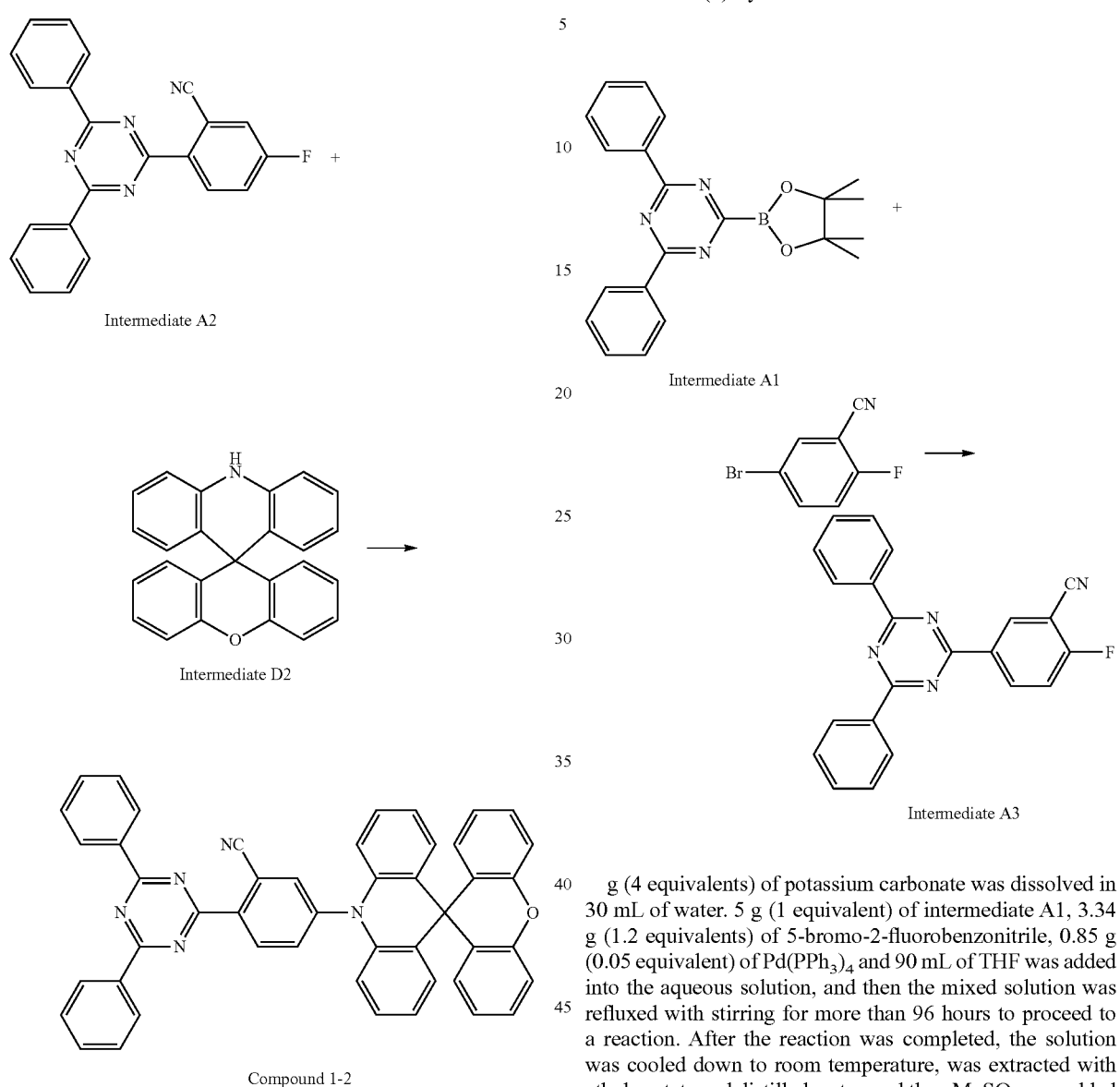

g (4 equivalents) of potassium carbonate was dissolved in 30 mL of water. 5 g (1 equivalent) of intermediate A1, 3.34 g (1.2 equivalents) of 5-bromo-2-fluorobenzonitrile, 0.85 g (0.05 equivalent) of Pd(PPh$_3$)$_4$ and 90 mL of THF was added into the aqueous solution, and then the mixed solution was refluxed with stirring for more than 96 hours to proceed to a reaction. After the reaction was completed, the solution was cooled down to room temperature, was extracted with ethyl acetate and distilled water, and then MgSO$_4$ was added into the solution to remove moisture. A crude extract was separated and purified by column chromatography using hexane and methylene chloride (3:1) as a developing solvent and was re-crystallized to give 3.8 g of Intermediate A3 (yield: 78%).

1.92 g (1.3 equivalents) of Intermediate D2 was placed into a reaction vessel under nitrogen atmosphere, then 50 mL of dimethyl formamide was added into the reaction vessel, and then the solution was stirred. 0.74 g (3 equivalents) of sodium hydride (55%) dispersed in paraffin was added into the solution. After the solution was stirred enough to generate hydrogen gas, 1.50 g of intermediate A2 was added into the solution, and the solution was refluxed with stirring for more than 96 hours at 160° C. The solution was cooled down to room temperature, dimethyl formamide was evaporated and then the solution was filtered with toluene. A crude product was separated and purified by column chromatography using hexane and toluene (1:3) as a developing solvent and was re-crystallized to give 1.15 g of white solid Compound 1-2 (yield: 74%).

(2) Synthesis of Intermediate D3

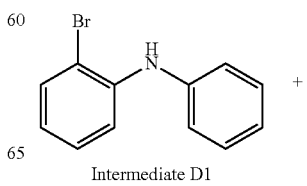

Intermediate D1

-continued

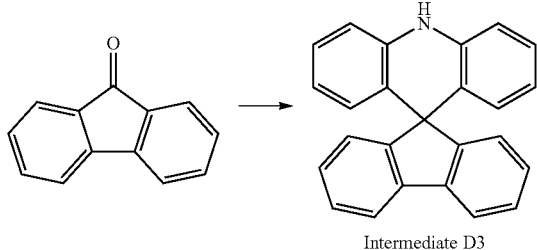

Intermediate D3

7.5 g of intermediate D1 was added into 80 mL of THF under nitrogen atmosphere, and then the solution was cooled down to −78° C. using dry ice. 24 mL of 2.5 M n-BuLi was added into the solution drop wisely and then the solution was stirred for 1 hour. 5.6 g of 9-fluorneone dissolved in 50 mL of THF wad added into the solution. After removing solvents, 100 mL of acetic acid/HCl (1:10 v/v) was added to give 7.19 g of Intermediate D3 (yield: 78%).

(3) Synthesis of Compound 1-16

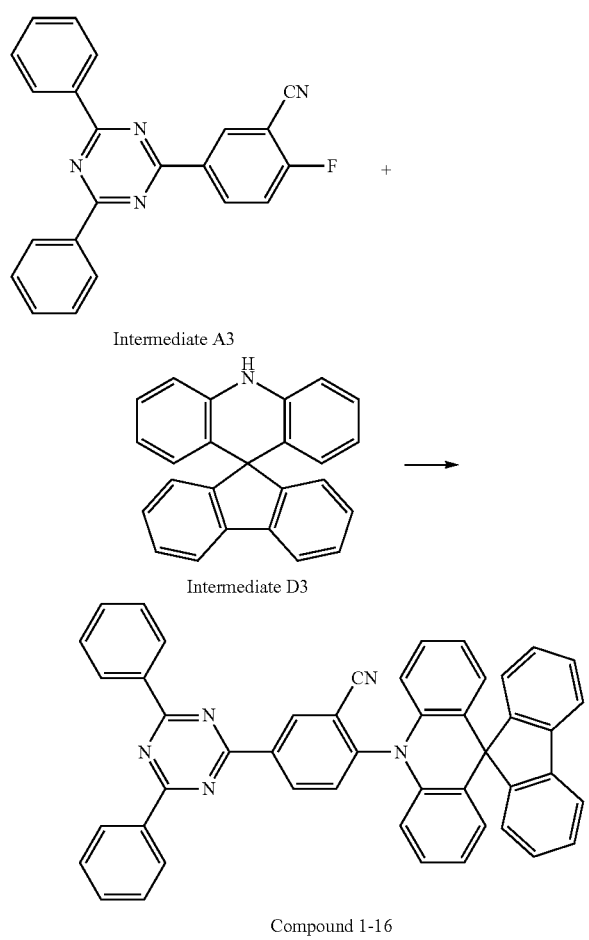

Compound 1-16

2.11 g (1.5 equivalents) of Intermediate D3 was placed into a reaction vessel under nitrogen atmosphere, then 50 mL of dimethyl formamide was added into the reaction vessel, and then the solution was stirred. 0.74 g (3 equivalents) of sodium hydride (55%) dispersed in paraffin was added into the solution. After the solution was stirred enough to generate hydrogen gas, 1.50 g (1 equivalent) of Intermediate A3 was added into the solution, and the solution was refluxed with stirring for more than 96 hours at 160° C. The solution was cooled down to room temperature, dimethyl formamide was evaporated and then the solution was filtered with toluene. A crude product was separated and purified by column chromatography using hexane and toluene (1:3) as a developing solvent and was re-crystallized to give 1.27 g of white solid Compound 1-16 (yield: 82%).

Synthesis Example 3: Synthesis of Compound 1-17

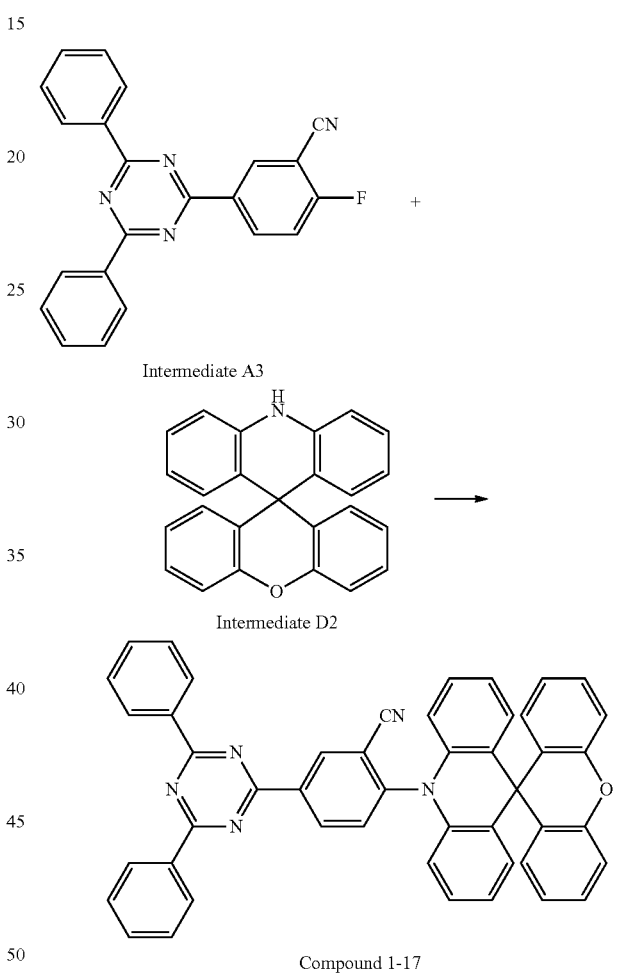

Compound 1-17

1.92 g (1.3 equivalents) of Intermediate D2 was placed into a reaction vessel under nitrogen atmosphere, then 50 mL of dimethyl formamide was added into the reaction vessel, and then the solution was stirred. 0.74 g (3 equivalents) of sodium hydride (55%) dispersed in paraffin was added into the solution. After the solution was stirred enough to generate hydrogen gas, 1.50 g of Intermediate A3 was added into the solution, and the solution was refluxed with stirring for more than 96 hours at 160° C. The solution was cooled down to room temperature, dimethyl formamide was evaporated and then the solution was filtered with toluene. A crude product was separated and purified by column chromatography using hexane and toluene (1:3) as a developing solvent and was re-crystallized to give 1.11 g of white solid Compound 1-17 (yield: 71%).

Synthesis Example 4: Synthesis of Compound 2-1

(1) Synthesis of Intermediate A4

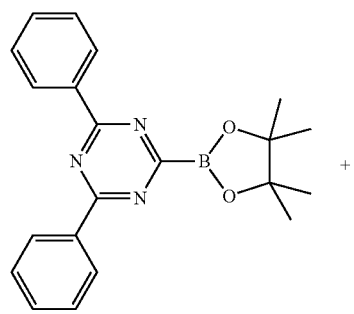

Intermediate A1

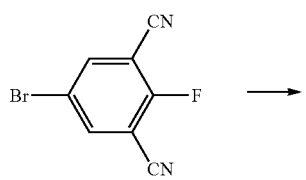

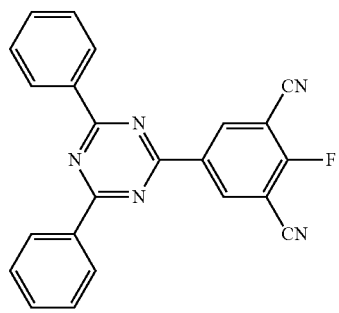

Intermediate A4

8.65 g (4.5 equivalents) of potassium carbonate was dissolved in 30 mL of water. 5 g (1 equivalent) of Intermediate A1, 3.76 g (1.2 equivalents) of 5-bromo-2-fluoroisophthalonitrile, 1.19 g (0.07 equivalent) of Pd(PPh$_3$)$_4$ and 80 mL of THF was added into the aqueous solution, and then the mixed solution was refluxed with stirring for more than 96 hours to proceed to a reaction. After the reaction was completed, the solution was cooled down to room temperature, was extracted with ethyl acetate and distilled water, and then MgSO$_4$ was added into the organic solution to remove moisture. A crude extract was separated and purified by column chromatography using hexane and methylene chloride (5:2) as a developing solvent and was re-crystallized to give 3.8 g of white solid Intermediate A4 (yield: 78%).

(2) Synthesis of Compound 2-1

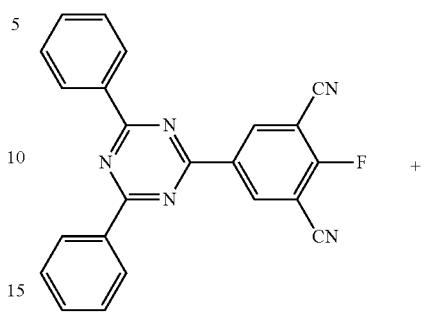

Intermediate A4

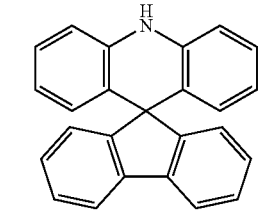

Intermediate D3

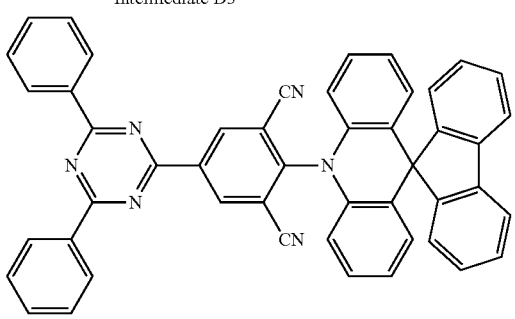

Compound 2-1

2.1 g (1.5 equivalents) of Intermediate D3 was placed into a reaction vessel under nitrogen atmosphere, then 50 mL of dimethyl formamide was added into the reaction vessel, and then the solution was stirred. 0.74 g (3 equivalents) of sodium hydride (55%) dispersed in paraffin was added into the solution. After the solution was stirred enough to generate hydrogen gas, 1.60 g (1 equivalent) of Intermediate A4 was added into the solution, and the solution was refluxed with stirring for more than 96 hours at 160° C. The solution was cooled down to room temperature, dimethyl formamide was evaporated and then the solution was filtered with toluene. A crude product was separated and purified by column chromatography using hexane and toluene (2:5) as a developing solvent and was re-crystallized to give 0.89 g of white solid Compound 2-1 (yield: 57%).

Experimental Example 1: Evaluation of Energy Levels

Energy levels for the Compounds in the Synthesis Examples 1 to 4 were evaluated. Particularly, HOMO energy level, LUMO energy level and energy level bandgap (Eg)) for each of the compounds were evaluated. For the comparison, energy levels for the following referenced compounds were also evaluated. The evaluation results are indicated in the following table 1. As indicated by Table 1, each of Compounds in the Synthesis Examples 1 to 4 showed an adequate HOMO energy level, LUMO energy level and energy level bandgap as used a luminous material, i.e. a dopant in an emitting layer of an organic light emitting diode.

Referenced Compounds

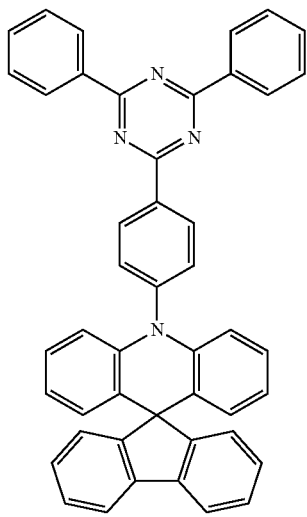

Ref. 1

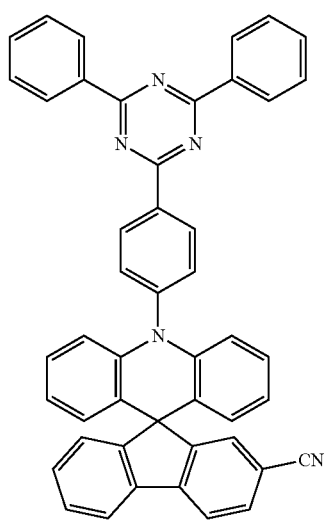

Ref. 2

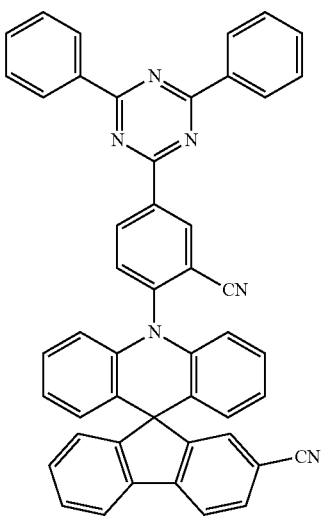

Ref. 3

TABLE 1

Energy Levels of Organic Compound

| Compound | HOMO (eV) | LUMO (eV) | Eg (eV) |
|---|---|---|---|
| Ref. 1 | −5.3 | −2.5 | 2.80 |
| Ref. 2 | −5.2 | −2.4 | 2.84 |
| Ref. 3 | −5.3 | −2.6 | 2.75 |
| Compound 1-2 | −5.3 | −2.7 | 2.68 |
| Compound 1-16 | −5.4 | −2.8 | 2.66 |
| Compound 1-17 | −5.4 | −2.7 | 2.70 |
| Compound 2-1 | −5.5 | −2.8 | 2.72 |

HOMO: Film (100 nm/ITO), by AC3,
LUMO: calculated from film absorption edge;
Eg: LUMO-HOMO Example 1: Fabrication of Organic Light Emitting Diode (OLED)

An organic light emitting diode was fabricated using Compound 1-2 synthesized in the Synthesis Example 1 as a dopant in an emitting material layer (EML). An ITO substrate was treated with UV ozone and then loaded into an evaporation system. The cleaned substrate was transferred to a deposition chamber in order to deposit other layers on the substrate. An organic layer was deposited by evaporation by a heated boat under $10^{-6}$ torr in the following order:

A hole injection layer (HIL) (HAT-CN; 7 nm); a hole transport layer (HTL) (NPB, 55 nm); an electron blocking layer (EBL) (mCBP; 10 nm); an emitting material layer (EML) (4-(3-triphenylen-2-yl)phenyl)dibenzo[b,d]thiophene (host): Compound 1-2 (dopant)=70:30 by weight ratio; 35 nm); a hole blocking layer (HBL) (B3PYMPM; 10 nm); an electron transport layer (ETL) (TPBi; 20 nm); an electron injection layer (EIL) (LiF); and a cathode (Al).

And then, capping layer (CPL) was deposited over the cathode and the device was encapsualted by glass. After deposition of emissve layer and the cathode, the OLED was transferred from the depostion chamber to a dry box for film formation, followed by encapsulation using UV-curable epoxy and moisture getter. The manufactured organic light emitting diode had an emision area of 9 mm².

Examples 2 to 4: Fabrication of OLED

An organic light emitting diode was manufactured as the same process and the same materials as Example 1, except using compound 1-16 (Example 2), Compound 1-17 (Example 3) or Compound 2-1 (Example 4) as the dopant in place of Compound 1-2 in the EML.

Comparative Examples 1 to 3: Manufacture of OLED

An organic light emitting diode was manufactured as the same process and the same materials as Example 1, except using Ref 1 (Comparative Example 1; Ref. 1), Ref. 2 (Comparative Example 2; Ref. 2) or Ref. 3 (Comparative Example 3; Ref. 3) as the dopant in placed of Compound 1-2 in the EML.

Experimental Example 2: Measurement of Luminous Properties of OLED

Each of the organic light emitting diodes fabricated in Examples 1 to 4 and Comparative Examples 1 to 3 was connected to an external power source and then luminous properties for all the diodes were evaluated using a constant current source (KEITHLEY) and a photometer PR650 at room temperature. In particular, current efficiency (cd/A), external quantum efficiency (EQE; %), maximum electroluminescence wavelength (EL $\lambda_{max}$; nm) and color coordinates at a current density of 10 mA/cm$^2$ for the OLEDs were measured. The results thereof are shown in the following Table 2.

TABLE 2

Luminous Properties of OLED

| Sample | cd/A | EQE (%) | EL $\lambda_{max}$ (nm) | CIE |
|---|---|---|---|---|
| Ref. 1 | 3.99 | 2.17 | 480 | (0.168, 0.260) |
| Ref. 2 | 7.88 | 4.80 | 468 | (0.156, 0.224) |
| Ref. 3 | 19.14 | 6.51 | 514 | (0.258, 0.491) |
| Example 1 | 56.90 | 17.40 | 520 | (0.325, 0.512) |
| Example 2 | 73.10 | 21.65 | 528 | (0.330, 0.521) |
| Example 3 | 61.10 | 18.73 | 520 | (0.327, 0.516) |
| Example 4 | 45.64 | 15.03 | 518 | (0.291, 0.546) |

As indicated in Table 2, compared with the OLED using organic compounds having a triazine core as the dopant in the EML of the Comparative Examples, the OLED using the organic compounds of the present disclosure as the dopant in the EML of the Examples improved its current efficiency up to 17.32 times and EQE up to 8.98 times. Compared to the OLED using the compounds having a Spiro moiety substituted with cyano group as the dopant in the Comparative Examples 2 and 3, the OLED using the organic compound of the present disclosure as the dopant in the Examples improved its current efficiency up to 8.28 times and EQE up to 3.51 times. Also, compared the EL $\lambda_{max}$ and CIEs in the Examples with the EL $\lambda_{max}$ and CIEs in the Comparative Examples, it was confirmed that the OLEDs in the Examples 1-4 emit light having a deeper green color. It was confirmed that the OLED can implement hyper-fluorescence having enhanced luminous efficiency and high color purity by applying the organic compounds of the present disclosure into an emission layer.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present disclosure cover the modifications and variations of the present disclosure provided they come within the scope of the appended claims and their equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic compound having the following structure of Chemical Formula 1:

Chemical Formula 1

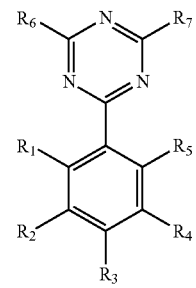

wherein each of $R_1$ to $R_5$ is independently protium, deuterium, tritium, halogen, $C_1$~$C_{10}$ alkyl halide, cyano group, nitro group or a moiety having the following structure of Chemical Formula 2 or Chemical Formula 3, wherein at least one of $R_1$ to $R_5$ is selected from the group consisting of halogen, $C_1$~$C_{10}$ alkyl halide, cyano group and nitro group and at least one of $R_1$ to $R_5$ is a moiety of Chemical Formula 2 or Chemical Formula 3; each of $R_6$ and $R_7$ is independently $C_5$~$C_{30}$ aryl group or $C_4$~$C_{30}$ hetero aryl group:

Chemical Formula 2

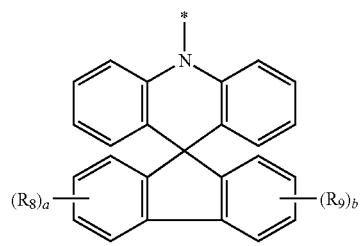

Chemical Formula 3

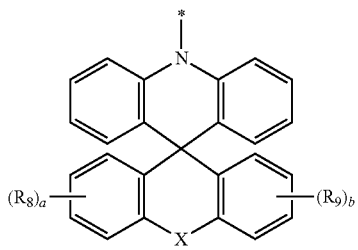

wherein each of $R_8$ and $R_9$ is independently selected from the group consisting of protium, deuterium, tritium, $C_1$~$C_{20}$ alkyl group, $C_1$~$C_{20}$ alkoxy group, $C_1$~$C_{20}$ silyl group, $C_5$~$C_{30}$ aryl group, $C_4$~$C_{30}$ hetero aryl group, $C_5$~$C_{30}$ aryl amino group and $C_4$~$C_{30}$ hetero aryl amino group, wherein each of the $C_5$~$C_{30}$ aryl group, the $C_4$~$C_{30}$ hetero aryl group, the $C_5$~$C_{30}$ aryl amino group and the $C_4$~$C_{30}$ hetero aryl amino group is unsubstituted or substituted with an aromatic group, a hetero aromatic group or a combination thereof, respectively; each of a and b is a number of a substituent and is independently an integer of 1 to 3; X in Chemical Formula 3 is $CR_{11}R_{12}$, $NR_{13}$, $SiR_{14}R_{15}$, oxygen (O) or sulfur (S), wherein each of $R_{11}$ to $R_{15}$ is independently selected from the group consisting of protium, deuterium, tritium, $C_1$~$C_{20}$ alkyl group, $C_1$~$C_{20}$ alkoxy group, $C_1$~$C_{20}$ silyl group, $C_5$~$C_{30}$ aryl group and $C_4$~$C_{30}$ hetero aryl group.

2. The organic compound of claim 1, wherein the organic compound has the following structure of Chemical Formula 4:

Chemical Formula 4

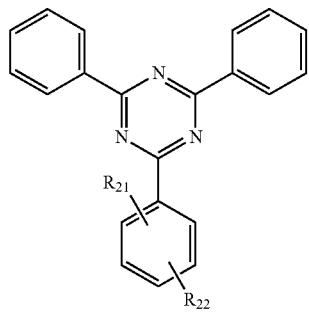

wherein $R_{21}$ is cyano group; and $R_{22}$ is a moiety having the following structure of Chemical Formula 5 or Chemical Formula 6:

Chemical Formula 5

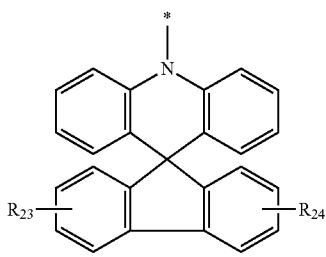

Chemical Formula 6

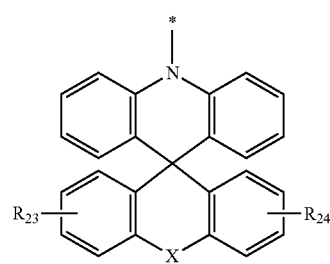

wherein each of $R_{23}$ and $R_{24}$ is independently selected from the group consisting of protium, deuterium, tritium, $C_1$~$C_{20}$ alkyl group, $C_5$~$C_{30}$ aryl group unsubstituted or substituted with an aromatic group, a hetero aromatic group or a combination thereof, and $C_4$~$C_{30}$ hetero aryl group unsubstituted or substituted with an aromatic group, a hetero aromatic group or a combination thereof; X in Chemical Formula 6 is $CR_{11}R_{12}$, $NR_{13}$, $SiR_{14}R_{15}$, oxygen (O) or sulfur (S), wherein each of $R_{11}$ to $R_{15}$ is independently selected from the group consisting of protium, deuterium, tritium, $C_1$~$C_{20}$ alkyl group, $C_1$~$C_{20}$ alkoxy group, $C_1$~$C_{20}$ silyl group, $C_5$~$C_{30}$ aryl group and $C_4$~$C_{30}$ hetero aryl group.

3. The organic compound of claim 2, wherein the organic compound has the following structure of Chemical Formula 7, Chemical Formula 7

Compound 1-1

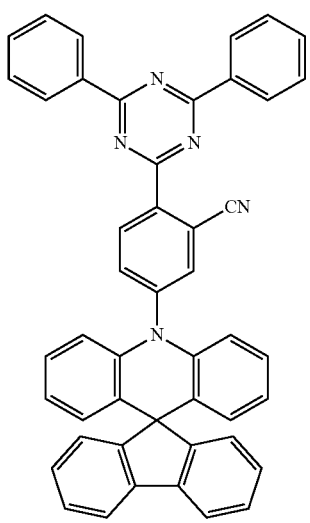

Compound 1-2
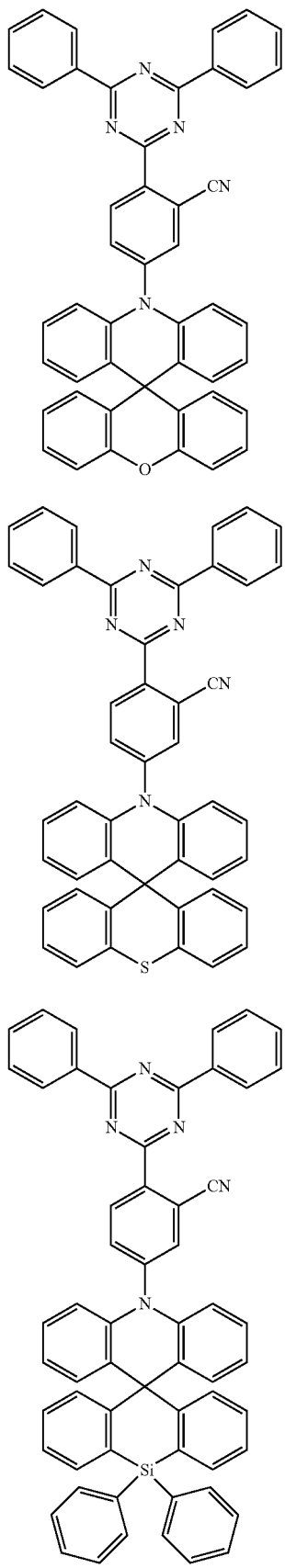
Compound 1-3
Compound 1-4
Compound 1-5
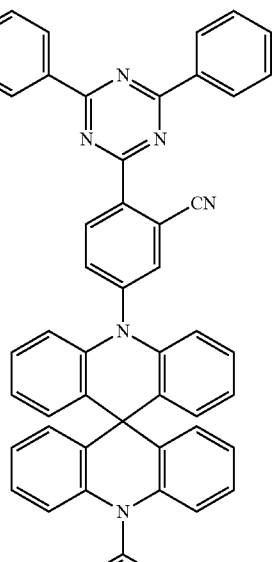
Compound 1-6
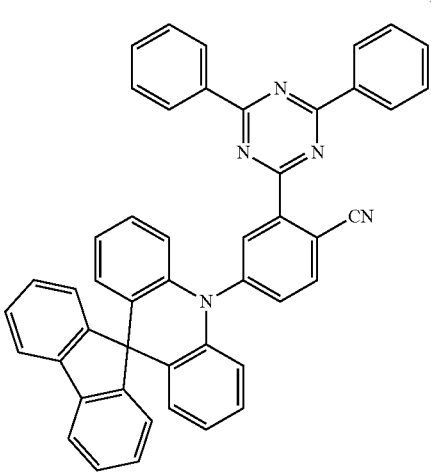
Compound 1-7
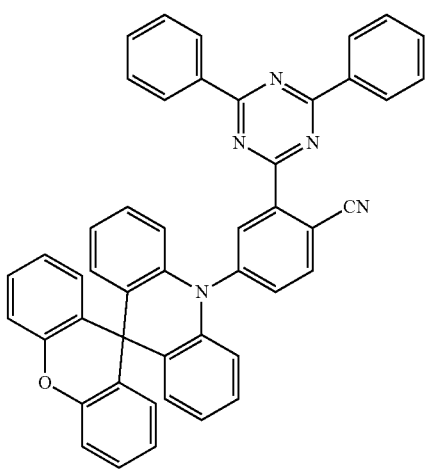

Compound 1-8
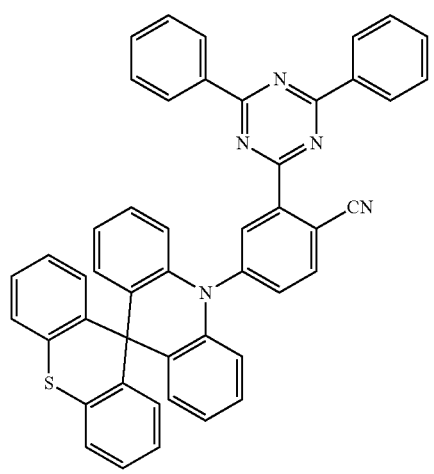
Compound 1-9
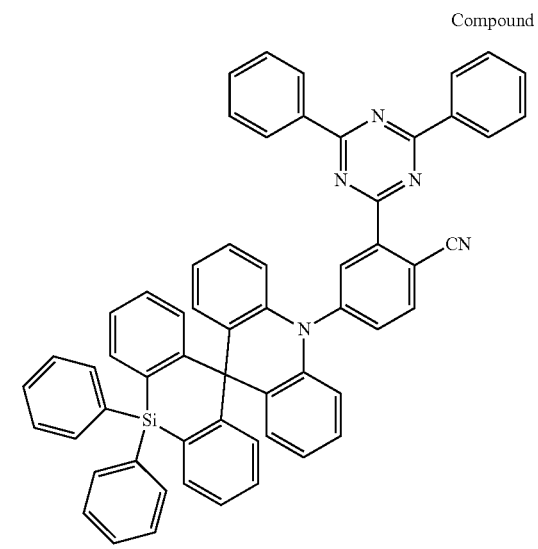
Compound 1-10
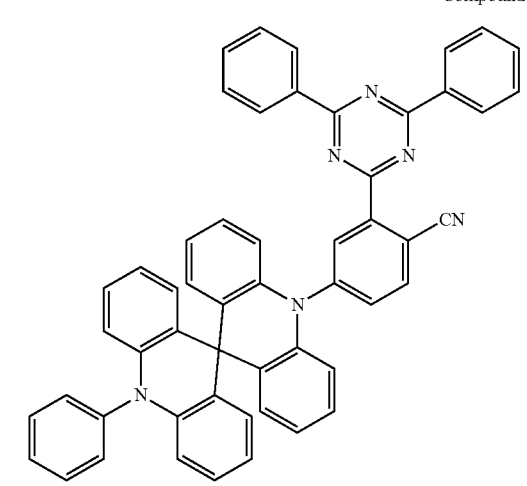
Compound 1-11
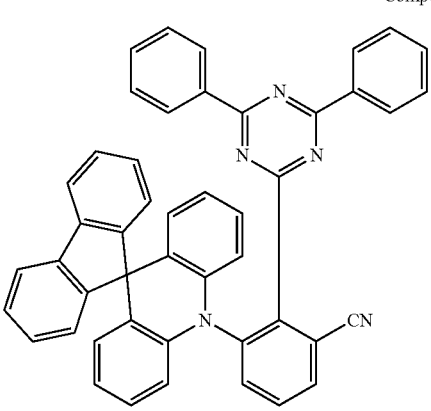
Compound 1-12
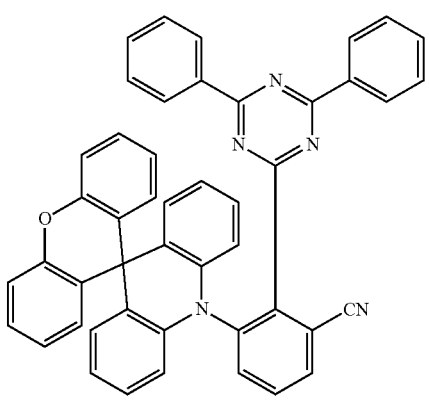
Compound 1-13
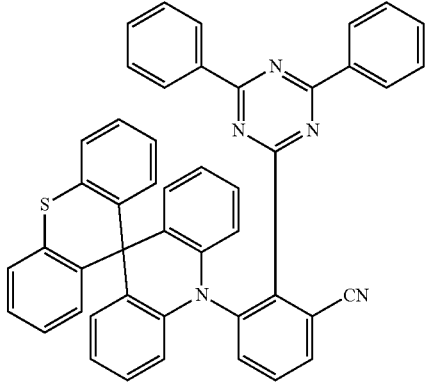
Compound 1-14
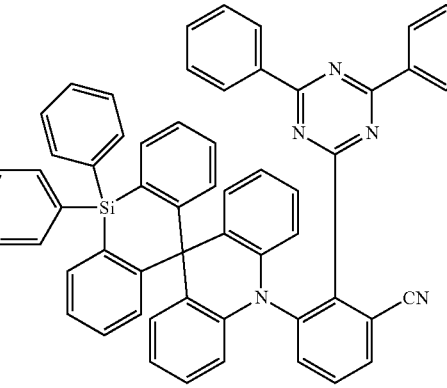

Compound 1-15
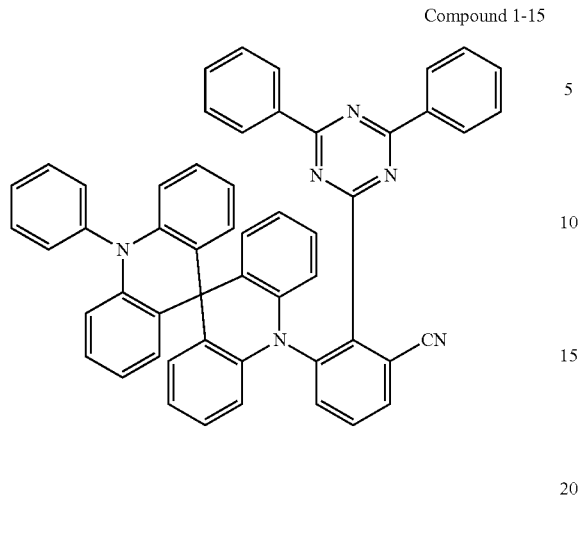
Compound 1-16
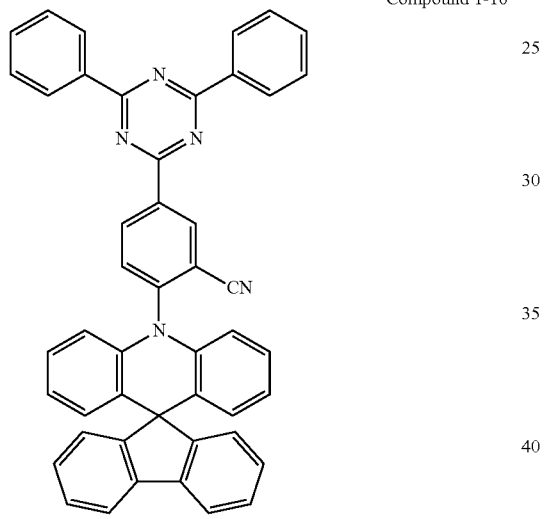
Compound 1-17
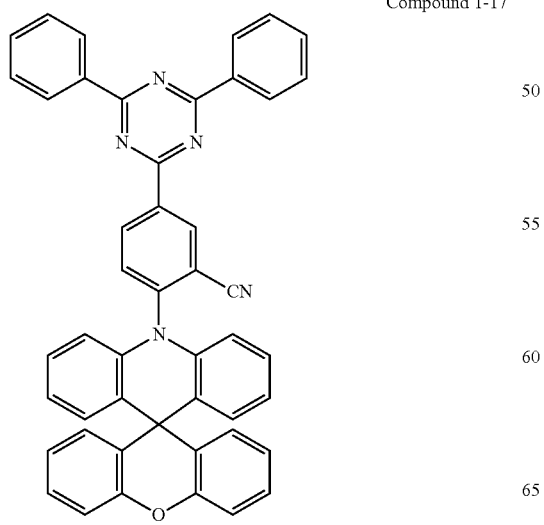
Compound 1-18
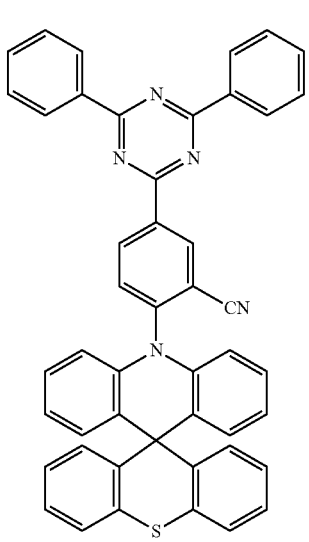
Compound 1-19
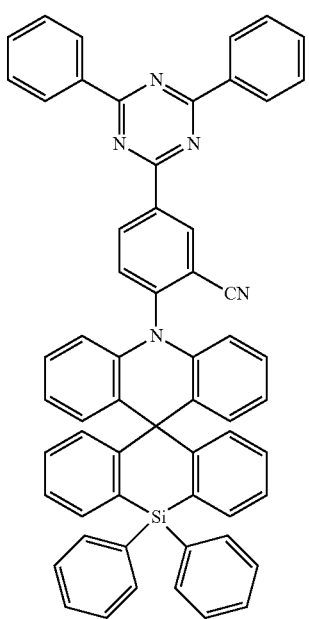

Compound 1-20
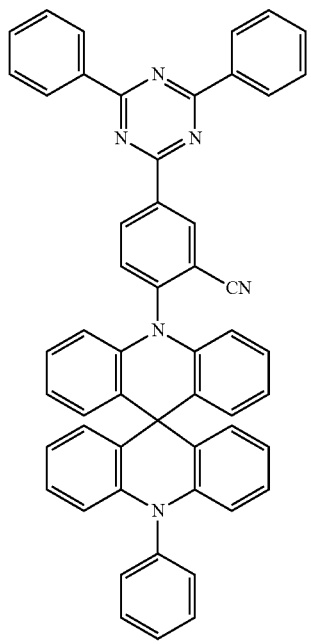
Compound 1-21
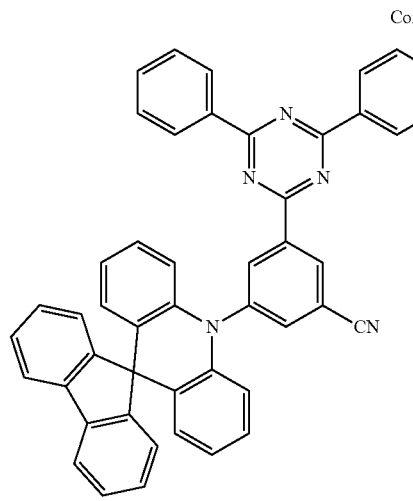
Compound 1-22
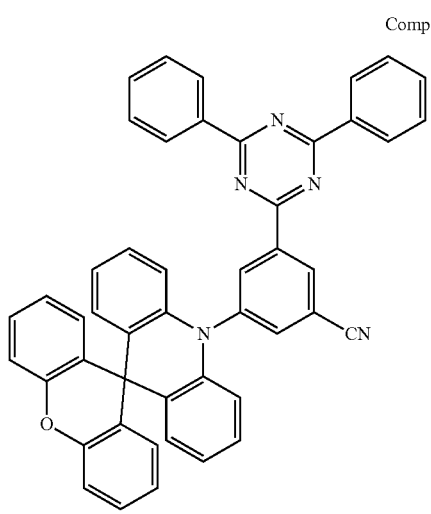
Compound 1-23
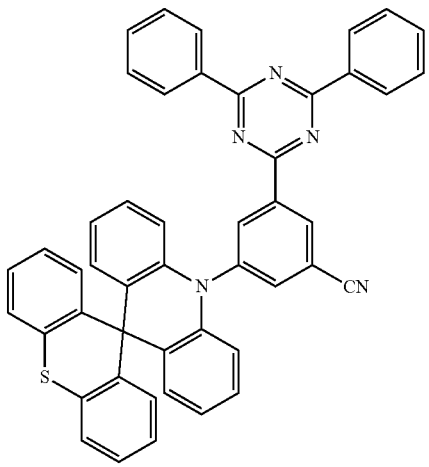
Compound 1-24
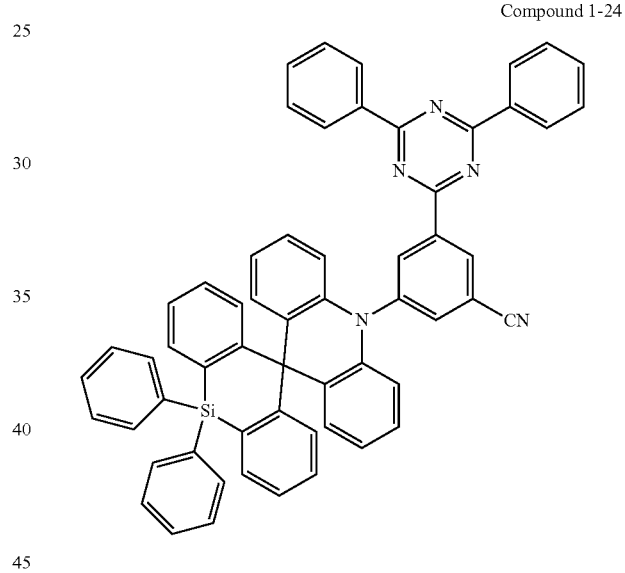
Compound 1-25
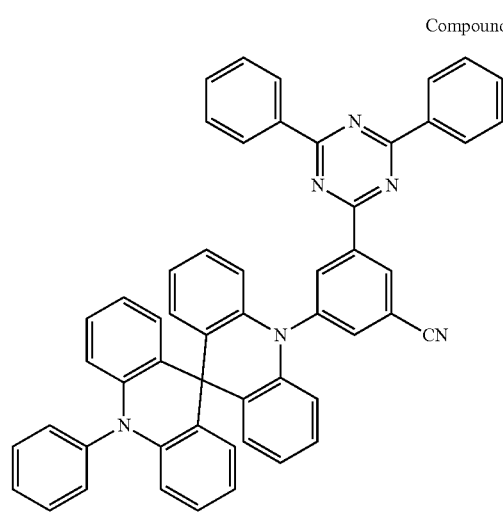

Compound 1-26
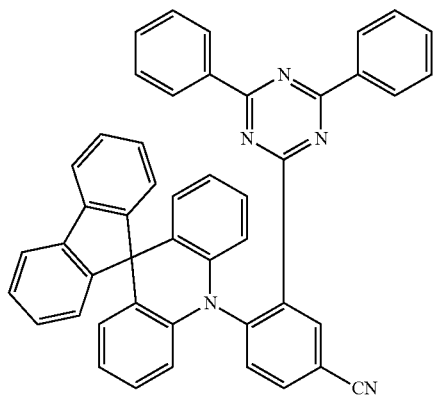
Compound 1-27
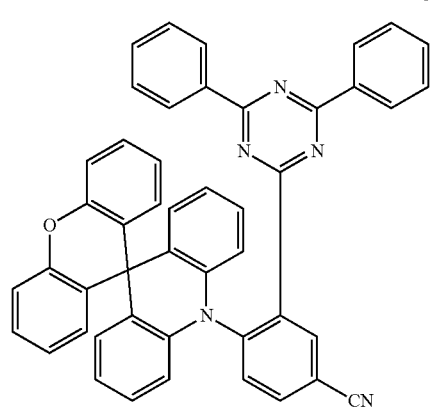
Compound 1-28
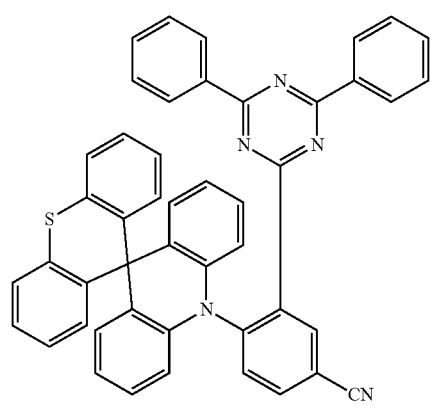
Compound 1-29
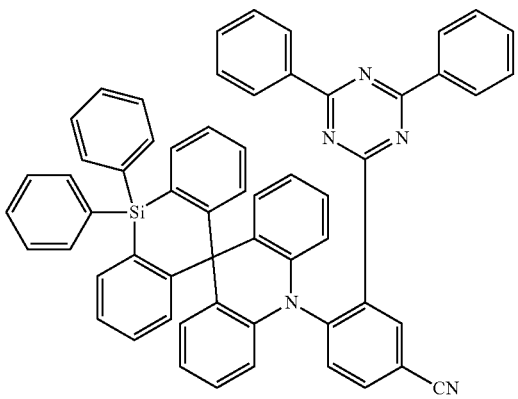
Compound 1-30
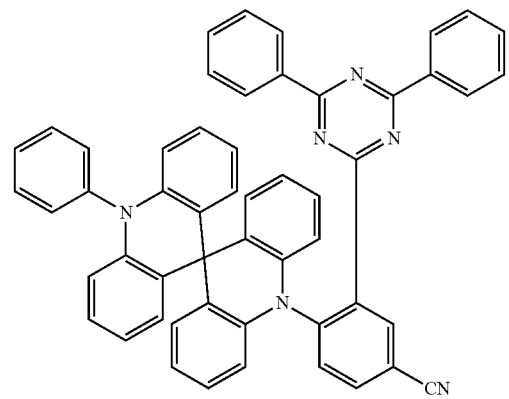
Compound 1-31
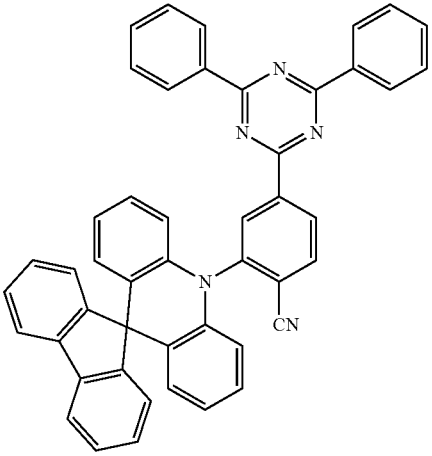

Compound 1-32
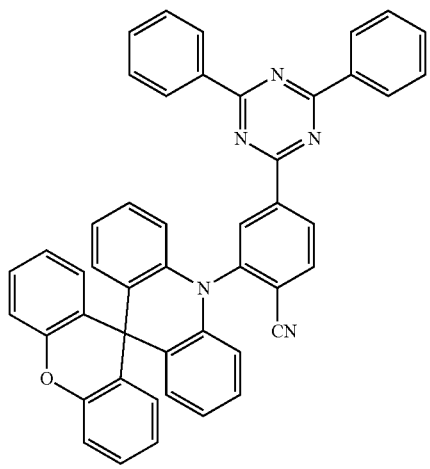
Compound 1-33
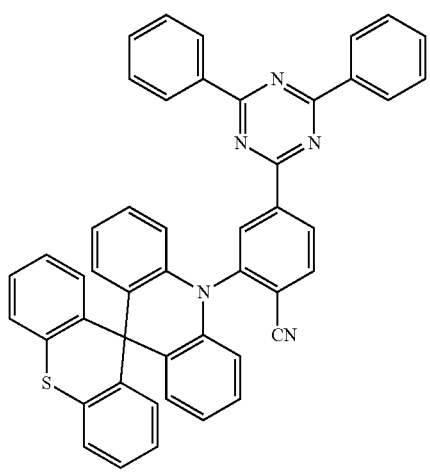
Compound 1-34
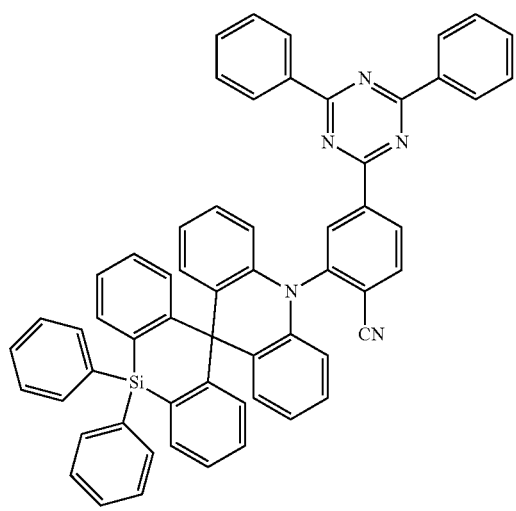
Compound 1-35
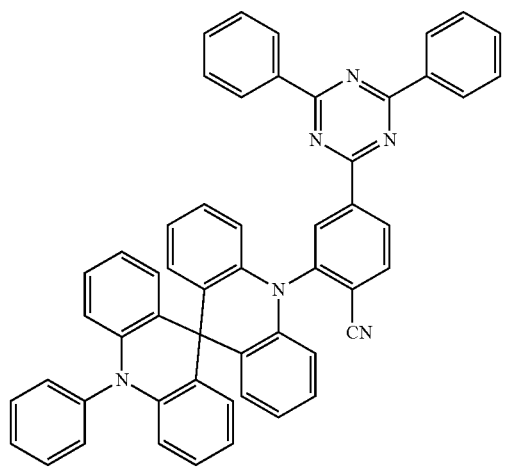
Compound 1-36
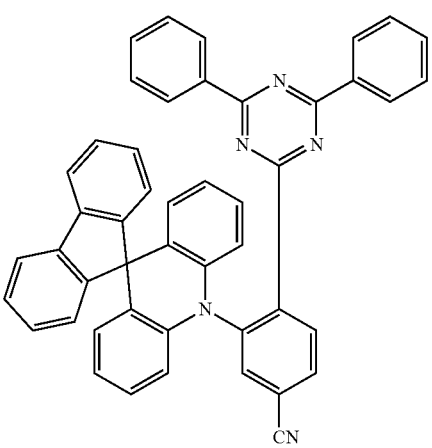
Compound 1-37
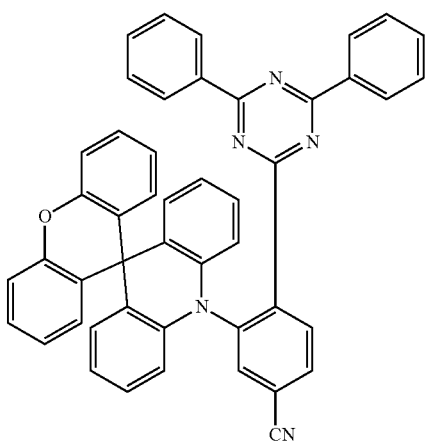

-continued
Compound 1-38
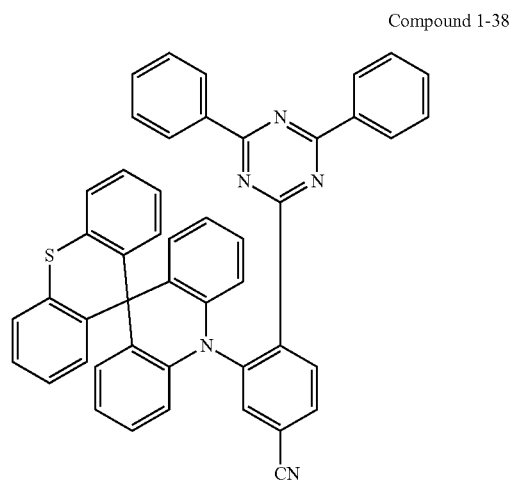
Compound 1-39
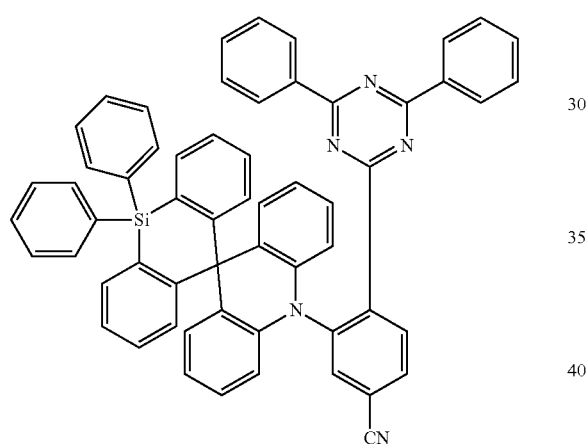
Compound 1-40
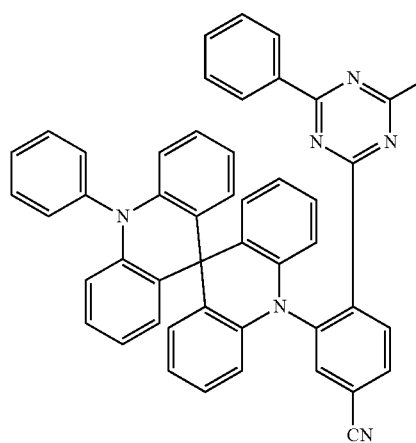
-continued
Compound 1-41
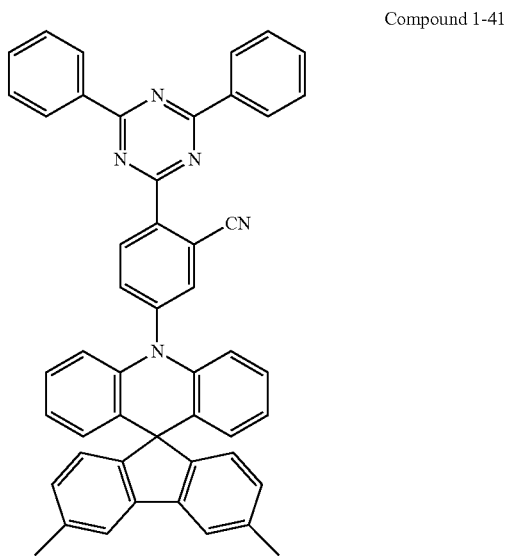
Compound 1-42
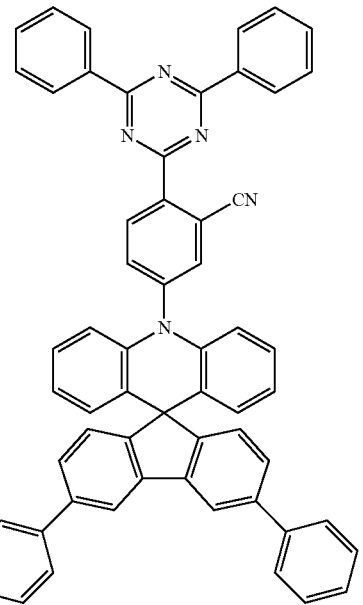

Compound 1-43
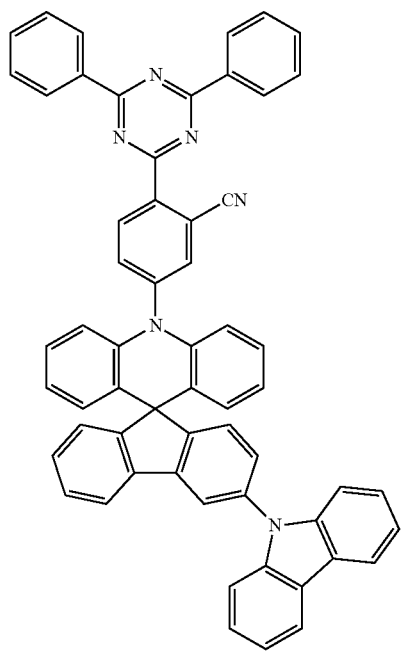
Compound 1-45
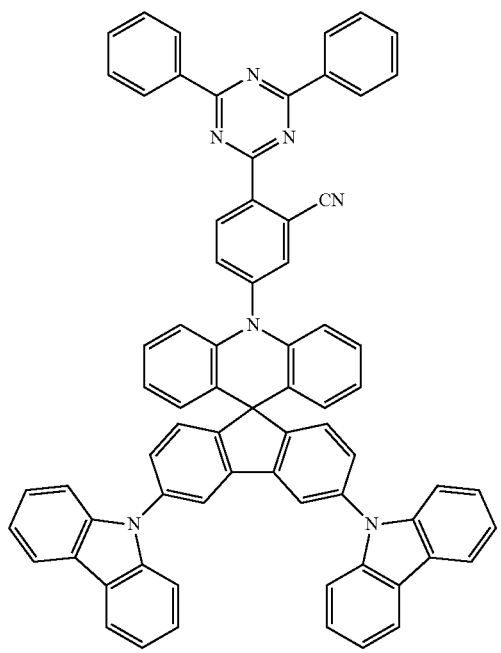
Compound 1-44
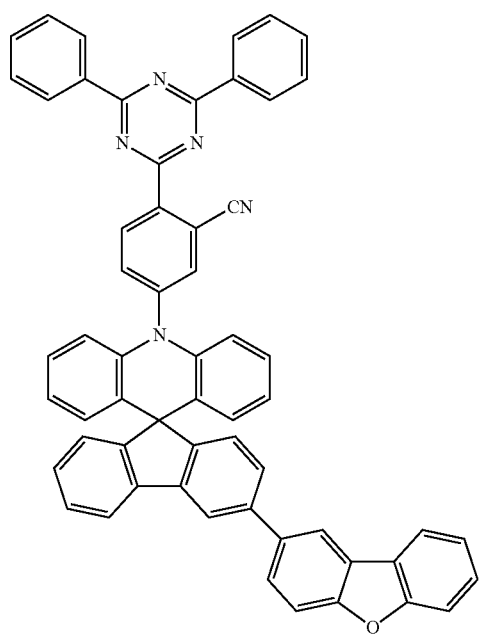
Compound 1-46
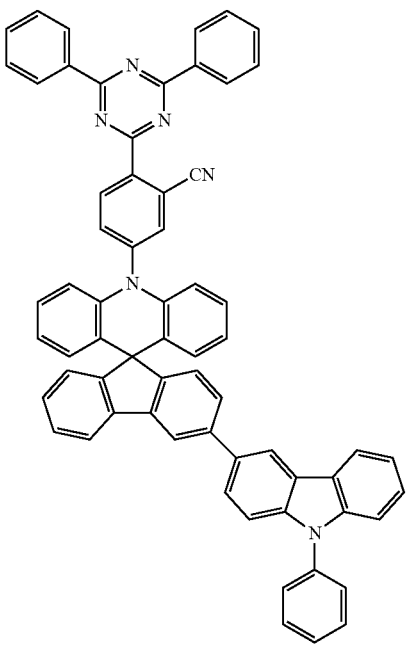

101
-continued
Compound 1-47
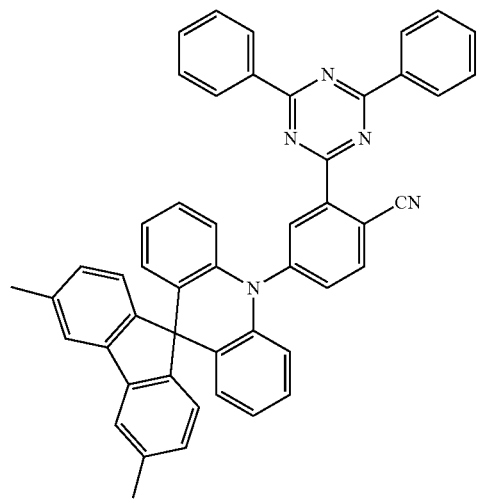
102
-continued
Compound 1-49
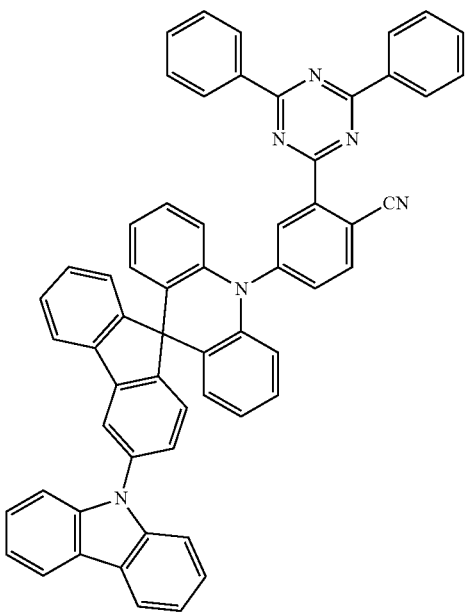
Compound 1-48
Compound 1-50
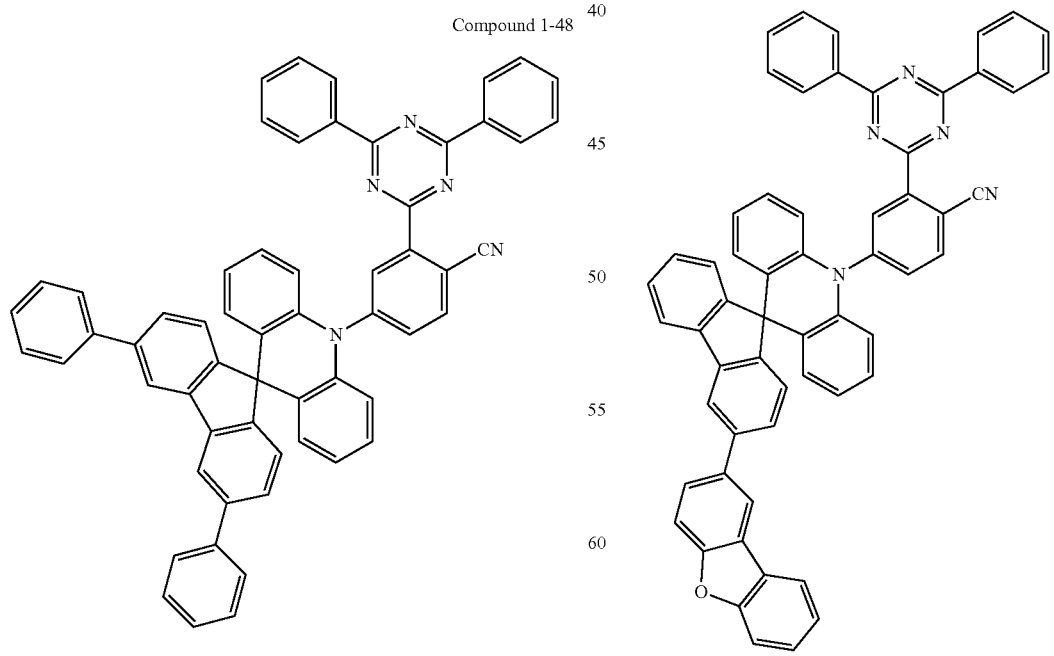

Compound 1-51
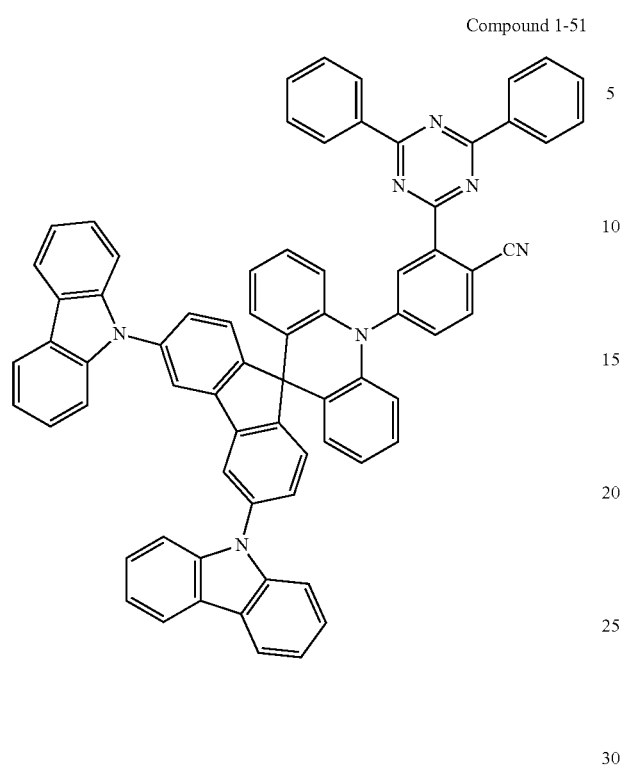
Compound 1-53
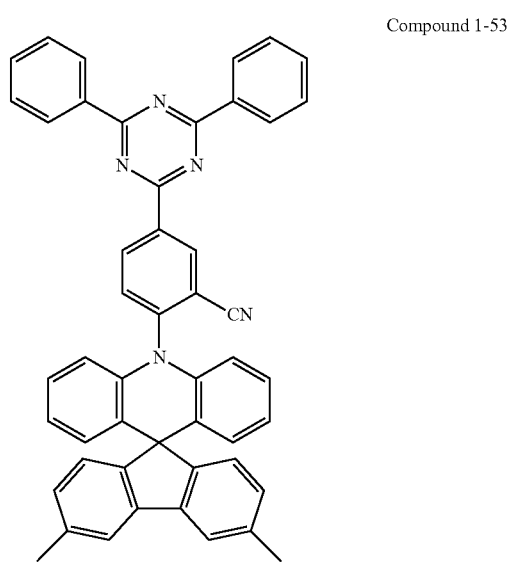
Compound 1-52
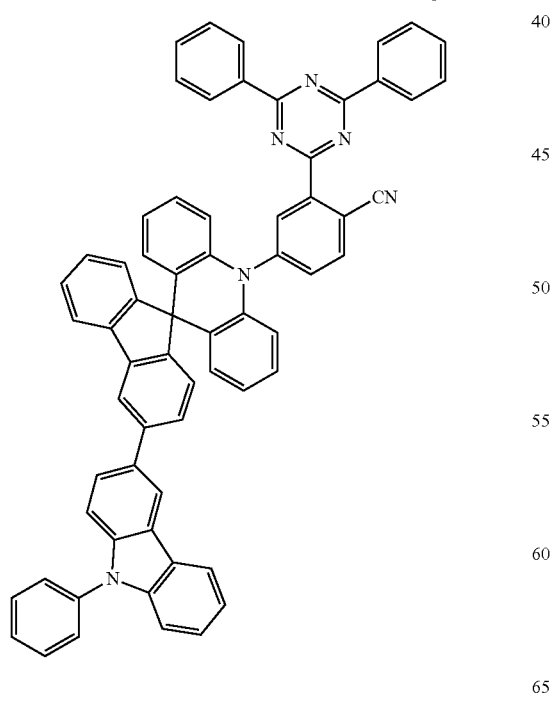
Compound 1-54
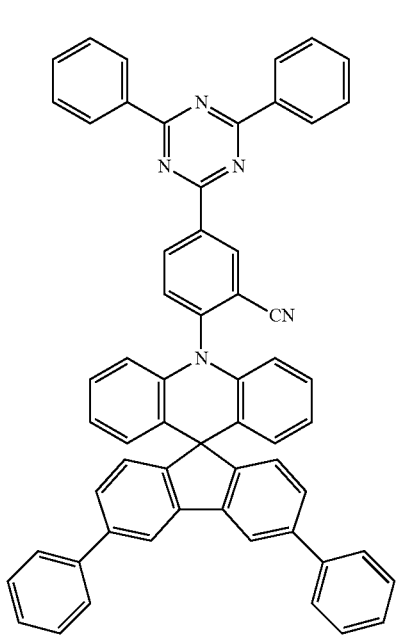

Compound 1-55
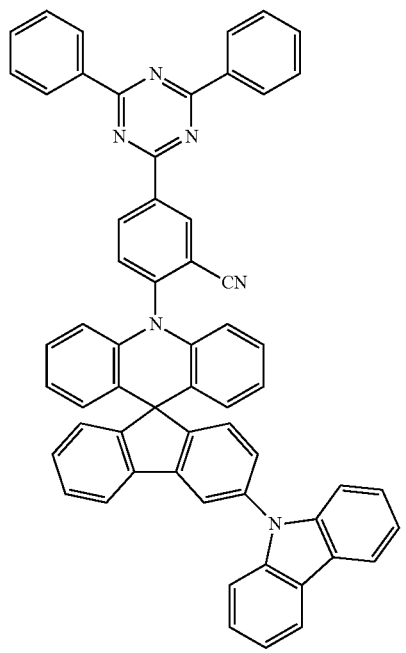
Compound 1-57
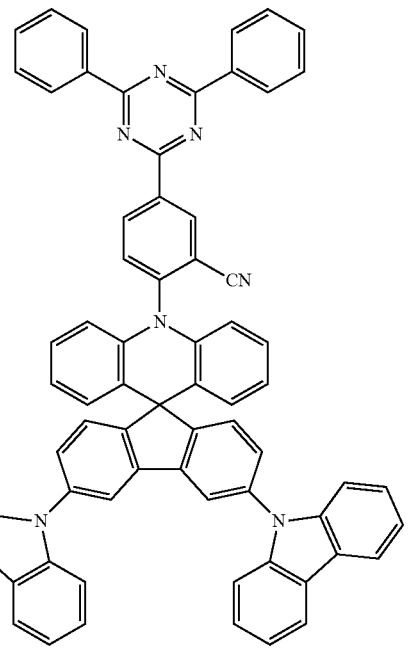
Compound 1-56
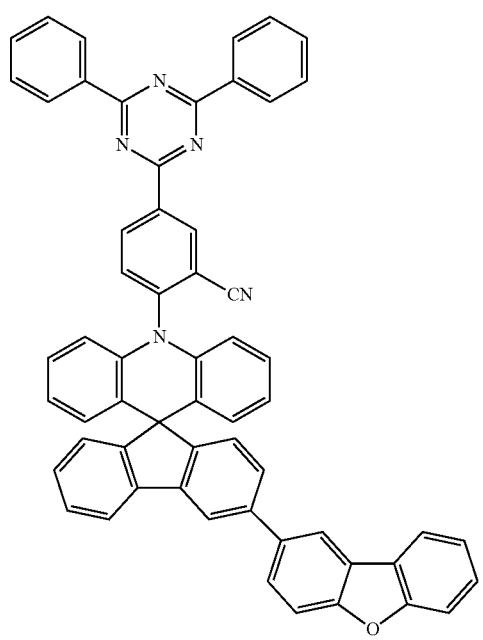
Compound 1-58
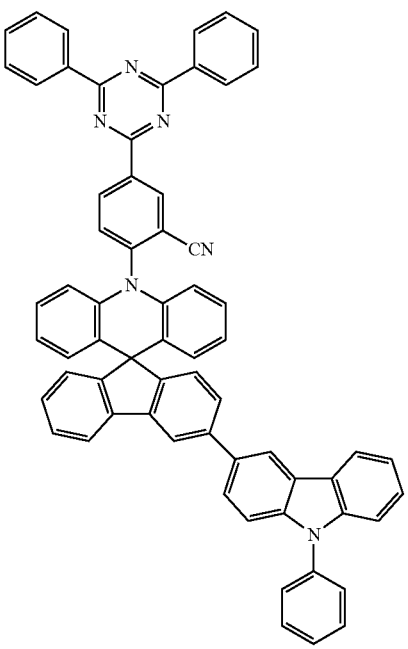

Compound 1-59
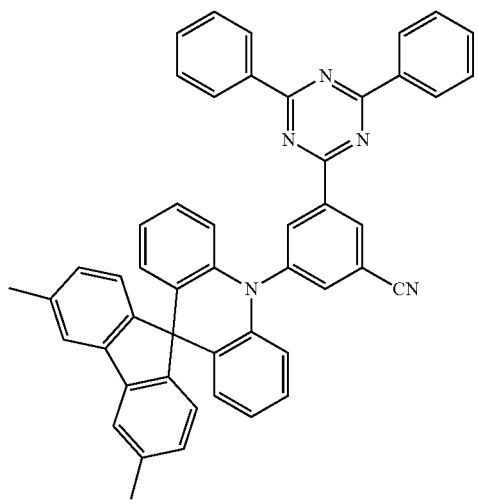
Compound 1-60
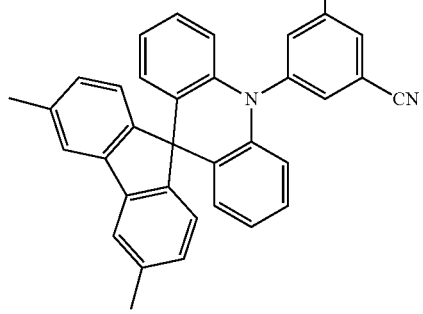
Compound 1-61
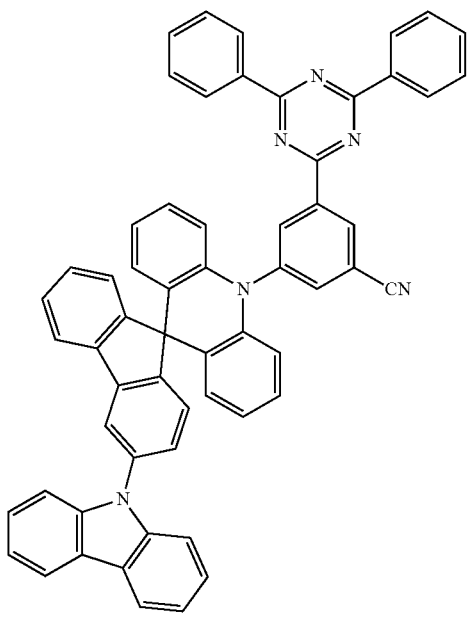
Compound 1-62
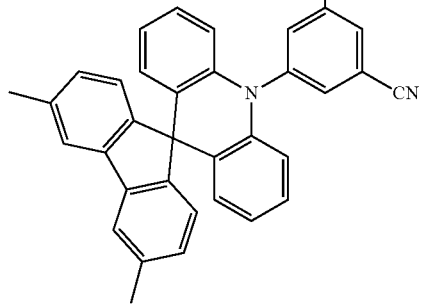

Compound 1-63

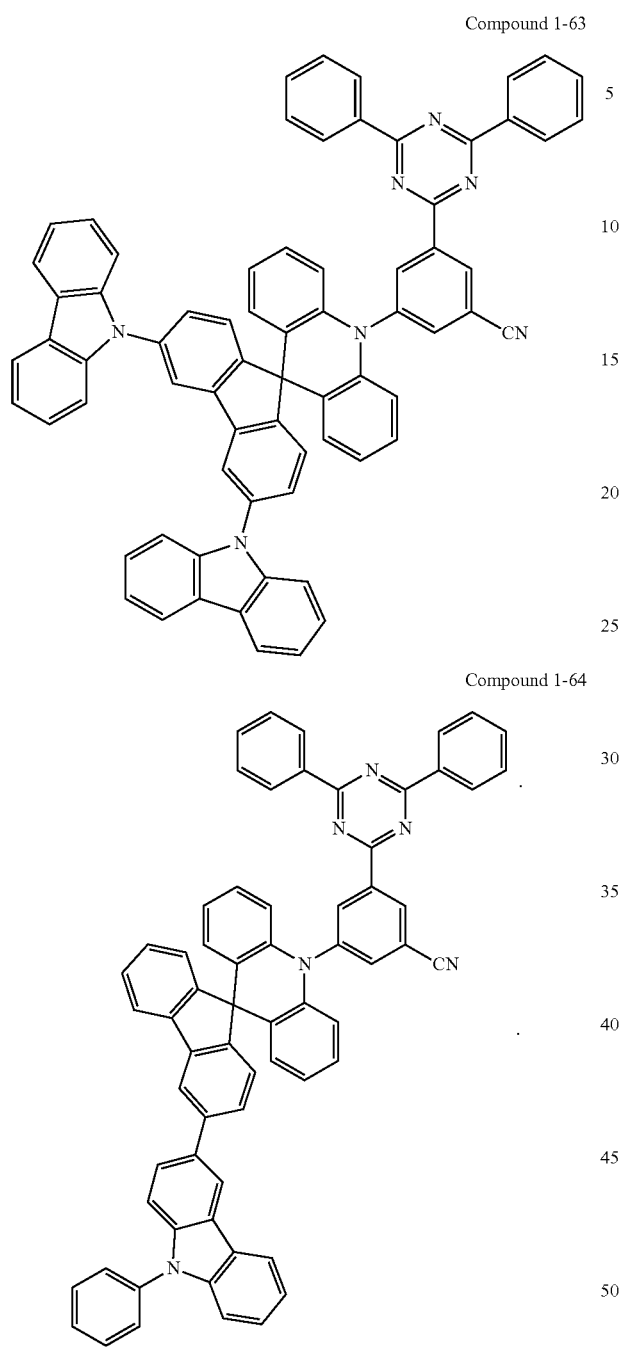

Compound 1-64

Chemical Formula 8

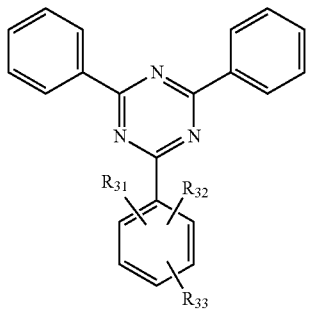

wherein each of $R_{31}$ and $R_{32}$ is a cyano group; and $R_{33}$ is a moiety having the following structure of Chemical Formula 9 or Chemical Formula 10:

Chemical Formula 9

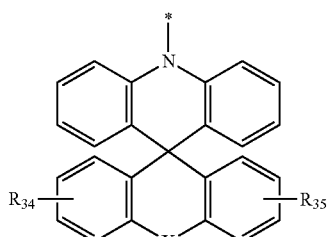

Chemical Formula 10

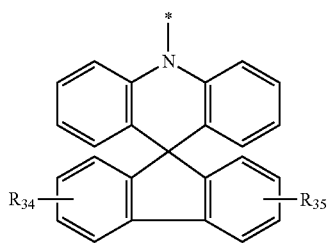

wherein each of $R_{34}$ and $R_{35}$ is independently selected from the group consisting of protium, deuterium, tritium, $C_1$~$C_{20}$ alkyl group, $C_5$~$C_{30}$ aryl group unsubstituted or substituted with an aromatic group, a hetero aromatic group or a combination thereof, and $C_4$~$C_{30}$ hetero aryl group unsubstituted or substituted with an aromatic group, a hetero aromatic group or a combination thereof; X in Chemical Formula 9 is $CR_{11}R_{12}$, $SiR_{14}R_{15}$, oxygen (O) or sulfur (S), wherein each of $R_{11}$ to $R_{15}$ is independently selected from the group consisting of protium, deuterium, tritium, $C_1$~$C_{20}$ alkyl group, $C_1$~$C_{20}$ alkoxy group, $C_1$~$C_{20}$ silyl group, $C_5$~$C_{30}$ aryl group and $C_4$~$C_{30}$ hetero aryl group.

4. The organic compound of claim 2, wherein the organic compound has a HOMO energy level between about −5.0 and about −6.0 eV, and a LUMO energy level between about −2.5 and about −3.5 eV; and wherein an energy bandgap between the HOMO energy level and the LUMO energy level is between about 2.2 to about 3.0 eV.

5. The organic compound of claim 1, wherein the organic compound has the following structure of Chemical Formula 8:

6. The organic compound of claim 5, wherein the organic compound has the following structure of Chemical Formula 11, Chemical Formula 11
Compound 2-1
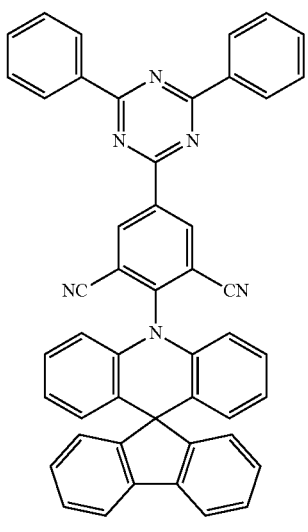
Compound 2-2
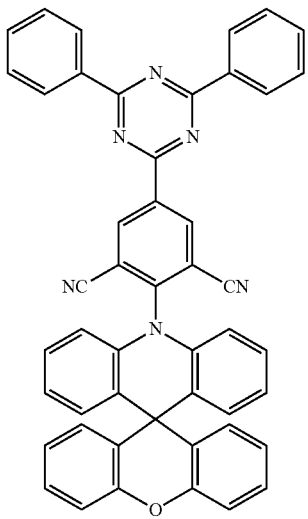
Compound 2-3
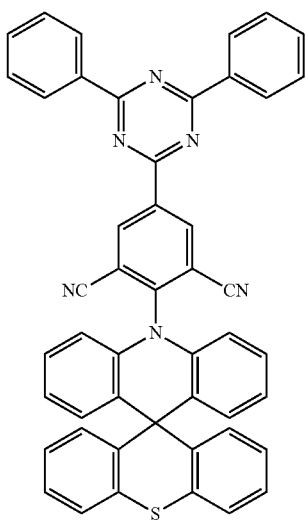
-continued
Compound 2-4
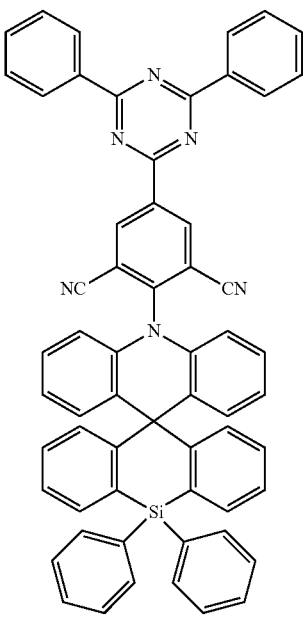
Compound 2-5
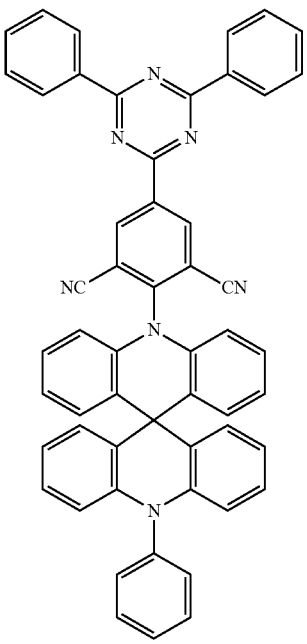

Compound 2-6
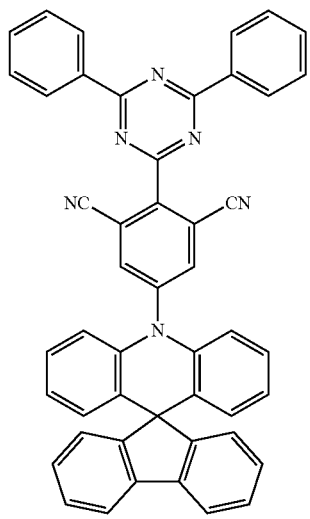
Compound 2-7
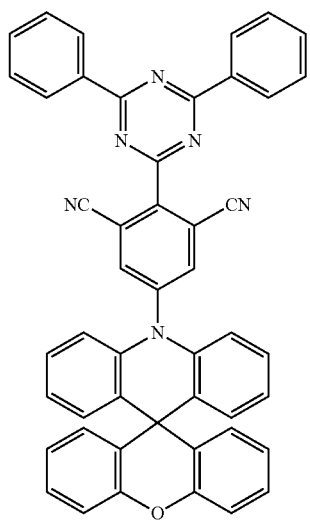
Compound 2-8
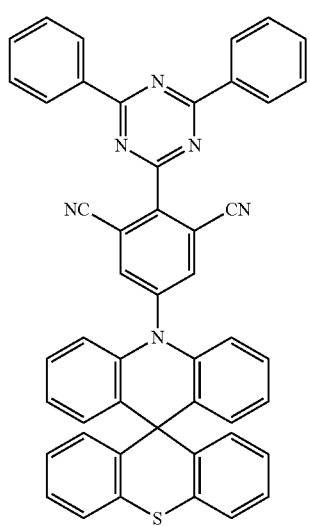
Compound 2-9
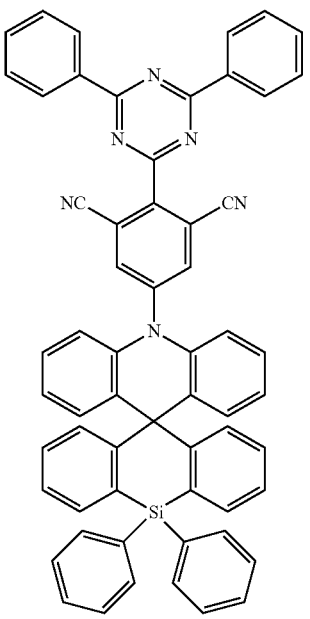
Compound 2-10
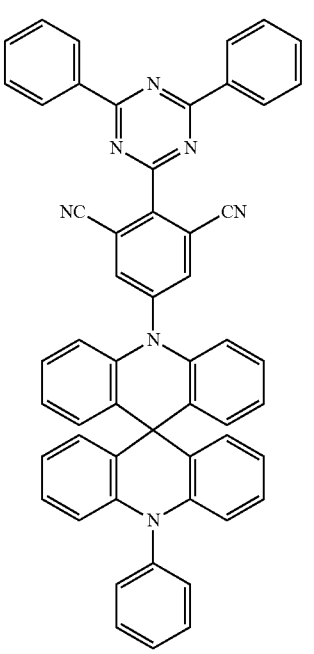

-continued
Compound 2-11
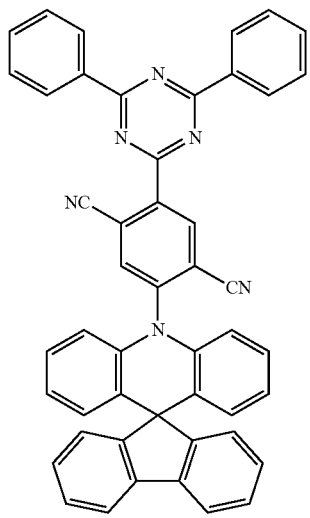
Compound 2-12
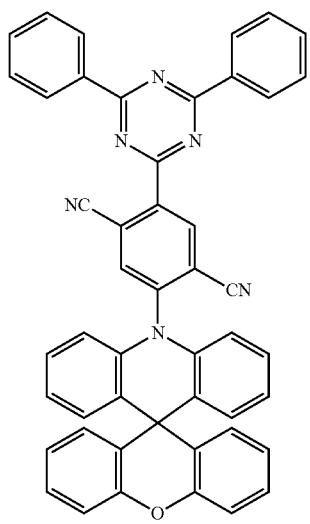
Compound 2-13
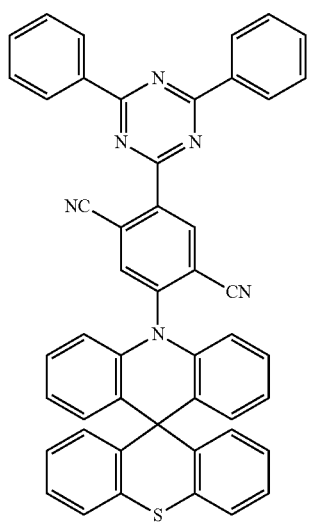
Compound 2-14
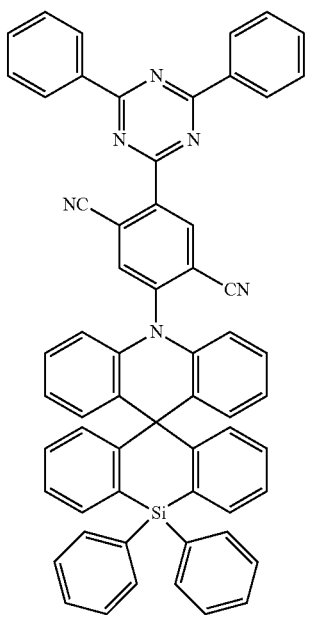
Compound 2-15
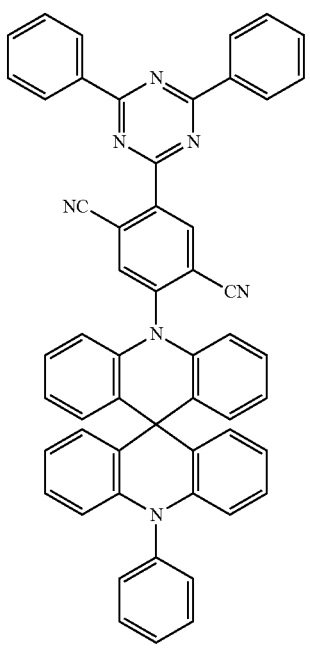

Compound 2-16
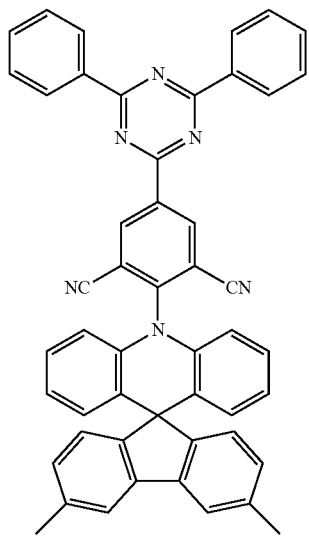
Compound 2-18
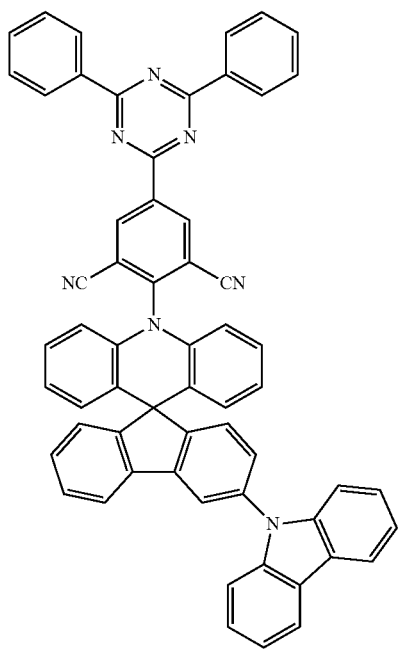
Compound 2-17
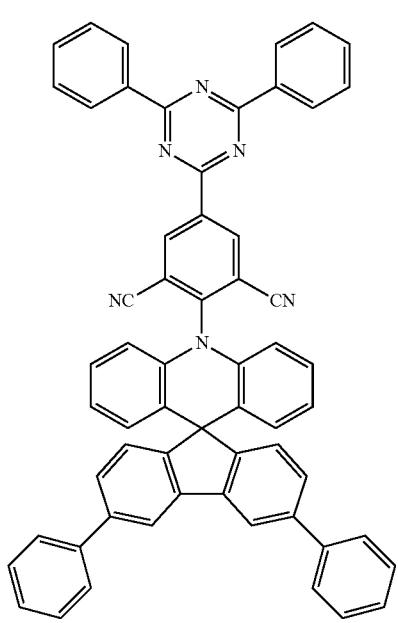
Compound 2-19
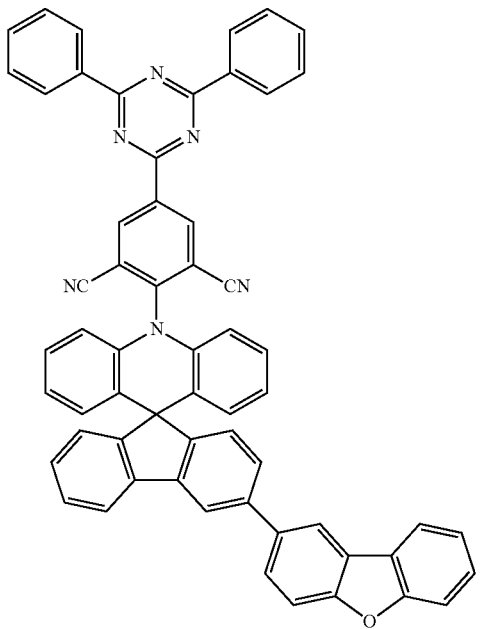

Compound 2-20
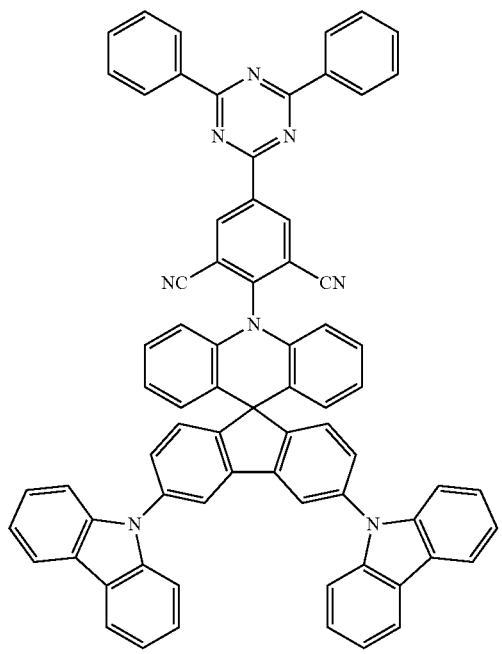
Compound 2-22
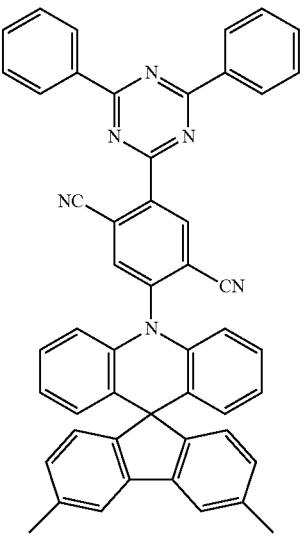
Compound 2-21
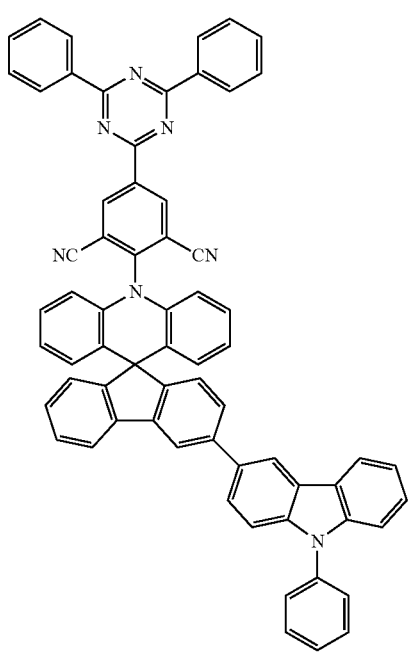
Compound 2-23
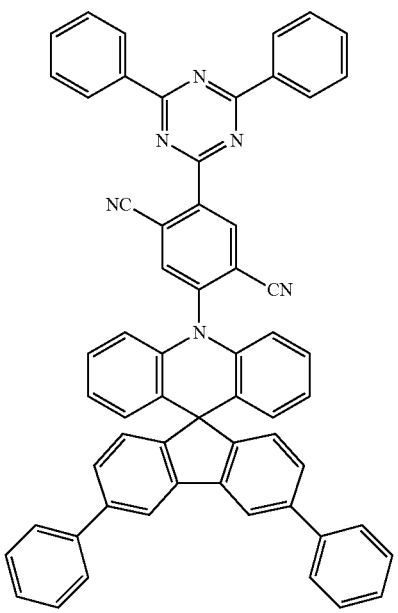

Compound 2-24

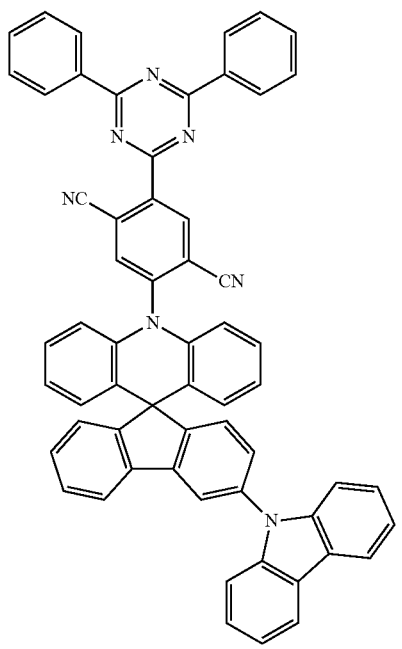

Compound 2-26

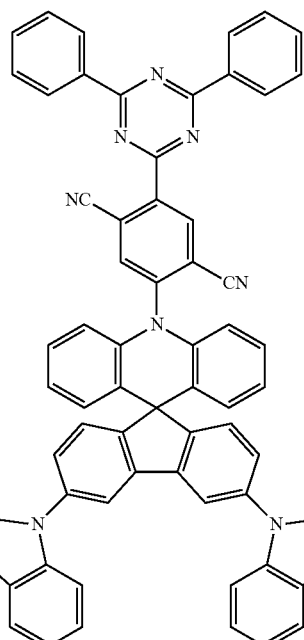

Compound 2-27

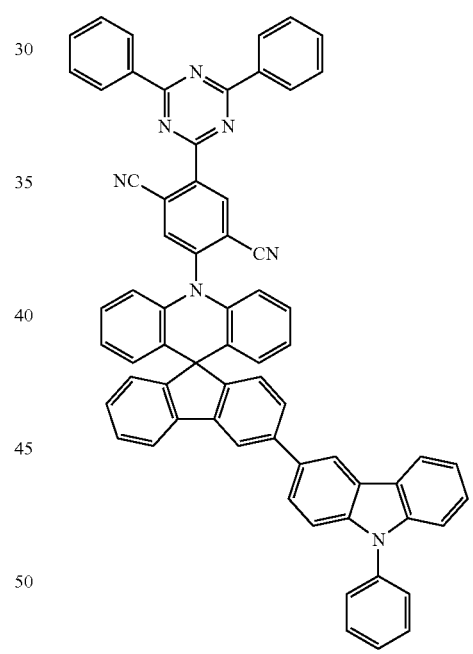

Compound 2-25

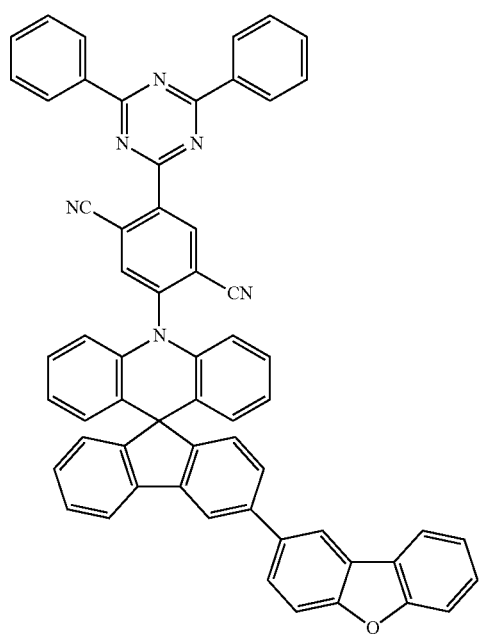

7. The organic compound of claim 5, wherein the organic compound has a HOMO energy level between about −5.0 and about −6.0 eV, and a LUMO energy level between about −2.5 and about −3.5 eV; and wherein an energy bandgap between the HOMO energy level and the LUMO energy level is between about 2.2 to about 3.0 eV.

8. The organic compound of claim 1, wherein the organic compound has a HOMO energy level between about −5.0 and about −6.0 eV, and a LUMO energy level between about −2.5 and about −3.5 eV; and wherein an energy bandgap between the HOMO energy level and the LUMO energy level is between about 2.2 to about 3.0 eV.

9. An organic light emitting diode, comprising:
a first electrode;
a second electrode,
wherein the first electrode and second electrode face each other; and
at least one emitting unit comprising an emitting material layer disposed between the first and second electrodes,
wherein the emitting material layer comprises an organic compound having the following structure of Chemical Formula 1:

Chemical Formula 1

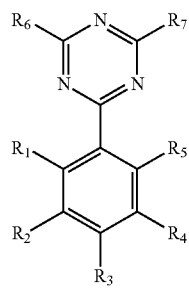

wherein each of $R_1$ to $R_5$ is independently protium, deuterium, tritium, halogen, $C_1$~$C_{10}$ alkyl halide, cyano group, nitro group or a moiety having the following structure of Chemical Formula 2 or Chemical Formula 3, wherein at least one of $R_1$ to $R_5$ is selected from the group consisting of halogen, $C_1$~$C_{10}$ to alkyl halide, cyano group and nitro group, and at least one of $R_1$ to $R_5$ is a moiety of Chemical Formula 2 or Chemical Formula 3; each of $R_6$ and $R_7$ is independently $C_5$~$C_{30}$ aryl group or $C_4$~$C_{30}$ hetero aryl group:

Chemical Formula 2

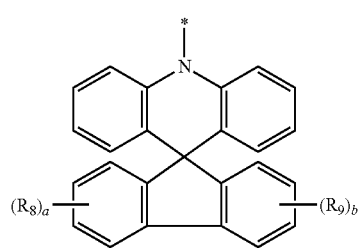

Chemical Formula 3

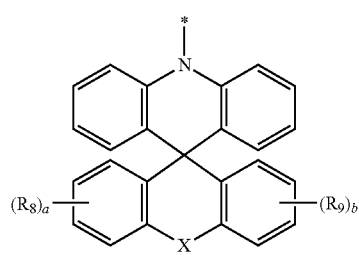

wherein each of $R_8$ and $R_9$ is independently selected from the group consisting of protium, deuterium, tritium, $C_1$~$C_{20}$ alkyl group, $C_1$~$C_{20}$ alkoxy group, $C_1$~$C_{20}$ silyl group, $C_5$~$C_{30}$ aryl group, $C_4$~$C_3$O hetero aryl group, $C_5$~$C_{30}$ aryl amino group and $C_4$~$C_{30}$ hetero aryl amino group, wherein each of the $C_5$~$C_{30}$ aryl group, the $C_4$~$C_{30}$ hetero aryl group, the $C_5$~$C_{30}$ aryl amino group and the $C_4$~$C_{30}$ hetero aryl amino group is unsubstituted or substituted with an aromatic group, a hetero aromatic group or a combination thereof, respectively; each of a and b is a number of a substituent and is independently an integer of 1 to 3; X in Chemical Formula 3 is $CR_{11}R_{12}$, $NR_{13}$, $SiR_{14}R_{15}$, oxygen (O) or sulfur (S), wherein each of $R_{11}$ to $R_{15}$ is independently selected from the group consisting of protium, deuterium, tritium, $C_1$~$C_{20}$ alkyl group, $C_1$~$C_{20}$ alkoxy group, $C_1$~$C_{20}$ silyl group, $C_5$~$C_{30}$ aryl group and $C_4$~$C_{30}$ hetero aryl group.

10. The organic light emitting diode of claim 9, wherein the organic compound has the following structure of Chemical Formula 4:

Chemical Formula 4

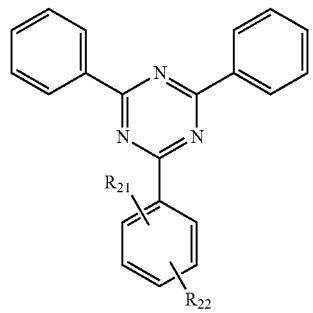

wherein $R_{21}$ is cyano group; and $R_{22}$ is a moiety having the following structure of Chemical Formula 5 or Chemical Formula 6:

Chemical Formula 5

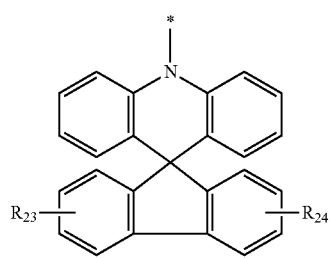

Chemical Formula 6

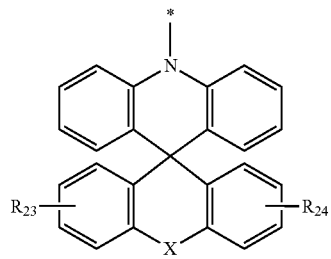

wherein each of $R_{23}$ and $R_{24}$ is independently selected from the group consisting of protium, deuterium, tritium, $C_1$~$C_{20}$ alkyl group, $C_5$~$C_{30}$ aryl group unsubstituted or substituted with aromatic group, hetero aromatic group or combination thereof and $C_4$~$C_{30}$ hetero aryl group unsubstituted or substituted with aromatic group, hetero aromatic group or combination thereof; X in Chemical Formula 6 is $CR_{11}R_{12}$, $NR_{13}$, $SiR_{14}R_{15}$, oxygen (O) or sulfur (S), wherein each of $R_{11}$ to $R_{15}$ is independently selected from the group consisting of protium, deuterium, tritium, $C_1$~$C_{20}$ alkyl group, $C_1$~$C_{20}$ alkoxy group, $C_1$~$C_{20}$ silyl group, $C_5$~$C_{30}$ aryl group and $C_4$~$C_{30}$ hetero aryl group.

11. The organic light emitting diode of claim 9, wherein the organic compound has the following structure of Chemical Formula 8:

Chemical Formula 8

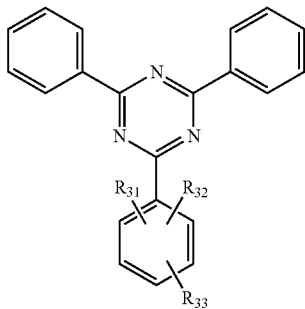

wherein each of $R_{31}$ and $R_{32}$ is cyano group; and $R_{33}$ is a moiety having the following structure of Chemical Formula 9 or Chemical Formula 10:

Chemical Formula 9

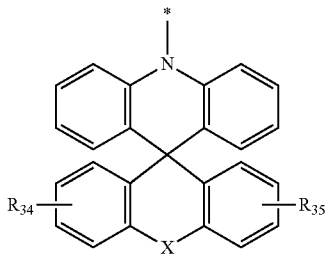

Chemical Formula 10

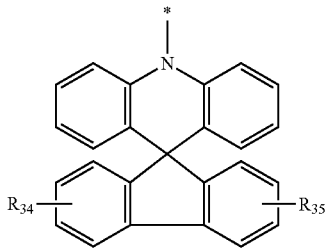

wherein each of $R_{34}$ and $R_{35}$ is independently selected from the group consisting of protium, deuterium, tritium, $C_1$~$C_{20}$ alkyl group, $C_5$~$C_{30}$ aryl group unsubstituted or substituted with aromatic group, hetero aromatic group or combination thereof, and $C_4$~$C_{30}$ hetero aryl group unsubstituted or substituted with aromatic group, hetero aromatic group or combination thereof; X in Chemical Formula 9 is $CR_{11}R_{12}$, $NR_{13}$, $SiR_{14}R_{15}$, oxygen (O) or sulfur (S), wherein each of $R_{11}$ to $R_{15}$ is independently selected from the group consisting of protium, deuterium, tritium, $C_1$~$C_{20}$ alkyl group, $C_1$~$C_{20}$ alkoxy group, $C_1$~$C_{20}$ silyl group, $C_5$~$C_{30}$ aryl group and $C_4$~$C_{30}$ hetero aryl group.

12. The organic light emitting diode of claim 9, wherein the emitting material layer includes a first host and a first dopant, and wherein the first dopant comprises the organic compound.

13. The organic light emitting diode of claim 12, wherein an energy level bandgap ($|HOMO^H-HOMO^{TD}|$) between a Highest Occupied Molecular Orbital energy level ($HOMO^H$) of the first host and a Highest Occupied Molecular Orbital energy level ($HOMO^{TD}$) of the first dopant or an energy level bandgap ($|LUMO^H-LUMO^{TD}|$) between a Lowest Unoccupied Molecular Orbital energy level ($LUMO^H$) of the first host and a Lowest Unoccupied Molecular Orbital energy level ($LUMO^{TD}$) of the first dopant is equal to or less than about 0.5 eV.

14. The organic light emitting diode of claim 12, wherein each of an excited state singlet energy level ($S_1^H$) and an excited state triplet energy level ($T_1^H$) of the first host is higher than each of an excited state singlet energy level ($S_1^{TD}$) and an excited state triplet energy level ($T_1^{TD}$) of the first dopant, respectively.

15. The organic light emitting diode of claim 12, wherein the emitting material layer further comprises a second dopant, wherein an excited state triplet energy level ($T_1^{TD}$) of the first dopant is lower than an excited state triplet energy level ($T_1^H$) of the first host and an excited state singlet energy level ($S_1^{TD}$) of the first dopant is higher than an excited state singlet energy level ($S_1^{FD}$) of the second dopant.

16. The organic light emitting diode of claim 9, wherein the emitting material layer comprises a first emitting material layer disposed between the first and second electrodes, wherein the first emitting material comprises the organic compound, wherein the emitting material layer further comprises a second emitting material layer disposed between the first electrode and the first emitting material layer or between the first emitting material layer and the second electrode.

17. The organic light emitting diode of claim 16, wherein the first emitting material layer comprises a first host and a first dopant, and wherein the first dopant comprises the organic compound.

18. The organic light emitting diode of claim 17, wherein the second emitting material layer comprises a second host and a second dopant.

19. The organic light emitting diode of claim 18, wherein an excited state singlet energy level ($S_1^{TD}$) of the first dopant is higher than an excited state singlet energy level ($S_1^{FD}$) of the second dopant.

20. The organic light emitting diode of claim 18, wherein each of an excited state singlet energy level ($S_1^{H1}$) and an excited state triplet energy level ($T_1^{H1}$) of the first host is higher than each of an excited state singlet energy level ($S_1^{TD}$) and an excited state triplet energy level ($T_1^{TD}$) of the first dopant, respectively, and wherein an excited state singlet energy level ($S_1^{H2}$) of the second host is higher than an excited state singlet energy level ($S_1^{FD}$) of the second dopant.

21. The organic light emitting diode of claim 18, wherein the second emitting material layer is disposed between the first electrode and the first emitting material layer, and wherein the organic light emitting diode further comprises an electron blocking layer disposed between the first electrode and the second emitting material layer.

22. The organic light emitting diode of claim 21, wherein the second host is the same as a material of the electron blocking layer.

23. The organic light emitting diode of claim 18, wherein the second emitting material layer is disposed between the first emitting material layer and the second electrode, and wherein the organic light emitting diode further comprises a hole blocking layer disposed between the second emitting material layer and the second electrode.

24. The organic light emitting diode of claim 23, wherein the second host is the same as a material of the hole blocking layer.

25. The organic light emitting diode of claim 16, wherein the emitting material layer further comprises a third emitting material layer disposed opposite to the second emitting material layer with respect to the first emitting material layer.

26. The organic light emitting diode of claim 25, wherein the first emitting material layer comprises a first host and a first dopant, and wherein the first dopant comprises the organic compound.

27. The organic light emitting diode of claim 26, wherein the second emitting material layer comprises a second host and a second dopant and the third emitting material layer comprises a third host and a third dopant.

28. The organic light emitting diode of claim 27, wherein an excited state singlet energy level ($S_1^{TD}$) of the first dopant is higher than each of excited state singlet energy levels ($S_1^{FD1}$ and $S_1^{FD2}$) of the second and third dopants, respectively.

29. The organic light emitting diode of claim 27, wherein each of an excited state singlet energy level ($S_1^{H1}$) and an excited state triplet energy level ($T_1^{H1}$) of the first host is higher than each of an excited state singlet energy level ($S_1^{TD}$) and an excited state triplet energy level ($T_1^{TD}$) of the first dopant, respectively, wherein an excited state singlet energy level ($S_1^{H2}$) of the second host is higher than an excited state singlet energy level ($S_1^{FD1}$) of the second dopant, and wherein an excited state singlet energy level ($S_1^{H3}$) of the third host is higher than an excited state singlet energy level ($S_1^{FD2}$) of the third dopant.

30. The organic light emitting diode of claim 27, wherein the second emitting material layer is disposed between the first electrode and the first emitting material layer and the third emitting material layer is disposed between the first emitting material layer and the second electrode, and wherein the organic light emitting diode further comprises an electron blocking layer disposed between the first electrode and the second emitting material layer.

31. The organic light emitting diode of claim 30, wherein the second host is the same as a material of the electron blocking layer.

32. The organic light emitting diode of claim 27, wherein the second emitting material layer is disposed between the first electrode and the first emitting material layer, and wherein the third emitting material layer is disposed between the first emitting material layer and the second electrode, and wherein the organic light emitting diode further comprises a hole blocking layer disposed between the third emitting material layer and the second electrode.

33. The organic light emitting diode of claim 32, wherein the third host is the same as a material of the hole blocking layer.

34. The organic light emitting diode of claim 33, further comprising an electron blocking layer disposed between the first electrode and the second emitting material layer, wherein the second host is a same as a material of the electron blocking layer.

35. The organic light emitting diode of claim 9, wherein the at least one emitting unit includes a first emitting unit disposed between the first and second electrodes and including a lower emitting material layer and a second emitting unit disposed between the first emitting unit and the second electrode and including an upper emitting material layer, and wherein at least one of the lower emitting material layer and the upper emitting material layer includes the organic compound, and further comprises a charge generation layer disposed between the first and second emitting units.

36. The organic light emitting diode of claim 35, wherein the organic compound includes an organic compound having the following structure of Chemical Formula 4:

Chemical Formula 4

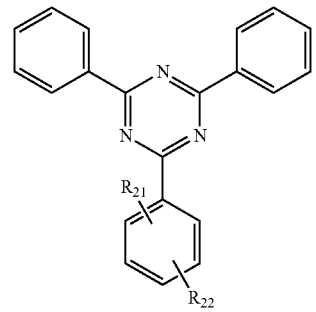

wherein $R_{21}$ is cyano group; and $R_{22}$ is a moiety having the following structure of Chemical Formula 5 or Chemical Formula 6:

Chemical Formula 5

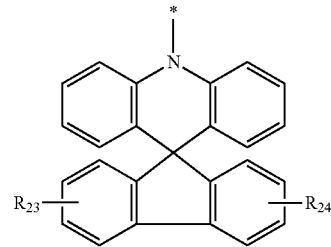

Chemical Formula 6

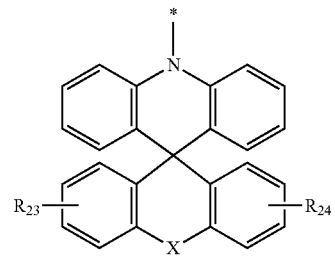

wherein each of $R_{23}$ and $R_{24}$ is independently selected from the group consisting of protium, deuterium, tritium, $C_1$~$C_{20}$ alkyl group, $C_5$~$C_{30}$ aryl group unsubstituted or substituted with aromatic group, hetero aromatic group or combination thereof and $C_4$~$C_{30}$ hetero aryl group unsubstituted or substituted with aromatic group, hetero aromatic group or combination thereof; X in Chemical Formula 6 is $CR_{11}R_{12}$, $NR_{13}$, $SiR_{14}R_{15}$, oxygen (O) or sulfur (S), wherein each of $R_{11}$ to $R_{15}$ is independently selected from the group consisting of protium, deuterium, tritium, $C_1$~$C_{20}$ alkyl group, $C_1$~$C_{20}$ alkoxy group, $C_1$~$C_{20}$ silyl group, $C_5$~$C_{30}$ aryl group and $C_4$~$C_{30}$ hetero aryl group.

37. The organic light emitting diode of claim 35, wherein the organic compound includes an organic compound having the following structure of Chemical Formula 8:

Chemical Formula 8

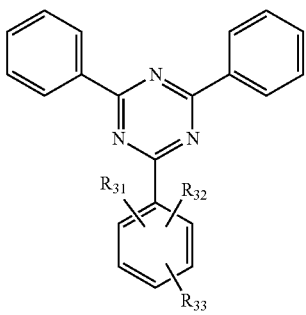

wherein each of $R_{31}$ and $R_{32}$ is cyano group; and $R_{33}$ is a moiety having the following structure of Chemical Formula 9 or Chemical Formula 10:

Chemical Formula 9

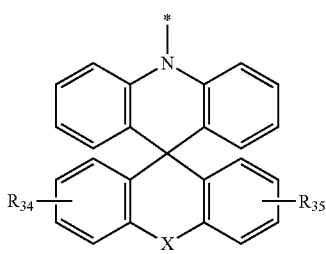

Chemical Formula 10

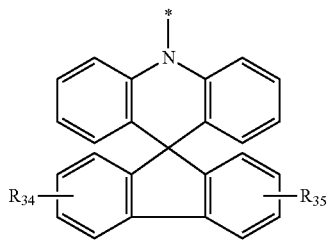

wherein each of $R_{34}$ and $R_{35}$ is independently selected from the group consisting of protium, deuterium, tritium, $C_1$~$C_{20}$ alkyl group, $C_5$~$C_{30}$ aryl group unsubstituted or substituted with aromatic group, hetero aromatic group or combination thereof and $C_4$~$C_{30}$ hetero aryl group unsubstituted or substituted with aromatic group, hetero aromatic group or combination thereof; X in Chemical Formula 9 is is $CR_{11}R_{12}$, $NR_{13}$, $SiR_{14}R_{15}$, oxygen (O) or sulfur (S), wherein each of $R_{11}$ to $R_{15}$ is independently selected from the group consisting of protium, deuterium, tritium, $C_1$~$C_{20}$ alkyl group, $C_1$~$C_{20}$ alkoxy group, $C_1$~$C_{20}$ silyl group, $C_5$~$C_{30}$ aryl group and $C_4$~$C_{30}$ hetero aryl group.

38. The organic light emitting diode of claim 35, wherein at least one of the lower emitting material layer and the upper emitting material layer includes a first emitting material layer including the organic compound and a second emitting material layer disposed between the first electrode and the first emitting material layer or between the first emitting material layer and the second electrode.

39. The organic light emitting diode of claim 38, wherein at least one of the lower emitting material layer and the upper emitting material layer further comprises a third emitting material layer disposed oppositely to the second emitting material layer with respect to the first emitting material layer.

40. An organic light emitting device, comprising:
a substrate; and
the organic light emitting diode according to claim 9 over the substrate.

* * * * *